United States Patent
Laufersweiler et al.

(10) Patent No.: US 6,677,337 B2
(45) Date of Patent: Jan. 13, 2004

(54) 1,2-DIHYDROPYRAZOL-3-ONES WHICH CONTROLS INFLAMMATORY CYTOKINES

(75) Inventors: Matthew John Laufersweiler, Morrow, OH (US); Cynthia Monesa Crago Clark, Loveland, OH (US); Michael Philip Clark, Loveland, OH (US); Jane Far-Jine Djung, Mason, OH (US); Biswanath De, Cincinnati, OH (US); Michael George Natchus, Alpharetta, GA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/382,060

(22) Filed: Mar. 5, 2003

(65) Prior Publication Data
US 2003/0225082 A1 Dec. 4, 2003

Related U.S. Application Data
(60) Provisional application No. 60/365,701, filed on Mar. 19, 2002.

(51) Int. Cl.⁷ .................. A61K 31/513; A61K 31/5377; A61P 29/00; C07D 403/04; C07D 413/14

(52) U.S. Cl. .................. 514/235.8; 514/274; 514/275; 544/122; 544/123; 544/317; 544/331

(58) Field of Search ................................. 544/122, 123, 544/317, 331; 514/235.8

(56) References Cited

U.S. PATENT DOCUMENTS
4,663,327 A * 5/1987 Sasse et al. .................. 544/317

* cited by examiner

Primary Examiner—Robert W. Ramsuer
(74) Attorney, Agent, or Firm—Richard S. Echler, Sr.

(57) ABSTRACT

The present invention relates to compounds which are capable of preventing the extracellular release of inflammatory cytokines, said compounds, or enantiomeric and diasteriomeric forms or pharmaceutically acceptable salts thereof, have the formula:

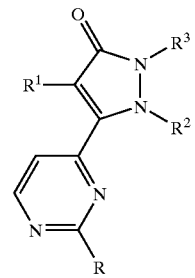

wherein R is an ether or amino unit,
  $R^1$ is substituted phenyl,
  each $R^2$ and $R^3$ unit is independently selected from the group consisting of:
  a) hydrogen; and
  b) substituted or unsubstituted $C_1-C_{10}$ hydrocarbyl selected from the group consisting of:
    i) $C_1-C_{10}$ linear, branched or cyclic alkyl;
    ii) $C_1-C_{10}$ aryl;
    iii) $C_1-C_{10}$ heterocyclic;
    iv) $C_1-C_{10}$ heteroaryl.

55 Claims, No Drawings

1,2-DIHYDROPYRAZOL-3-ONES WHICH CONTROLS INFLAMMATORY CYTOKINES

CROSS REFERENCE TO RELATED APPLICATIONS

This application claims priority under Title 35, United States Code 119(e) from Provisional Application Serial No. 60/365,701, filed Mar. 19, 2002.

FIELD OF THE INVENTION

The present invention relates to 1,2-dihydropyrazol-3-ones which inhibit the extracellular release of inflammatory cytokines, said cytokines responsible for one or more human or higher mammalian disease states. The present invention further relates to compositions comprising said 1,2-dihydropyrazol-3-ones and method for preventing, abating, or otherwise controlling enzymes which are understood to be the active components responsible for the herein described disease states.

BACKGROUND OF THE INVENTION

Interleukin-1 (IL-1) and Tumor Necrosis Factor-α (TNF-α) are among the important biological substances known collectively as "cytokines." These molecules are understood to mediate the inflammatory response associated with the immunological recognition of infectious agents.

These pro-inflammatory cytokines are suggested as an important mediators in many disease states or syndromes, inter alia, rheumatoid arthritis, osteoarthritis, inflammatory bowel disease (IBS), septic shock, cardiopulmonary dysfunction, acute respiratory disease, cachexia, and therefore responsible for the progression and manifestation of human disease states.

There is therefore a long felt need for compounds and pharmaceutical compositions which comprise compounds, which can block, abate, control, mitigate, or prevent the release of cytokines from cells which produce them

SUMMARY OF THE INVENTION

The present invention meets the aforementioned needs in that it has been surprisingly found that certain bicyclic pyrazolones and derivatives thereof are effective for inhibiting release of inflammatory cytokines, inter alia, interleukin-1 (IL-1) and tumor necrosis factor (TNF) from cells and thereby preventing, abating, or otherwise controlling enzymes which are proposed to be the active components responsible for the herein described disease states.

The first aspect of the present invention relates to compounds, including all enantiomeric and diasteriomeric forms and pharmaceutically acceptable salts thereof, said compounds having the formula:

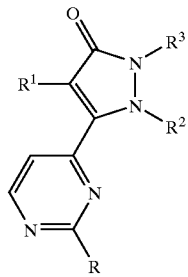

wherein R is:
a) —O[CH$_2$]$_n$R$^4$; or
b) —NR$^{5a}$R$^{5b}$;

R$^4$ is substituted or unsubstituted C$_1$–C$_{10}$ linear, branched, or cyclic alkyl; substituted or unsubstituted aryl; substituted or unsubstituted heterocyclic; or substituted or unsubstituted heteroaryl; the index n is from 0 to 5;

R$^{5a}$ and R$^{5b}$ are each independently:
a) hydrogen; or
b) —[C(R$^{6a}$R$^{6b}$)]$_m$R$^7$;

each R$^{6a}$ and R$^{6b}$ are independently hydrogen, —OR$^8$, —N(R$^8$)$_2$, —CO$_2$R$^8$, —CON(R$^8$)$_2$; C$_1$–C$_4$ linear, branched, or cyclic alkyl, and mixtures thereof; R$^7$ is hydrogen, substituted or unsubstituted C$_1$–C$_6$ alkyl, substituted or unsubstituted heterocyclic, substituted or unsubstituted aryl, or substituted or unsubstituted heteroaryl; —OR$^8$, —N(R$^8$)$_2$, —CO$_2$R$^8$, —CON(R$^8$)$_2$; R$^8$ is hydrogen, a water-soluble cation, C$_1$–C$_4$ alkyl, or substituted or unsubstituted aryl; the index m is from 0 to 5;

R$^1$ is substituted phenyl;

each R$^2$ and R$^3$ unit is independently selected from the group consisting of:
a) hydrogen; and
b) substituted or unsubstituted C$_1$–C$_{10}$ hydrocarbyl selected from the group consisting of:
i) C$_1$–C$_{10}$ linear, branched or cyclic alkyl;
ii) C$_6$–C$_{10}$ aryl;
iii) C$_1$–C$_{10}$ heterocyclic;
iv) C$_1$–C$_{10}$ heteroaryl.

Another aspect of the present invention relates to pharmaceutical compositions which can deliver the compounds of the present invention to a human or higher mammal, said compositions comprising:
a) an effective amount of one or more of the compounds according to the present invention; and
b) one or more pharmaceutically acceptable excipients.

A further aspect of the present invention relates to methods for controlling one or more inflammatory cytokine mediated or inflammatory cytokine modulated mammalian diseases or conditions, said method comprising the step of administering to a human or higher mammal and effective amount of a composition comprising one or more of the compounds according to the present invention.

Another aspect of the present invention relates to forms of the compounds of the present invention, which under normal physiological conditions, will release the compounds as described herein.

These and other objects, features, and advantages will become apparent to those of ordinary skill in the art from a reading of the following detailed description and the appended claims. All percentages, ratios and proportions

DETAILED DESCRIPTION OF THE INVENTION herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

The present invention relates to compounds which are capable of mediating, controlling or otherwise inhibiting the extracellular release of certain cytokines, especially inflammatory cytokines, said cytokines playing a role in the stimulation, cause or manifestation of a wide variety of diseases, disease states, or syndromes.

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include pentyl, 3-ethyloctanyl, 1,3-dimethylphenyl, cyclohexyl, cis-3-hexyl, 7,7-dimethylbicyclo[2.2.1]-heptan-1-yl, and naphth-2-yl.

Included within the definition of "hydrocarbyl" are the aromatic (aryl) and non-aromatic carbocyclic rings, non-limiting examples of which include cyclopropyl, cyclobutanyl, cyclopentanyl, cyclohexane, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

The term "heterocycle" includes both aromatic (heteroaryl) and non-aromatic heterocyclic (heterocyclic) rings non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

An example of a unit defined by the term "alkylenearyl" is a benzyl unit having the formula:

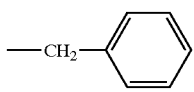

whereas an example of a unit defined by the term "alkyleneheteroaryl" is a 2-picolyl unit having the formula:

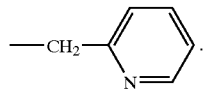

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. An epoxide unit is an example of a substituted unit which requires replacement of a hydrogen atom on adjacent carbons. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit." The following are non-limiting examples of units which can serve as a replacement for hydrogen atoms when a hydrocarbyl unit is described as "substituted."

i) $-[C(R^{13})_2]_p(CH=CH)_qR^{13}$;
ii) $-[C(R^{13})_2]_pC(Z)R^{13}$;
iii) $-[C(R^{13})_2]_pC(Z)_2R^{13}$;
iv) $-[C(R^{13})_2]_pC(Z)CH=CH_2$;
v) $-[C(R^{13})_2]_pC(Z)N(R^{13})_2$;
vi) $-[C(R^{13})_2]_pC(Z)NR^{13}N(R^{13})_2$;
vii) $-[C(R^{13})_2]_pCN$;
viii) $-[C(R^{13})_2]_pCNO$;
ix) $-[C(R^{13})_2]_pCF_3$, $-[C(R^{13})_2]_pCCl_3$, $-[C(R^{13})_2]_pCBr_3$;
Z) $-[C(R^{13})_2]_pN(R^{13})_2$;
xi) $-[C(R^{13})_2]_pNR^{13}CN$;
xii) $-[C(R^{13})_2]_pNR^{13}C(Z)R^{13}$;
xiii) $-[C(R^{13})_2]_pNR^{13}C(Z)N(R^{13})_2$;
xiv) $-[C(R^{13})_2]_pNHN(R^{13})_2$;
xv) $-[C(R^{13})_2]_pNHOR^{13}$;
xvi) $-[C(R^{13})2]_pNCS$;
xvii) $-[C(R^{13})2]_pNO_2$;
xviii) $-[C(R^3)_2]_pOR^{13}$;
xix) $-[C(R^{13})_2]_pOCN$;
xx) $-[C(R^{13})_2]_pOCF_3$, $-[C(R^{13})_2]_pOCCl_3$, $-[C(R^{13})_2]_pOCBr_3$;
xxi) $-[C(R^{13})_2]_pF$, $-[C(R^{13})_2]_pCl$, $-[C(R^{13})_2]_pBr$, $-[C(R^{13})_2]_pI$, and mixtures thereof;
xxii) $-[C(R^{13})_2]_pSCN$;
xxiii) $-[C(R^{13})_2]_pSO_3M$;
xxiv) $-[C(R^{13})_2]_pOSO_3M$;
xxv) $-[C(R^{13})_2]_pSO_2N(R^{13})_2$;
xxvi) $-[C(R^{13})_2]_pSO_2R^{13}$;

xxvii) —[C(R$^{13}$)$_2$]$_p$P(O)H$_2$;
xxviii) —[C(R$^{13}$)$_2$]$_p$PO$_2$;
xxix) —[C(R$^{13}$)$_2$]$_p$P(O)(OH)$_2$;
xxx) and mixtures thereof;

wherein R$^{13}$ is hydrogen, substituted or unsubstituted C$_1$–C$_{20}$ linear, branched, or cyclic alkyl, C$_6$–C$_{20}$ aryl, C$_7$–C$_{20}$ alkylenearyl, and mixtures thereof; M is hydrogen, or a salt forming cation; Z is =O, =S, =NR$^{13}$, and mixtures thereof; p is from 0 to 12; q is from 0 to 12. Suitable salt forming cations include, sodium, lithium, potassium, calcium, magnesium, ammonium, and the like.

1,2-Dihydrodrvrazol-3-ones

The present invention relates to 1,2-dihydropyrazol-3-ones which inhibit the extracellular release of inflammatory cytokines. The compounds of the present invention comprise three elements. The first is the core 1,2-dihydropyrazol-3-one ring scaffold which can be substituted or unsubstituted as described herein below at the nitrogen atoms that comprise the ring system 1-position and 2-position. The second element is the 5-position pyrimidine ring attached at the 4-position of the pyrimidine ring and further substituted at the pyrimidine ring 2-position by either an ether group or an amino group. The third element is a substituted phenyl group at the ring scaffold 4-position. The following is a description of the compounds comprising the present invention.

R is a substituent at the 2-position of the pyrimidin-4-yl portion of the general scaffold, said R unit is:
a) an ether having the formula —O[CH$_2$]$_n$R$^4$; or
b) an amino unit having the formula —NR$^{5a}$R$^{5b}$;
wherein R$^4$ is substituted or unsubstituted C$_1$–C$_{10}$ linear, branched, or cyclic alkyl; substituted or unsubstituted C$_6$–C$_{10}$ aryl; substituted or unsubstituted C$_1$–C$_{10}$ heterocyclic; or substituted or unsubstituted C$_1$–C$_{10}$ heteroaryl; the index n is from 0 to 5.

The following are the various aspects of R units according to the present invention wherein R is an ether having the formula —O[CH$_2$]$_n$R$^4$. However, the formulator is not limited to the herein exemplified iterations and examples.

A) R units encompassing ethers having the formula —OR$^4$ (the index n equal to 0) and R$^4$ is substituted or unsubstituted aryl.
  i) One iteration of this aspect of R comprises ethers having the formula —OR$^4$ and R$^4$ is substituted or unsubstituted aryl. This iteration includes the following non-limiting example of R: phenoxy, 2-fluorophenoxy, 3-fluorophenoxy, 4-fluorophenoxy, 2,4-difluorophenoxy, 3-trifluoromethylphenoxy, 4-trifluoromethylphenoxy, 2,4-trifluoromethyl phenoxy, and the like.
  ii) Another iteration of this aspect of R comprises ethers having the formula —OR$^4$ and R$^4$ is substituted or unsubstituted aryl. This iteration includes the following non-limiting examples: 2-methylphenoxy, 3-methylphenoxy, 4-methylphenoxy, 2,4-dimethylphenoxy, 2-cyanophenoxy, 3-cyanophenoxy, 4-cyanophenoxy, 4-ethylphenoxy, and the like.
  iii) A further iteration of this aspect of R comprises ethers having the formula —OR$^4$ and R$^4$ is substituted or unsubstituted aryl. This iteration includes the following non-limiting examples: (2-methyoxy) phenoxy, (3-methoxy)phenoxy, (4-methoxy) phenoxy, 3-[(N-acetyl)amino]phenoxy, 3-benzo[1,3] dioxol-5-yl, and the like.

B) R units encompassing ethers having the formula —OR$^4$ (the index n equal to 0) and R$^4$ is substituted or unsubstituted heteroaryl.
  i) A first iteration of this aspect of R comprises ethers having the formula —OR$^4$ and R$^4$ is unsubstituted heteroaryl. This iteration includes the following non-limiting examples: pyrimidin-2-yl, pyrimidin-4-yl, pyridin-2-yl, pyridin-3-yl, pyridin-4-yl, and the like.
  ii) A second iteration of this aspect of R comprises ethers having the formula —OR$^4$ and R$^4$ is substituted heteroaryl. This iteration includes the following non-limiting examples: 2-aminopyrimidin-4-yl, and the like.

C) R units encompassing ethers having the formula —OCH$_2$R$^4$ (the index n equal to 1) and R$^4$ is substituted or unsubstituted aryl.
  i) A first iteration of this aspect of R comprises ethers having the formula —OCH$_2$R$^4$ and R$^4$ is substituted or unsubstituted heteroaryl. This iteration includes the following non-limiting examples: pyrimidin-2-yl, pyrimidin-4-yl, 2-aminopyrimidin-4-yl, 4-aminopyrimidin-6-yl, pyridin-2-yl, pyridin-3-yl, pyridin-4-yl, and the like.
  ii) A second iteration of this aspect of R wherein R is an ether having the formula —OCH$_2$R$^4$ and R$^4$ is substituted or unsubstituted alkyleneheteroaryl-aryl. This iteration includes the following non-limiting examples: pyridin-3-ylethyl, (2-methyl-2-pyridin-3-yl)ethyl, and the like.

D) R units encompassing ethers having the formula —OR$^4$ (the index n equal to 1) and R$^4$ is substituted or unsubstituted C$_1$–C$_4$ alkyl or a C$_3$–C$_{10}$ carbocyclic unit.
  i) A first iteration of this aspect of R is an ether having the formula —OR$^4$ and R$^4$ is unsubstituted C$_1$–C$_4$ linear, branched, or cyclic alkyl. This iteration includes the following non-limiting examples: methyl, ethyl, isopropyl, (S)-1-methypropyl, and the like.
  ii) A second iteration of this aspect of R is an ether having the formula —OR$^4$ and R$^4$ is a substituted C$_1$–C$_4$ linear, branched, or cyclic alkyl. This iteration includes the following non-limiting examples: 2-methoxyethyl, (S)-1-methy-3-methyoxypropyl, and the like.
  iii) A third iteration of this aspect of R is an ether having the formula —OR$^4$ and R$^4$ is a substituted or unsubstituted C$_3$–C$_{10}$ carbocyclic unit. This iteration includes cyclopropyl, cyclopentyl, 2,5-dimethylcyclopentyl, cyclohexyl, and the like.

The following are non-limiting examples of the various aspects of R units according to the present invention wherein R comprises an amino unit having the formula:

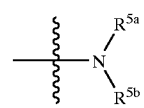

wherein R$^{5a}$ and R$^{5b}$ are each independently:
a) hydrogen; or
b) —[C(R$^{6a}$R$^{6b}$)]$_m$R$^7$;
each R$^{6a}$ and R$^{6b}$ are independently hydrogen, substituted or unsubstituted C$_1$–C$_4$ linear, branched, or cyclic alkyl, —OR$^8$, —N(R$^8$)$_2$, —CO$_2$R$^8$, —CON(R$^8$)$_2$; and mixtures thereof; R$^7$ is hydrogen substituted or unsubstituted $C_1$–$C_6$ linear, branched, or cyclic alkyl, substituted or unsubstituted heterocyclic, substituted or unsubstituted aryl, or substituted or unsubstituted heteroaryl; —$OR^8$, —$N(R^8)_2$, —$CO_2R^8$, —$CON(R^8)_2$; $R^8$ is hydrogen, a water-soluble cation, $C_1$–$C_4$ alkyl, or substituted or unsubstituted aryl; the index m is from 0 to 5. However, the formulator is not limited to the following exemplified iterations and examples.

A) R units encompassing racemic amino groups wherein $R^{5a}$ is hydrogen, $R^{6a}$ or $R^{6b}$ is hydrogen or $C_1$–$C_4$ alkyl, and $R^7$ is substituted or unsubstituted aryl or heteroaryl, said units having the formula:

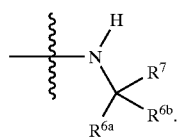

i) A first iteration of this aspect includes units wherein both $R^{6a}$ and $R^{6b}$ are each hydrogen and $R^7$ is aryl or substituted aryl, said units having the formula:

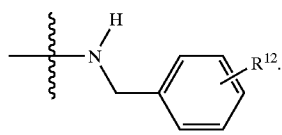

Non-limiting examples of this iteration include benzylamino, (4-fluorobenzyl)amino, (2-aminobenzyl)amino, (2-methylbenzyl)amino, (4-methylbenzyl)amino, (4-methoxybenzyl)amino, (4-methanesulfonyl)benzylamino, and (4-propanesulfonyl)benzylamino.

ii) A second iteration of this aspect includes units wherein one unit of $R^{6a}$ and $R^{6b}$ is hydrogen and the other is methyl, $R^7$ is aryl or substituted aryl, said unit having the formula:

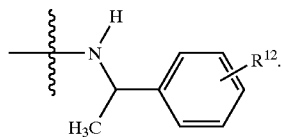

Non-limiting examples of this iteration include (α)-methylbenzylamino, and 1-(4-fluorophenyl)-ethylamino.

iii) A third iteration of this aspect includes units wherein both $R^{6a}$ and $R^{6b}$ are each hydrogen and $R^7$ is heteroaryl or substituted heteroaryl. Non-limiting examples of this iteration include (pyridin-2-yl)methylamino, (pyridin-3-yl)methylamino, (pyridin-4-yl)methylamino, and (imidazol-2-yl)methylamino.

B) R units encompassing racemic amino groups wherein $R^{5a}$ is hydrogen, $R^{6a}$ or $R^{6b}$ is hydrogen or $C_1$–$C_4$ alkyl, and $R^7$ is substituted or unsubstituted $C_1$–$C_6$ linear, branched, or cyclic alkyl, said units having the formula:

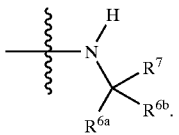

i) A first iteration of this aspect includes units wherein both $R^{6a}$ and $R^{6b}$ are each hydrogen and $R^7$ is hydrogen or $C_1$–$C_6$ linear, branched, or cyclic alkyl.

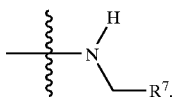

Non-limiting examples of this iteration include methylamino, ethylamino, propylamino, isobutylamino, and cyclopropylmethylamino.

ii) A second iteration of this aspect includes units wherein one unit of $R^{6a}$ and $R^{6b}$ is hydrogen and the other is methyl, and $R^7$ is hydrogen or $C_1$–$C_6$ linear, branched, or cyclic alkyl.

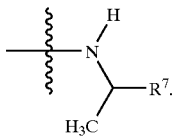

Non-limiting examples of this iteration include isopropylamino, and sec-butylamino.

iii) A third iteration of this aspect includes units wherein both $R^{6a}$ and $R^{6b}$ are each hydrogen and $R^7$ is substituted $C_1$–$C_6$ linear, branched, or cyclic alkyl. Non-limiting examples of this iteration include 2-methoxyethylamino, and 2-methoxy-2-methylpropylamino.

iv) A fourth iteration of this aspect includes units wherein one unit of $R^{6a}$ and $R^{6b}$ is hydrogen and the other is methyl, and $R^7$ is substituted $C_1$–$C_6$ linear, branched, or cyclic alkyl. Non-limiting examples of this iteration include 1-methyl-2-methoxyethylamino, and 1,2-dimethyl-2-methoxyethylamino.

C) R units encompassing racemic amino groups wherein $R^{5a}$ is hydrogen, $R^{6a}$ or $R^{6b}$ is hydrogen or —$CO_2R^8$; $R^8$ is hydrogen or methyl; and $R^7$ is hydrogen or substituted or unsubstituted $C_1$–$C_6$ linear, branched, or cyclic alkyl, substituted or unsubstituted heterocyclic, substituted or unsubstituted aryl, or substituted or unsubstituted heteroaryl; said units having the formula:

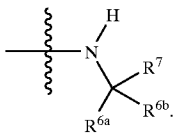

i) A first iteration of this aspect includes units which are derived from alkyl unit comprising amino acids and amino acid methyl esters. Non-limiting examples of this iteration include carboxymethylamino (from glycine), (carboxymethyl)methylamino (from glycine methylester), and 1-(carboxy)ethylamino (from alanine).

ii) A second iteration of this aspect includes units which are derived from substituted or unsubstituted aryl unit comprising amino acids and amino acid methyl esters. Non-limiting examples include (α)-carboxybenzylamino (from phenylalanine) and 1-carboxy-2-(4-hydroxyphenyl)ethylamino (from tyrosine).

D) R units encompassing chiral amino groups wherein $R^{5a}$ is hydrogen, $R^{6a}$ is hydrogen, $R^{6b}$ is $C_1$–$C_4$ alkyl, and $R^7$ is substituted or unsubstituted aryl or heteroaryl, said units having the formula:

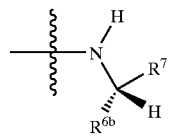

with the indicated stereochemistry.

i) A first iteration of this aspect includes units wherein $R^{6b}$ is methyl, $R^7$ is aryl or substituted aryl. Non-limiting examples of this iteration include (S)-(α)-methylbenzylamino, (S)-1-methyl-1-(4-fluorophenyl)methylamino, (S)-1-methyl-1-(2-aminophenyl)methylamino, (S)-1-methyl-1-(2-methylphenyl)methylamino, (S)-1-methyl-1-(4-methylphenyl)methylamino, and (S)-i-methyl-1-(4-methoxyphenyl)-methylamino.

ii) A second iteration of this aspect includes units wherein $R^{6b}$ is ethyl or hydroxyethyl, $R^7$ is aryl or substituted aryl. Non-limiting examples of this iteration include (S)-(α)-ethylbenzylamino, (S)-1-(4-fluorophenyl)ethylamino, (S)-1-(2-aminophenyl)-ethylamino, (S)-1-ethyl-1-(2-methylphenyl)amino, (S)-1-(4-methylphenyl)-ethylamino, (S)-1-(4-methoxyphenyl)ethylamino, and (S)-1-(4-fluorophenyl)-2-hydroxyethylamino.

E) R units encompassing chiral amino groups wherein $R^{5a}$ is hydrogen, $R^{6a}$ is hydrogen, $R^{6b}$ is $C_1$–$C_4$ alkyl, and $R^7$ is substituted or unsubstituted $C_1$–$C_6$ linear, branched, or cyclic alkyl, said units having the formula:

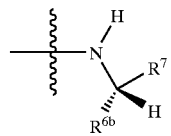

with the indicated stereochemistry.

i) A first iteration of this aspect includes units wherein $R^{6b}$ is methyl and $R^7$ is $C_1$–$C_6$ linear, branched, or cyclic alkyl. Non-limiting examples of this iteration include (S)-1-methylpropylamino, (S)-1-methyl-1-methoxyethylamino, (S)-1-methyl-2-(S)-methoxypropylamino, (S)-1,2-dimethyl-2-hydroxypropylamino, and (S)-1,2-methyl-2-methoxypropylamino.

ii) A second iteration of this aspect includes units wherein $R^{6b}$ is $C_2$–$C_4$ alkyl and $R^7$ is $C_1$–$C_6$ linear, branched, or cyclic alkyl. Non-limiting examples of this iteration include (S)-1-ethylpropylamino, (S)-1-ethyl-1-methoxyethylamino, (S)-1-ethyl-2-(S)-methoxypropylamino, and (S)-1-ethyl-2-methyl-2-methoxypropylamino.

F) R units encompassing chiral amino groups wherein $R^{5a}$ is hydrogen, $R^{6a}$ or $R^{6b}$ is hydrogen or —$CO_2R^8$; $R^8$ is hydrogen or methyl; and $R^7$ is hydrogen or substituted or unsubstituted $C_1$–$C_6$ linear, branched, or cyclic alkyl, substituted or unsubstituted heterocyclic, substituted or unsubstituted aryl, or substituted or unsubstituted heteroaryl; said units having the formula:

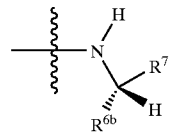

with the indicated stereochemistry.

i) A first iteration of this aspect includes R units which are derived from aryl unit comprising amino acids and amino acid methyl esters, said units having the formula:

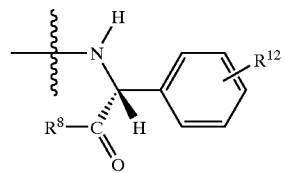

wherein $R^8$ is hydrogen or methyl. Non-limiting examples include (S)-(α)-carboxybenzylamino (R unit derived from L-phenylglycine).

ii) A second iteration of this aspect includes units which are derived from substituted or unsubstituted alkyl unit comprising amino acids and amino acid methyl esters. Non-limiting examples of this iteration include 1-(S)-(carboxy)ethylamino (from L-alanine).

$R^1$ is substituted phenyl. The units may be substituted by any "substituent" group described herein above.

The first aspect of $R^1$ units relates to halogen substituted phenyl, for example, 4-fluorophenyl 2,4-difluorophenyl, 4-chlorophenyl, and the like. A second aspect relates to methyl substituted phenyl, for example, 3-methylphenyl and 4-methylphenyl. A third aspect relates to trifluoromethyl ring substituents, non-limiting examples of which include 3-trifluoromethylphenyl.

Each $R^2$ and $R^3$ unit is independently selected from:
a) hydrogen; and
b) substituted or unsubstituted $C_1$–$C_{10}$ hydrocarbyl selected from:
   i) $C_1$–$C_{10}$ linear, branched or cyclic alkyl;
   ii) $C_1$–$C_{10}$ aryl;
   iii) $C_1$–$C_{10}$ heterocyclic;
   iv) $C_1$–$C_{10}$ heteroaryl.

Among the definitions of cyclic alkyl, aryl, heterocyclic, and heteroaryl as it relates to the $R^2$ and $R^3$ units of the present invention, are included rings formed from functional groups and rings attached to the 1,2-dihydropyrazol-3-one ring scaffold by a tether. The tether is typically one or more alkylene units. These units include:
a) —$(CH_2)_jR^9$;
b) —$(CH_2)_jNR^{10a}R^{10b}$;
c) —$(CH_2)_jCON(R^{11})_2$;
d) —$(CH_2)_jOCON(R^{11})_2$;
e) and mixtures thereof;

wherein $R^9$ is a cyclic ether unit, inter alia, pyranyl and furanyl; $R^{10a}$ and $R^{10b}$ or two $R^{11}$ units are taken together to form a heterocyclic or heteroaryl unit comprising from 3 to 7 atoms; j is an index from 0 to 5, n is an index from 0 to 5.

The first aspect of $R^2$ and $R^3$ relates to 1,2-dihydropyrazol-3-one ring scaffolds wherein both $R^2$ and $R^3$ are each hydrogen. One iteration includes the generic compounds encompassed by 4-($R^1$)-5-[2-R-pyrimidin-4-yl]-1,2-dihydro-pyrazol-3-one.

The second aspect of $R^2$ and $R^3$ relates to 1,2-dihydropyrazol-3-one ring scaffolds wherein $R^2$ is a substituted or unsubstituted heterocyclic ring and $R^3$ is a substituted or unsubstituted $C_1$–$C_6$ linear, branched, or cyclic alkyl unit. One iteration includes the generic compounds encompassed by 1-(piperidin-4-yl)-2-methyl-4-($R^1$)-5-[2-R-pyrimidin-4-yl]-1,2-dihydro-pyrazol-3-one.

The third aspect of $R^2$ and $R^3$ relates to 1,2-dihydropyrazol-3-one ring scaffolds wherein $R^2$ is a substituted or unsubstituted $C_1$–$C_6$ linear, branched, or cyclic alkyl unit and $R^3$ is a substituted or unsubstituted heterocyclic ring. One iteration includes the generic compounds encompassed by 1-methyl-2-(piperidin-4-yl)-4-($R^1$)-5-[2-R-pyrimidin-4-yl]-1,2-dihydro-pyrazol-3-one.

Non-limiting examples of the second and third aspects of $R^2$ and $R^3$ units encompass the substituted and unsubstituted rings, inter alia, scaffolds having the formula:

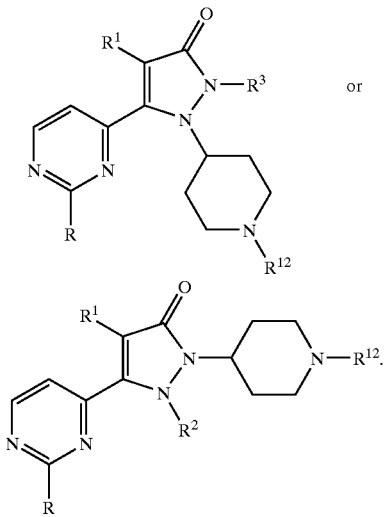 or and $R^{12}$ is —[C($R^{13}$)$_2$]$_p$C(O)$_2$R$^{13}$, non-limiting examples of which include —(CH$_2$)CO$_2$H, —(CH$_2$)CO$_2$CH$_3$, —[CH(CH$_3$)]CO$_2$H, —[CH(CH$_3$)]CO$_2$CH$_3$, —[C(CH$_3$)$_2$]CO$_2$H, —[C(CH$_3$)$_2$]CO$_2$CH$_3$, or the water soluble salts of the acids.

The fourth aspect of $R^2$ and $R^3$ relates to 1,2-dihydropyrazol-3-one ring scaffolds wherein $R^2$ and $R^3$ are each independently $C_1$–$C_6$ alkyl. One iteration of this aspect relates to rings wherein $R^2$ and $R^3$ units are the same, interalia, the generic compounds 1,2-dimethyl-4-($R^1$)-5-[2-R-pyrimidin-4-yl]-1,2-dihydro-pyrazol-3-one and 1,2-diethyl-4-($R^1$)-5-[2-R-pyrimidin-4-yl]-1,2-dihydro-pyrazol-3-one.

However, other non-exemplified aspects include compounds, inter alia, under the generic formulae 1-substituted aryl-2-(piperidin-4-yl)-4-($R^1$)-5-[2-R-pyrimidin-4-yl]-1,2-dihydro-pyrazol-3-one, 1-(morpholin-4-yl)-2-(heteroaryl)-4-($R^1$)-5-[2-R-pyrimidin-4-yl]-1,2-dihydro-pyrazol-3-one, and 1-heteroaryl-2-substitued aryl-4-($R^1$)-5-[2-R-pyrimidin-4-yl]-1,2-dihydro-pyrazol-3-one.

Selection of $R^2$ and $R^3$ units and combinations thereof directly relate to the Categories described herein below. For example, compounds wherein both $R^2$ and $R^3$ are each methyl, ethyl, or other lower alkyl, relates to Category IV analogs.

The analogs (compounds) of the present invention are arranged in several categories to assist the formulator in applying a rational synthetic strategy for the preparation of analogs which are not expressly exampled herein. The arrangement into categories does not imply increased or decreased efficacy for any of the compositions of matter described herein.

The analogs (compounds) of the present invention are conveniently obtained in the salt form, for example, the trifluoroacetate salt, especially after removal of protecting groups with trifluoroacetic acid as the last step in their preparation. However, the formulator may neutralize the analogs, or convert them to another salt form without change to the efficacy of the parent compounds. Also, the formulator, if convenient or practicable, will prepare a pro-drug which will release the active compound (analog) upon uptake by the host. All of these variations are encompassed within the present invention.

The first category of inflammatory cytokine release inhibiting compounds according to the present invention are 4-$R^1$-substituted-5-(2-R-substituted-pyrimidin-4-yl)-1,2-dihydropyrazol-3-ones having the general scaffold with the formula:

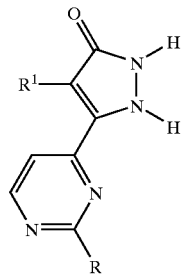

wherein the first aspect of Category I has the formula:

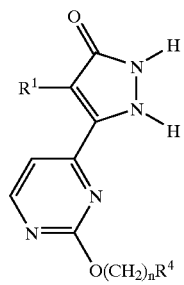

$R^1$ and $R^4$ are described herein below in Table I. The index n can be 0 or 1.

TABLE I

| No. | $R^1$ | $R^4$ |
|---|---|---|
| 1 | 4-fluorophenyl | phenyl |
| 2 | 4-fluorophenyl | 2-fluorophenyl |
| 3 | 4-fluorophenyl | 3-fluorophenyl |
| 4 | 4-fluorophenyl | 4-fluorophenyl |
| 5 | 4-fluorophenyl | 2,6-difluorophenyl |
| 6 | 4-fluorophenyl | 2-cyanophenyl |
| 7 | 4-fluorophenyl | 3-cyanophenyl |
| 8 | 4-fluorophenyl | 2-trifluoromethylphenyl |
| 9 | 4-fluorophenyl | 4-trifluoromethylphenyl |
| 10 | 4-fluorophenyl | N-methylpiperadin-4-yl |
| 11 | 4-fluorophenyl | 4-methylphenyl |

TABLE I-continued

| No. | R¹ | R⁴ |
|---|---|---|
| 12 | 4-fluorophenyl | 2,4-dimethylphenyl |
| 13 | 4-fluorophenyl | 3-N-acetylaminophenyl |
| 14 | 4-fluorophenyl | pyran-4-yl |
| 15 | 4-fluorophenyl | 4-methoxyphenyl |
| 16 | 4-fluorophenyl | 3-benzo[1,3]dioxol-5-yl |
| 17 | 2,4-difluorophenyl | phenyl |
| 18 | 2,4-difluorophenyl | 2-fluorophenyl |
| 19 | 2,4-difluorophenyl | 3-fluorophenyl |
| 20 | 2,4-difluorophenyl | 4-fluorophenyl |
| 21 | 2,4-difluorophenyl | 2,6-difluorophenyl |
| 22 | 2,4-difluorophenyl | 2-cyanophenyl |
| 23 | 2,4-difluorophenyl | 3-cyanophenyl |
| 24 | 2,4-difluorophenyl | 2-trifluoromethylphenyl |
| 25 | 2,4-difluorophenyl | 4-trifluoromethylphenyl |
| 26 | 2,4-difluorophenyl | N-methylpiperadin-4-yl |
| 27 | 2,4-difluorophenyl | 4-methylphenyl |
| 28 | 2,4-difluorophenyl | 2,4-dimethylphenyl |
| 29 | 2,4-difluorophenyl | 3-N-acetylaminophenyl |
| 30 | 2,4-difluorophenyl | pyran-4-yl |
| 31 | 2,4-difluorophenyl | 4-methoxyphenyl |
| 32 | 2,4-difluorophenyl | 3-benzo[1,3]dioxol-5-yl |
| 33 | 3-trifluoromethylphenyl | phenyl |
| 34 | 3-trifluoromethylphenyl | 2-fluorophenyl |
| 35 | 3-trifluoromethylphenyl | 3-fluorophenyl |
| 36 | 3-trifluoromethylphenyl | 4-fluorophenyl |
| 37 | 3-trifluoromethylphenyl | 2,6-difluorophenyl |
| 38 | 3-trifluoromethylphenyl | 2-cyanophenyl |
| 39 | 3-trifluoromethylphenyl | 3-cyanophenyl |
| 40 | 3-trifluoromethylphenyl | 2-trifluoromethylphenyl |
| 41 | 3-trifluoromethylphenyl | 4-trifluoromethylphenyl |
| 42 | 3-trifluoromethylphenyl | N-methylpiperadin-4-yl |
| 43 | 3-trifluoromethylphenyl | 4-methylphenyl |
| 44 | 3-trifluoromethylphenyl | 2,4-dimethylphenyl |
| 45 | 3-trifluoromethylphenyl | 3-N-acetylaminophenyl |
| 46 | 3-trifluoromethylphenyl | pyran-4-yl |
| 47 | 3-trifluoromethylphenyl | 4-methoxyphenyl |
| 48 | 3-trifluoromethylphenyl | 3-benzo[1,3]dioxol-5-yl |

The analogs 1–48 are non-limiting examples of analogs which comprise the first aspect of Category I. The analogs of the first aspect of Category I can be suitably prepared by the procedure outlined herein below. In the following example, $R^1$ is 4-fluorophenyl, however, the formulator may suitably substitute any starting material compatible with this procedure, inter alia, methyl phenylacetate, methyl 4-chlorophenylacetate, and methyl 3-(trifluoromethyl) phenylacetate.

Scheme I: Preparation of First Aspect of Category I

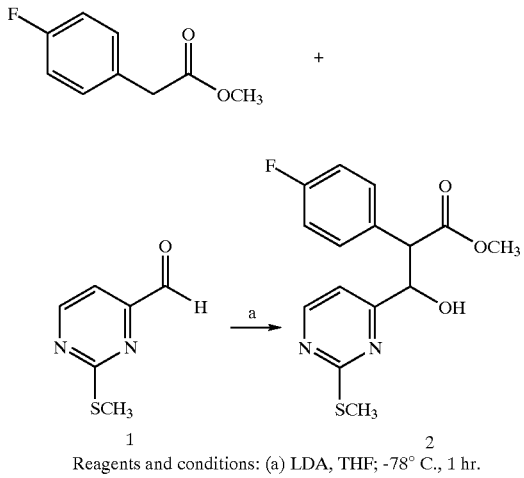

Reagents and conditions: (a) LDA, THF; -78° C., 1 hr.

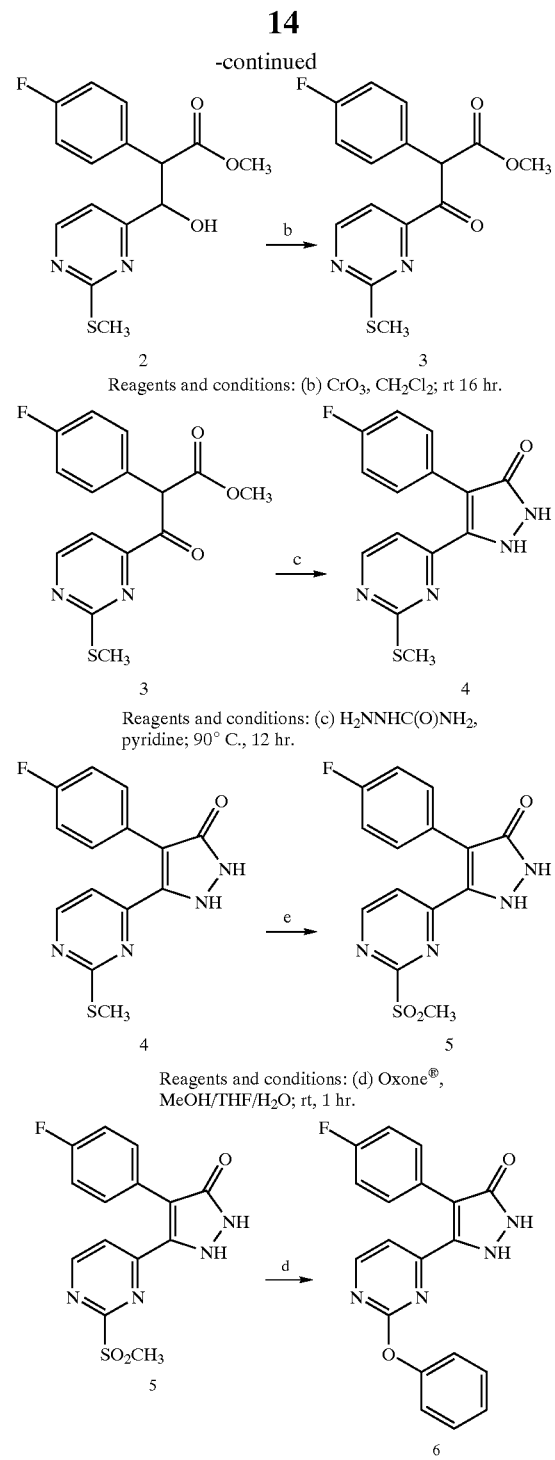

Reagents and conditions: (b) CrO₃, CH₂Cl₂; rt 16 hr.

Reagents and conditions: (c) H₂NNHC(O)NH₂, pyridine; 90° C., 12 hr.

Reagents and conditions: (d) Oxone®, MeOH/THF/H₂O; rt, 1 hr.

Reagents and conditions: (e) phenol, NaH, THF, 1.5 hr rt.

EXAMPLE 1

4-(4-Fluorophenyl)-5-[2-(phenoxy)pyrimidin-4-yl]-1,2dihydropyrazol-3-one (6)

The following is a procedure for the preparation of 2-methylsulfanyl-pyrimidine-4-carbaldehyde, 1, adapted from the procedure of H. Bredereck et al., *Chem. Ber.*, 97, pp 3407–3417 (1964) included herein by reference.

To a 12 L 3-neck flask under inert atmosphere is charged N,N-dimethyl-formamide dimethyl acetyl (801 g) and pyruvic aldehyde dimethyl acetal (779 g). The mixture is heated to reflux for 18 hours during which time the temperature decreases from about 109° C. to about 80° C. The solution is cooled and methanol (4 L) is added to dissolve the crude residue. The solution is then cooled to 20° C. and thiourea (892 g, 11.7 mol) is added. After allowing the mixture to stir about 15 minutes, sodium methoxide (741 g, 13.7 mol) is added in 4 equal portions over 1 hour while maintaining the solution temperature in the range of 18–28° C. The mixture is stirred for 5 hours at room temperature, cooled to 20° C., then methyl iodide (2 kg) is added over 1.25 hours while maintaining the reaction temperature in the range of 17–29° C. Stirring is continued for 18 hours at room temperature. The methanol and unreacted methyl iodide is removed by heating the solution at 35° C. @40 torr to produce about 4.46 kg of a dark residue which is partitioned between 14 L of water and 5 L of ethyl acetate. The water fraction is extracted a second time with ethyl acetate, the organic layers combined and concentrated in vacuo too afford 685 g of an oil which is purified over silica to 522 g of 4-dimethoxymethyl-2-methylsulfanyl-pyrimidine.

The dimethyl acetal obtained above is then hydrolyzed to the free aldehyde by heating to 60° C. for 3 hours in 1 M HCl. Workup for neutral using ethyl acetate to extract the product affords 347 g crude product which is purified over silica to afford 2-methylsulfanyl-pyrimidine-4-carbaldehyde, 1.

Preparation of 2-(4-fluorophenyl)-3-(2-methylsulfanyl-pyrimidin-4-yl)-3-hydroxypropionic acid methyl ester (2): To a cold (−78° C.) solution of lithium diisopropylamide (21.4 mL of 2M solution in THF, 42.8 mmol) in THF (70 mL) is added dropwise a solution of methyl 4-fluorophenyl-acetate (6.0 g, 35.7 mmol) in THF (30 mL). The solution is stirred for 1 hour at −78° C. after which a solution of 2-methylsulfanyl-pyrimidine-4-carbaldehyde, 1, (6.0 g, 39.3 mmol) in THF (30 mL) is added dropwise to the reaction mixture. Stirring is continued for 45 minutes at −78° C. then the reaction is quenched by pouring the reaction solution into aqueous saturated $NH_4Cl$. The aqueous phase is extracted with ethyl acetate. The organic phases combined, dried ($MgSO_4$), filtered, and concentrated in vacuo. The crude residue is purified over silica (33% EtOAc/hexanes) to afford 8.7 g (76%) of the desired product as a mixture (1:1) of diastereomers. $^1H$ NMR (300 MHz, $CDCl_3$) δ 8.52 (dd, J=4.5, 1.5 Hz, 2H), 7.21–7.15 (m, 4H), 6.99 (t, J=9.0 Hz, 2H), 5.38 (d, J=5.4 Hz, 1H), 3.83 (d, J=5.4 Hz, 1H), 3.67 (s, 3H); ESI/MS: 276.1 (M+H).

Preparation of 2-(4-fluorophenyl)-3-(2-methylsulfanyl-pyrrimidin-4-yl)-3-oxo-propionic acid methyl ester (3): To a suspension of $CrO_3$ in $CH_2Cl_2$ (300 mL) is added pyridine. The mixture is stirred vigorously for 1 hour at room temp. A solution of the crude 2-(4-fluorophenyl)-3-(2-methylsulfanyl-pyrimidin-4-yl)-3-hydroxypropionic acid methyl ester, 2, prepared above in $CH_2Cl_2$ (50 mL) is added dropwise to the chromium suspension. The reaction mixture is stirred at room temperature for 16 hours, diluted with ether (1 L) and filtered through a pad of Celite. The filtrate is concentrated in vacuo and the resulting residue is purified over silica (25% EtOAc/hexanes) to afford 3.7 g (43% yield) of the desired product as a yellow solid. $^1H$ NMR (300 MHz, $CDCl_3$) δ 8.79 (d, J=4.8 Hz, 1H), 7.59 (d, J=4.8 Hz, 1H), 7.40 (dd, J=8.7, 5.4 Hz, 2H), 7.10 (t, J=8.7 Hz, 2H), 5.97 (s, 1H), 3.79 (s, 3H), 2.63 (s, 3H); ESI/MS: 321.0 (M+H).

Preparation of 4-(4-fluorophenyl)-5-(2-methylsulfanylpyrimidin-4-yl)-1,2-dihydro-pyrazol-3-one (4): A solution of 2-(4-fluorophenyl)-3-(2-methylsulfanyl-pyrimidin-4-yl)-3-oxo-propionic acid methyl ester, 3, (1 g, 3.7 mmol), semicarbazide HCl (0.653 g, 5.8 mmol) and pyridine (10 mL) is heated at 90° C. for 12 hours. The solution is then concentrated in vacuo to afford a semi-solid residue which is taken up in methanol and the resulting solid removed by filtration. The filtrate is concentrated in vacuo to afford the desired compound as a white solid, which is used without further purification.

Preparation of 4-(4-fluorophenyl)-5-(2-methanesulfonylpyrimidin-4-yl)-1,2-dihydro-pyrazol-3-one (5): To a solution of 4-(4-fluorophenyl)-5-(2-methylsulfanylpyrimidin-4-yl)-1,2-dihydro-pyrazol-3-one, 4, (3.0 g, 10 mmol) in THF:methanol (100 mL of a 1:1 mixture) is added dropwise a solution of Oxone® (potassium peroxymonosulfate) (24.6 g, 40 mmol) in water (100 mL). The reaction is stirred 1 hour at room temperature, diluted with aqueous $NaHCO_3$ and extract three times with ethyl acetate. The organic layers are combined, dried, and concentrated in vacuo to afford the crude desired product which is used without further purification.

Preparation of 4-(4-fluorophenyl)-5-[2-(phenoxy)pyrimidin-4-yl]-1,2dihydropyrazol-3-one (6): To a solution of phenol (0.66 g, 7.08 mmol) in THF (5 mL) is added NaH (0.24 g, 5.91 mmol) followed by a solution of the crude 4-(4-fluorophenyl)-5-(2-methanesulfonylpyrimidin-4-yl)-1,2-dihydro-pyrazol-3-one, 5, prepared herein above (0.22 g, 0.67 mmol) in THF (2 mL). The reaction mixture is stirred for 1.5 hours at room temperature, diluted with aqueous $NaHCO_3$ and extracted with twice with ethyl acetate. The organic layers are combined, dried over $MgSO_4$, and concentrated in vacuo to afford the crude product which is purified over silica (100% EtOAc, followed by 10% MeOH/EtOAc) to provide the desired product as a yellow solid.

The following are non-limiting examples of compounds from the first aspect of Category I can be prepared by the procedure described herein above.

5-(2-Phenoxypyrimidin-4-yl)-4-(4-fluorophenyl)-1,2-dihydropyrazol-3-one;

5-[2-(2-Hydroxyphenoxy)pyrimidin-4-yl]-4-(4-fluorophenyl)-1,2-dihydropyrazol-3-one;

5-[2-(4-Hydroxyphenoxy)pyrimidin-4-yl]-4-(4-fluorophenyl)-1,2-dihydropyrazol-3-one;

5-[2-(2-N-Acetylphenoxy)pyrimidin-4-yl]-4-(4-fluorophenyl)-1,2-dihydropyrazol-3-one;

5-[2-(3-N-Acetylphenoxy)pyrimidin-4-yl]-4-(4-fluorophenyl)-1,2-dihydropyrazol-3-one;

5-[2-(2-Cyanophenoxy)pyrimidin-4-yl]-4-(4-fluorophenyl)-1,2-dihydropyrazol-3-one;

5-[2-(2-Fluorophenoxy)pyrimidin-4-yl]-4-(4-fluorophenyl)-1,2-dihydropyrazol-3-one;

5-[2-(4-Fluorophenoxy)pyrimidin-4-yl]-4-(4-fluorophenyl)-1,2-dihydropyrazol-3-one;

5-(2-Benzoxypyrimidin-4-yl)-4-(4-fluorophenyl)-1,2-dihydropyrazol-3-one;

5-[2-(S)-(α-methylbenzoxy)pyrimidin-4-yl]-4-(4-fluorophenyl)-1,2-dihydropyrazol-3-one;

5-[2-(R)-(α-methylbenzoxy)pyrimidin-4-yl]-4-(4-fluorophenyl)-1,2-dihydropyrazol-3-one;

A second aspect of the Category I inflammatory cytokine release inhibiting compounds according to the present invention have the general scaffold having the formula:

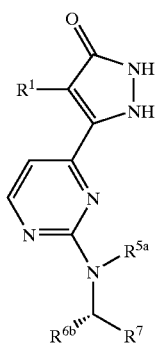

whereinn $R^1$, $R^{5a}$, $R^{6b}$, and $R^7$ are described herein below in Table II. The stereochemistry indicated above is present for the analogs of Table II when $R^{6b}$ or $R^7$ is not hydrogen. However, analogs having the opposite stereochemistry are equally encompassed within the scope of the second aspect of Category II.

TABLE II

| No. | $R^1$ | $R^{5a}$ | $R^{6b}$ | $R^7$ |
|---|---|---|---|---|
| 49 | 4-fluorophenyl | H | H | phenyl |
| 50 | 4-fluorophenyl | H | H | 4-fluorophenyl |
| 51 | 4-fluorophenyl | H | H | 2-aminophenyl |
| 52 | 4-fluorophenyl | H | H | 2-methylphenyl |
| 53 | 4-fluorophenyl | H | H | 4-methylphenyl |
| 54 | 4-fluorophenyl | H | H | 4-methoxyphenyl |
| 55 | 4-fluorophenyl | H | H | 4-(propanesulfonyl)phenyl |
| 56 | 4-fluorophenyl | H | H | 3-benzo[1,3]dioxol-5-yl |
| 57 | 4-fluorophenyl | H | H | pyridin-2-yl |
| 58 | 4-fluorophenyl | H | H | pyridin-3-yl |
| 59 | 4-fluorophenyl | H | methyl | phenyl |
| 60 | 4-fluorophenyl | H | methyl | 4-fluorophenyl |
| 61 | 4-fluorophenyl | H | methyl | 2-aminophenyl |
| 62 | 4-fluorophenyl | H | methyl | 2-methylphenyl |
| 63 | 4-fluorophenyl | H | methyl | 4-methylphenyl |
| 64 | 4-fluorophenyl | H | methyl | 4-methoxyphenyl |
| 65 | 4-fluorophenyl | H | methyl | 4-(propanesulfonyl)phenyl |
| 66 | 4-fluorophenyl | H | methyl | 3-benzo[1,3]dioxol-5-yl |
| 67 | 4-fluorophenyl | H | methyl | pyridin-2-yl |
| 68 | 4-fluorophenyl | H | methyl | pyridin-3-yl |
| 69 | 4-fluorophenyl | H | H | H |
| 70 | 4-fluorophenyl | H | H | methyl |
| 71 | 4-fluorophenyl | H | H | ethyl |
| 72 | 4-fluorophenyl | H | H | vinyl |
| 73 | 4-fluorophenyl | H | H | cyclopropyl |
| 74 | 4-fluorophenyl | H | H | cyclohexyl |
| 75 | 4-fluorophenyl | H | H | methoxymethyl |
| 76 | 4-fluorophenyl | H | H | methoxyethyl |
| 77 | 4-fluorophenyl | H | H | 1-hydroxy-1-methylethyl |
| 78 | 4-fluorophenyl | H | H | —CO$_2$H |
| 79 | 4-fluorophenyl | H | methyl | H |
| 80 | 4-fluorophenyl | H | methyl | methyl |
| 81 | 4-fluorophenyl | H | methyl | ethyl |
| 82 | 4-fluorophenyl | H | methyl | vinyl |
| 83 | 4-fluorophenyl | H | methyl | cyclopropyl |
| 84 | 4-fluorophenyl | H | methyl | cyclohexyl |
| 85 | 4-fluorophenyl | H | methyl | methoxymethyl |
| 86 | 4-fluorophenyl | H | methyl | methoxyethyl |
| 87 | 4-fluorophenyl | H | methyl | 1-hydroxy-1-methylethyl |
| 88 | 4-fluorophenyl | H | methyl | —CO$_2$H |
| 89 | 3-trifluoromethylphenyl | H | methyl | phenyl |
| 90 | 3-trifluoromethylphenyl | H | methyl | 4-fluorophenyl |
| 91 | 3-trifluoromethylphenyl | H | methyl | 2-aminophenyl |
| 92 | 3-trifluoromethylphenyl | H | methyl | 2-methylphenyl |
| 93 | 3-trifluoromethylphenyl | H | methyl | 4-methylphenyl |
| 94 | 3-trifluoromethylphenyl | H | methyl | 4-methoxyphenyl |
| 95 | 3-trifluoromethylphenyl | H | methyl | 4-(propanesulfonyl)phenyl |
| 96 | 3-trifluoromethylphenyl | H | methyl | 3-benzo[1,3]dioxol-5-yl |
| 97 | 3-trifluoromethylphenyl | H | methyl | pyridin-2-yl |
| 98 | 3-trifluoromethylphenyl | H | methyl | pyridin-3-yl |
| 99 | 3-trifluoromethylphenyl | H | methyl | H |
| 100 | 3-trifluoromethylphenyl | H | methyl | methyl |
| 101 | 3-trifluoromethylphenyl | H | methyl | ethyl |
| 102 | 3-trifluoromethylphenyl | H | methyl | vinyl |
| 103 | 3-trifluoromethylphenyl | H | methyl | cyclopropyl |
| 104 | 3-trifluoromethylphenyl | H | methyl | cyclohexyl |
| 105 | 3-trifluoromethylphenyl | H | methyl | methoxymethyl |
| 106 | 3-trifluoromethylphenyl | H | methyl | methoxyethyl |
| 107 | 3-trifluoromethylphenyl | H | methyl | 1-hydroxy-1-methylethyl |
| 108 | 3-trifluoromethylphenyl | H | methyl | —CO$_2$H |

Utilizing intermediates such as compound 5, as a convenient starting point the analogs 49–108 and others encompassed within the description of this category can be suitably prepared by the procedure outlined herein below. In the following example, $R^1$ is 4-fluorophenyl, however, the formulator may suitably substitute any starting material compatible with this procedure, inter alia, methyl phenylacetate, methyl 4-chlorophenyl-acetate, and methyl 3-(trifluoromethyl)phenyl acetate.

Scheme II:
Preparation of Second Aspect of Category I

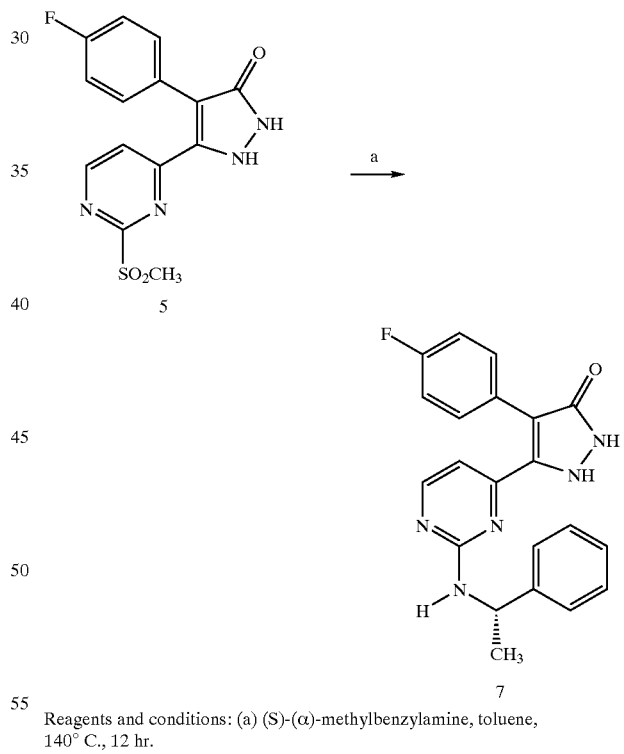

Reagents and conditions: (a) (S)-(α)-methylbenzylamine, toluene, 140° C., 12 hr.

EXAMPLE 2

2-(4-Fluorophenyl)-3-[2-(S)-(1-phenylethylamino)pyrimidin-4-yl]-6,7-dihydro-5H-pyrazolo[1,2-a]pyrazol-1-one (7)

Preparation of 2-(4-fluorophenyl)-3-[2-(S)-(1-phenylethylamino)pyrimidin-4-yl]-6,7-dihydro-5H-pyrazolo[1,2-a]pyrazol-1-one (7): Crude 2-(4- fluorophenyl)-3-(2-methanesulfonyl-pyrimidin-4-yl)-6,7-dihydro-5H-pyrazolo[1,2-a]pyrazol-1-one, 5, prepared herein above (0.86 g, 2.3 mmol) and (S)-(−)-α-methyl-benzyl amine (10.5 mL, 81.6 mmol) is dissolved in toluene (18 mL). The resulting mixture is heated to 140° C. for 12 hours, cooled to room temperature and the solvent removed in vacuo. The resulting residue is purified over silica (1:1 EtOAc/hexanes) to afford the desired product which to analog 59 from Table II. $^1$H NMR (300 MHz, CDCl$_3$) δ 8.18 (d, J=5.1 Hz, 1H), 7.42–7.34 (m, 7H), 7.04 (ddd, J=9.0, 6.9, 2.1 Hz, 2H), 6.39 (d, J=5.1 Hz, 1H), 5.68 (bd s, 1H), 5.10 (m, 1H), 3.97 (dt, J=7.5, 7.5, 7.5 Hz, 2H), 2.45 (bd s, 2H), 1.67 (m, 2H), 1.60 (d, J=7.5 Hz, 3H); HRMS calcd for C$_{24}$H$_{22}$FN$_5$O (M+H)$^+$ 416.1887; found 416.1897.

The second category of inflammatory cytokine release inhibiting compounds according to the present invention are 4-R$^1$-substituted-5-(2-R-substituted-pyrimidin-4-yl)-1,2-dihydropyrazol-3-ones having the general scaffold with the formula:

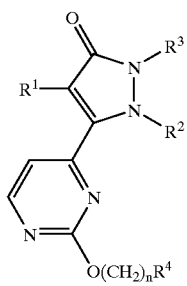

wherein the first aspect of Category II comprises R$^2$ comprising a substituted or unsubstituted ring, R$^3$ comprising a C$_1$–C$_4$ linear, branched, or cyclic alkyl unit, and the index n is 0, as defined in Table III herein below.

TABLE III

| No. | R$^1$ | R$^2$ | R$^3$ | R$^4$ |
|---|---|---|---|---|
| 109 | 4-fluorophenyl | piperidin-4-yl | methyl | phenyl |
| 110 | 4-fluorophenyl | piperidin-4-yl | methyl | 2-hydroxyphenyl |
| 111 | 4-fluorophenyl | piperidin-4-yl | methyl | 4-hydroxyphenyl |
| 112 | 4-fluorophenyl | piperidin-4-yl | methyl | 2-N-acetylaminophenyl |
| 113 | 4-fluorophenyl | piperidin-4-yl | methyl | 3-N-acetylaminophenyl |
| 114 | 4-fluorophenyl | piperidin-4-yl | methyl | 2-cyanophenyl |
| 115 | 4-fluorophenyl | piperidin-4-yl | methyl | 4-fluorophenyl |
| 116 | 4-fluorophenyl | piperidin-4-yl | methyl | benzyl |
| 117 | 4-fluorophenyl | piperidin-4-yl | methyl | (S)-α-methylbenzyl |
| 118 | 4-fluorophenyl | piperidin-4-yl | methyl | (R)-α-methylbenzyl |
| 119 | 4-fluorophenyl | N-methyl-piperidin-4-yl | methyl | phenyl |
| 120 | 4-fluorophenyl | N-methyl-piperidin-4-yl | methyl | 2-hydroxyphenyl |
| 121 | 4-fluorophenyl | N-methyl-piperidin-4-yl | methyl | 4-hydroxyphenyl |
| 122 | 4-fluorophenyl | N-methyl-piperidin-4-yl | methyl | 2-N-acetylaminophenyl |
| 123 | 4-fluorophenyl | N-methyl-piperidin-4-yl | methyl | 3-N-acetylaminophenyl |
| 124 | 4-fluorophenyl | N-methyl-piperidin-4-yl | methyl | 2-cyanophenyl |
| 125 | 4-fluorophenyl | N-methyl-piperidin-4-yl | methyl | 4-fluorophenyl |
| 126 | 4-fluorophenyl | N-methyl-piperidin-4-yl | methyl | benzyl |
| 127 | 4-fluorophenyl | N-methyl-piperidin-4-yl | methyl | (S)-α-methylbenzyl |
| 128 | 4-fluorophenyl | N-methyl-piperidin-4-yl | methyl | (R)-α-methylbenzyl |
| 129 | 4-fluorophenyl | morpholin-4-yl | methyl | phenyl |
| 130 | 4-fluorophenyl | morpholin-4-yl | methyl | 2-hydroxyphenyl |
| 131 | 4-fluorophenyl | morpholin-4-yl | methyl | 4-hydroxyphenyl |
| 132 | 4-fluorophenyl | morpholin-4-yl | methyl | 2-N-acetylaminophenyl |
| 133 | 4-fluorophenyl | morpholin-4-yl | methyl | 3-N-acetylaminophenyl |
| 134 | 4-fluorophenyl | morpholin-4-yl | methyl | 2-cyanophenyl |
| 135 | 4-fluorophenyl | morpholin-4-yl | methyl | 4-fluorophenyl |
| 136 | 4-fluorophenyl | morpholin-4-yl | methyl | benzyl |
| 137 | 4-fluorophenyl | morpholin-4-yl | methyl | (S)-α-methylbenzyl |
| 138 | 4-fluorophenyl | morpholin-4-yl | methyl | (R)-α-methylbenzyl |
| 139 | 4-fluorophenyl | N-acetyl-piperidin-4-yl | methyl | phenyl |
| 140 | 4-fluorophenyl | N-acetyl-piperidin-4-yl | methyl | 2-hydroxyphenyl |
| 141 | 4-fluorophenyl | N-acetyl-piperidin-4-yl | methyl | 4-hydroxyphenyl |
| 142 | 4-fluorophenyl | N-acetyl-piperidin-4-yl | methyl | 2-N-acetylaminophenyl |
| 143 | 4-fluorophenyl | N-acetyl-piperidin-4-yl | methyl | 3-N-acetylaminophenyl |
| 144 | 4-fluorophenyl | N-acetyl-piperidin-4-yl | methyl | 2-cyanophenyl |
| 145 | 4-fluorophenyl | N-acetyl-piperidin-4-yl | methyl | 4-fluorophenyl |
| 146 | 4-fluorophenyl | N-acetyl-piperidin-4-yl | methyl | benzyl |
| 147 | 4-fluorophenyl | N-acetyl-piperidin-4-yl | methyl | (S)-α-methylbenzyl |
| 148 | 4-fluorophenyl | N-acetyl-piperidin-4-yl | methyl | (R)-α-methylbenzyl |

The following is an example of the preparation of compounds encompassed within the first aspect of Category II analogs according to the present invention.

Scheme III:
Preparation of First Aspect of Category II

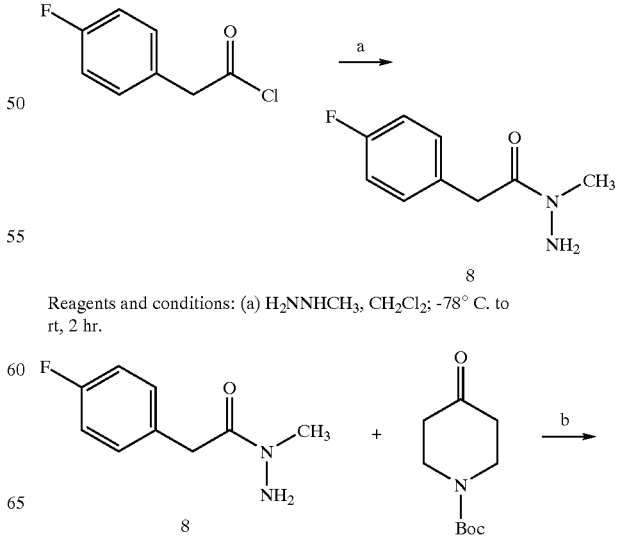

Reagents and conditions: (a) H$_2$NNHCH$_3$, CH$_2$Cl$_2$; −78° C. to rt, 2 hr.

-continued
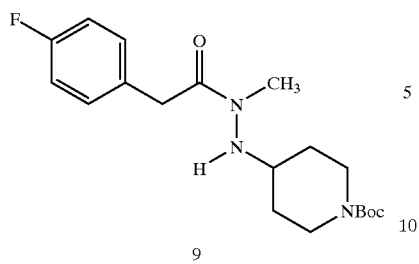
9
Reagents and conditions: (b) i) reflux 0.5 hr; ii) NaCNBH₃, HCl EtOH; rt, 3 hr.
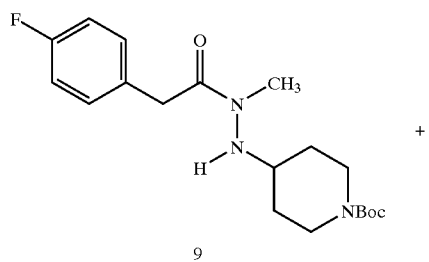
9
+
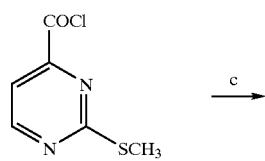
10
→ c
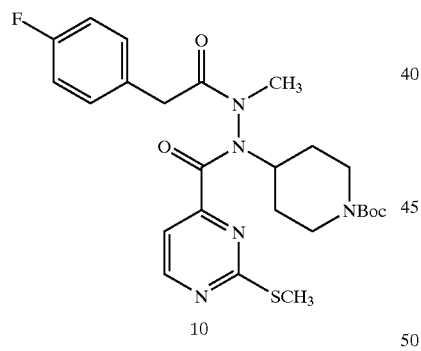
10
Reagents and conditions: (c) pyridine; rt, 2 hr.
→ d
-continued
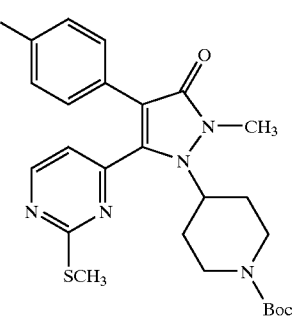
11
Reagents and conditions: (d) NaH, DMF; 0° C., 1 hr.
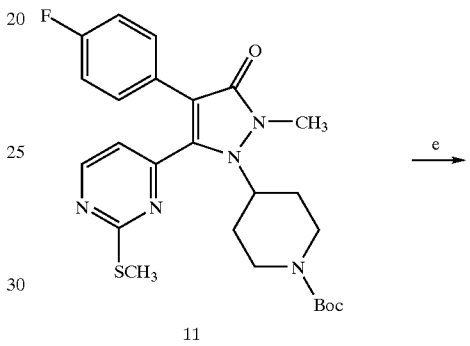
11
→ e
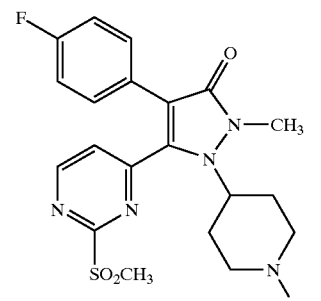
12
Reagents and conditions: (e) m-CPBA, CHCl₃; 0° C., 5 min.
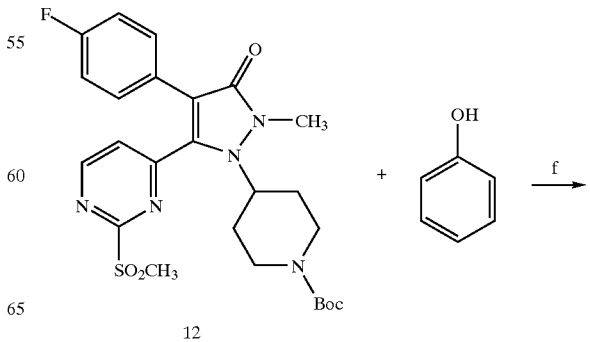
12
+ 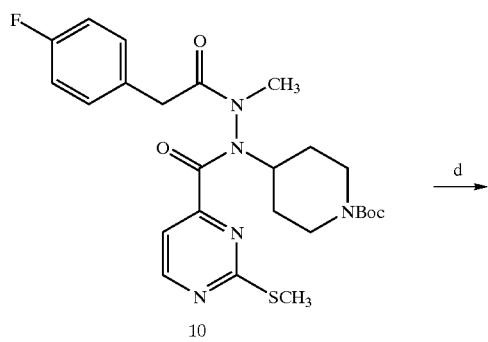 → f

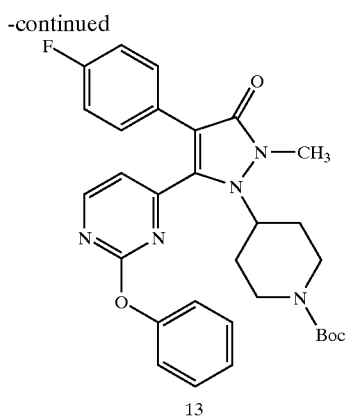

13

Reagents and conditions: (f) NaH, THF; rt, 14 hr.

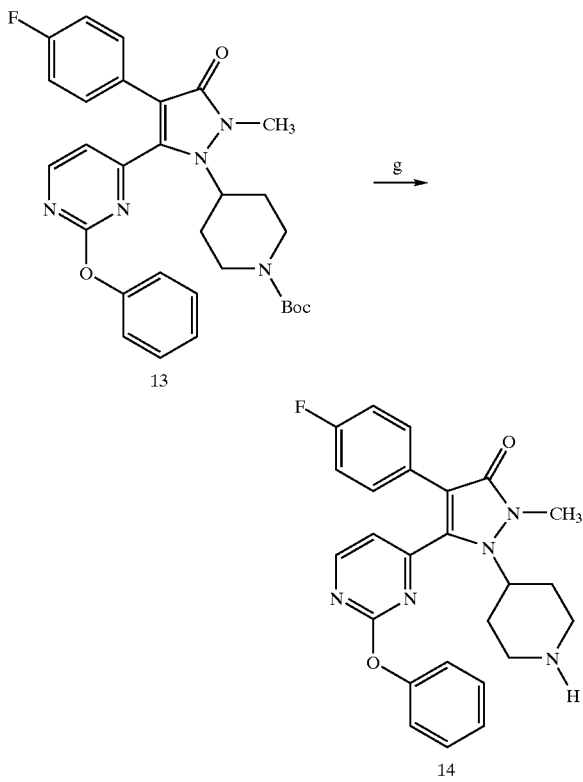

Reagents and conditions: (g) TFA, CH$_2$Cl$_2$; rt, 30 min.

EXAMPLE 3

4-(4-Fluorophenyl)-2-methyl-5-(2-phenoxy-pyrimidin-4-yl)-1-piperidin-4-yl-1,2-dihydro-pyrazol-3-one (14)

Preparation of (4-fluorophenyl)-acetic acid N-methyl-hydrazide (8). To a −78° C. stirred solution of methyl hydrazine (11 mL, 208.5 mmol) in CH$_2$Cl$_2$ (100 mL) is added dropwise a solution of commercially available 4-fluorophenyl-acetyl chloride (12 g, 69.5 mmol) in CH$_2$Cl$_2$ (200 mL). The reaction mixture is stirred for 2 hours at −78° C. and is then slowly warmed to room temperature. The reaction mixture is filtered and the filtrate concentrated under reduced pressure to give a pale yellow oil. Purification over silica (EtOAc) affords 7.6 g (61% yield) of the desired product: $^1$H NMR (300 MHz, CDCl$_3$) δ 7.28–7.23 (m, 2H), 6.99–6.92 (m, 2H), 3.87 (s, 2H), 3.190 (s, 2H), 3.11 (s, 3H); ESI/MS: 183.1 (M+H).

Preparation of 4-{N'-[2-(4-fluoro-phenyl)-acetyl]-N'-methyl-hydrazino}-piperidine-1-carboxylic acid tert-butyl ester (9). To a stirred solution of (4-fluorophenyl)-acetic acid N-methyl-hydrazide, 8, (2 g, 11 mmol) in ethanol (20 mL) is added commercially available 4-oxo-piperidine-1-carboxylic acid tert-butyl ester (2.19 g, 11 mmol). The reaction mixture is refluxed for 30 minutes, then cooled to room temperature after which NaCNBH$_3$ (1.04 g, 16,5 mmol) is added. The pH of the reaction mixture is adjusted to about 3 with concentrated HCl and the reaction mixture stirred for 3 hours at room temperature. The mixture is neutralized with saturated sodium bicarbonate and extracted three times with CH$_2$Cl$_2$. The combined organic layers are dried, filtered and concentrated in vacuo. Purification over silica (EtOAc) affords 3.7 g (93% yield) of the desired product. ESI/MS: 366.3 (M+H).

Preparation of 4-{N'-[2-(4-Fluoro-phenyl)-acetyl]-N'-methyl-N-(2-methylsulfanyl-pyrimidine-4-carbonyl)-hydrazino}-piperidine-1-carboxylic acid tert-butyl ester (10). To a stirred solution of 4-{N'-[2-(4-fluoro-phenyl)-acetyl]-N'-methyl-hydrazino}-piperidine-1-carboxylic acid tert-butyl ester, 9, (3.7 g, 10.1 mmol) in pyridine (10 mL) is added 2-methylsulfanyl-pyrimidine-4-carbonyl chloride (2.9 g, 15.2 mmol). The reaction mixture is stirred at room temperature for 2 hours then diluted with 0.1 N HCl and extracted three times with CH$_2$Cl$_2$. The combined organic layers are dried (MgSO$_4$), filtered and concentrated in vacuo. Purification over silica (EtOAc/hexanes 1:1) affords 1.058 g (20% yield) of the desired product. ESI/MS: 518.2 (M+H).

Preparation of 4-[4-(4-Fluorophenyl)-2-methyl-5-(2-methylsulfanyl-pyrimidin-4-yl)-3-oxo-2,3-dihydro-pyrazol-1-yl]-piperidine-1 carboxylic acid tert-butyl ester (11). To a solution of 4-{N'-[2-(4-fluoro-phenyl)-acetyl]-N'-methyl-N-(2-methylsulfanyl-pyrimidine-4-carbonyl)-hydrazino}-piperidine-1-carboxylic acid tert-butyl ester, 10, (1.058 g, 2.05 mmol) in DMF (2 mL) at 0° C. is slowly added NaH (123 mg of a 60% dispersion in mineral oil, 3.07 mmol). The reaction mixture is stirred for 1 hour at 0° C. and then quenched with 0.1 N HCl. The aqueous layer is extracted three times with CH$_2$Cl$_2$ and the combined organic layers are dried (MgSO$_4$), filtered and concentrated in vacuo. Purification over silica (20% MeOH/CHCl$_3$) affords 0.743 g (73% yield) of the diesired product. ESI/MS: 500.2 (M+H).

Preparation of 4-[4-(4-fluorophenyl)-2-methyl-5-(2-methanesulfonyl-pyrimidin-4-yl)-3-oxo-2,3-dihydro-pyrazol-1-yl]-piperidine-1 carboxylic acid tert-butyl ester (12): To a solution of 4-[4-(4-fluorophenyl)-2-methyl-5-(2-methylsulfanyl-pyrimidin-4-yl)-3-oxo-2,3-dihydro-pyrazol-1-yl]-piperidine-1 carboxylic acid tert-butyl ester, 11, (5.9 g, 12 mmol) in CHCl$_3$ (200 mL) at 0° C. is added meta-chloroperbenzoic acid (4 g, 23.37 mmol). After stirring for 5 minutes, saturated sodium bisulfite (20 mL) is added and the reaction mixture stirred for an additional 5 minutes. The aqueous phase is extracted three times with CH$_2$Cl$_2$, the combined organic phases washed with saturated sodium bicarbonate, dried (MgSO$_4$), filtered and concentrated in vacuo. The crude material is used without further purification.

Preparation of 4-[4-(4-fluorophenyl)-2-methyl-5-(2-phenoxy-pyrimidin-4-yl)-3-oxo-2,3-dihydro-pyrazol-1-yl]-piperidine-1 carboxylic acid tert-butyl ester (13): To a solution of phenol (0.11 g, 1.16 mmol) in THF (5 mL) is added NaH (0.024 g of a 60% dispersion in mineral oil, 0.58 mmol). After stirring for 5 min at room temp, a solution of 4-[4-(4-fluorophenyl)-2-methyl-5-(2-methanesulfonyl-pyrimidin-4-yl)-3-oxo-2,3-dihydro-pyrazol-1-yl]- piperidine-1 carboxylic acid tert-butyl ester, 12, (0.154 g, 0.29 mmol) in THF (3 mL) is added all at once. The reaction mixture is stirred at room temp for 14 hours and then quenched by pouring into aqueous saturated NaHCO$_3$ solution. The aqueous phase is extracted three times with CH$_2$Cl$_2$, the combined organic phases washed with saturated sodium bicarbonate, dried (MgSO$_4$), filtered and concentrated in vacuo. The crude residue was used without further purification in the next step.

Preparation of 4-(4-fluorophenyl)-2-methyl-5-(2-phenoxy-pyrimidin-4-yl)-1-piperidin-4-yl-1,2-dihydro-pyrazol-3-one (14): To a solution of 4-[4-(4-fluorophenyl)-2-methyl-5-(2-phenoxy-pyrimidin-4-yl)-3-oxo-2,3-dihydro-pyrazol-1-yl]-piperidine-1 carboxylic acid tert-butyl ester, 13, (9 g, 15.7 mmol) in CH$_2$Cl$_2$ (90 mL) was added 20% TFA in CH$_2$Cl$_2$. After stirring at room temperature for 0.5 h, the reaction mixture was concentrated in vacuo. Purification by preparatory HPLC afforded the desired product as the trifluoroacetate salt. $^1$H NMR (300 MHz, CDCl$_3$) δ 8.57 (d, J=4.8 Hz, 1H), 7.46 (dd, J=7.8, 7.8 Hz, 2H), 7.31 (dd, J=7.5, 7.5 Hz, 2H), 7.26–7.19 (m, 3H), 7.06 (dd, J=8.7, 8.7 Hz, 2H), 6.90 (d, J=4.8 Hz, 1H), 3.40 (m, 1H), 3.52 (s, 3H), 3.33 (m, 2H), 2.65 (m, 2H), 2.27 (m, 2H), 1.73 (m, 2H). HRMS calcd for C$_{25}$H$_{24}$FN$_5$O$_2$ (M+H)$^+$ 446.1992, found 446.1971.

Non-limiting examples of other compounds comprising the first aspect of Category II include:

4-(4-fluorophenyl)-2-methyl-5-(2-phenoxy-pyrimidin-4-yl)-1-(N-methyl)piperidin-4-yl-1,2-dihydro-pyrazol-3-one;

4-(4-fluorophenyl)-2-methyl-5-(2-phenoxy-pyrimidin-4-yl)-1-benzyl-1,2-dihydro-pyrazol-3-one;

4-(4-fluorophenyl)-2-methyl-5-[2-(2-fluorophenoxy)pyrimidin-4-yl]-1-piperidin-4-yl-1,2-dihydro-pyrazol-3-one;

The second aspect of Category II inflammatory cytokine release inhibiting compounds according to the present invention are 4-R$^1$-substituted-5-(2-R-substituted-pyrimidin-4-yl)-1,2-dihydro-pyrazol-3-ones having the general scaffold with the formula:

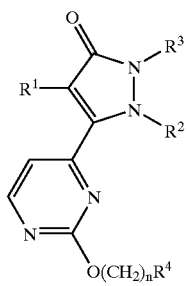

wherein the R$^2$ comprising a lower alkyl unit, R$^3$ comprising a substituted or unsubstituted ring, and the index n is 0, as defined in Table IV herein below.

TABLE IV

| No. | R$^1$ | R$^2$ | R$^3$ | R$^4$ |
|---|---|---|---|---|
| 149 | 4-fluorophenyl | methyl | piperidin-4-yl | phenyl |
| 150 | 4-fluorophenyl | methyl | piperidin-4-yl | 2-hydroxyphenyl |
| 151 | 4-fluorophenyl | methyl | piperidin-4-yl | 4-hydroxyphenyl |

TABLE IV-continued

| No. | R$^1$ | R$^2$ | R$^3$ | R$^4$ |
|---|---|---|---|---|
| 152 | 4-fluorophenyl | methyl | piperidin-4-yl | 2-N-acetyl-aminophenyl |
| 153 | 4-fluorophenyl | methyl | piperidin-4-yl | 3-N-acetyl-aminophenyl |
| 154 | 4-fluorophenyl | methyl | piperidin-4-yl | 2-cyanophenyl |
| 155 | 4-fluorophenyl | methyl | piperidin-4-yl | 4-fluorophenyl |
| 156 | 4-fluorophenyl | methyl | piperidin-4-yl | benzyl |
| 157 | 4-fluorophenyl | methyl | piperidin-4-yl | (S)-α-methylbenzyl |
| 158 | 4-fluorophenyl | methyl | piperidin-4-yl | (R)-α-methylbenzyl |
| 159 | 4-fluorophenyl | methyl | N-methylpiperidin-4-yl | phenyl |
| 160 | 4-fluorophenyl | methyl | N-methylpiperidin-4-yl | 2-hydroxyphenyl |
| 161 | 4-fluorophenyl | methyl | N-methylpiperidin-4-yl | 4-hydroxyphenyl |
| 162 | 4-fluorophenyl | methyl | N-methylpiperidin-4-yl | 2-N-acetyl-aminophenyl |
| 163 | 4-fluorophenyl | methyl | N-methylpiperidin-4-yl | 3-N-acetyl-aminophenyl |
| 164 | 4-fluorophenyl | methyl | N-methylpiperidin-4-yl | 2-cyanophenyl |
| 165 | 4-fluorophenyl | methyl | N-methylpiperidin-4-yl | 4-fluorophenyl |
| 166 | 4-fluorophenyl | methyl | N-methylpiperidin-4-yl | benzyl |
| 167 | 4-fluorophenyl | methyl | N-methylpiperidin-4-yl | (S)-α-methylbenzyl |
| 168 | 4-fluorophenyl | methyl | N-methylpiperidin-4-yl | (R)-α-methylbenzyl |
| 169 | 4-fluorophenyl | methyl | morpholin-4-yl | phenyl |
| 170 | 4-fluorophenyl | methyl | morpholin-4-yl | 2-hydroxyphenyl |
| 171 | 4-fluorophenyl | methyl | morpholin-4-yl | 4-hydroxyphenyl |
| 172 | 4-fluorophenyl | methyl | morpholin-4-yl | 2-N-acetyl-aminophenyl |
| 173 | 4-fluorophenyl | methyl | morpholin-4-yl | 3-N-acetyl-aminophenyl |
| 174 | 4-fluorophenyl | methyl | morpholin-4-yl | 2-cyanophenyl |
| 175 | 4-fluorophenyl | methyl | morpholin-4-yl | 4-fluorophenyl |
| 176 | 4-fluorophenyl | methyl | morpholin-4-yl | benzyl |
| 177 | 4-fluorophenyl | methyl | morpholin-4-yl | (S)-α-methylbenzyl |
| 178 | 4-fluorophenyl | methyl | morpholin-4-yl | (R)-α-methylbenzyl |
| 179 | 4-fluorophenyl | methyl | N-acetylpiperidin-4-yl | phenyl |
| 180 | 4-fluorophenyl | methyl | N-acetylpiperidin-4-yl | 2-hydroxyphenyl |
| 181 | 4-fluorophenyl | methyl | N-acetylpiperidin-4-yl | 4-hydroxyphenyl |
| 182 | 4-fluorophenyl | methyl | N-acetylpiperidin-4-yl | 2-N-acetyl-aminophenyl |
| 183 | 4-fluorophenyl | methyl | N-acetylpiperidin-4-yl | 3-N-acetyl-aminophenyl |
| 184 | 4-fluorophenyl | methyl | N-acetylpiperidin-4-yl | 2-cyanophenyl |
| 185 | 4-fluorophenyl | methyl | N-acetylpiperidin-4-yl | 4-fluorophenyl |
| 186 | 4-fluorophenyl | methyl | N-acetylpiperidin-4-yl | benzyl |
| 187 | 4-fluorophenyl | methyl | N-acetylpiperidin-4-yl | (S)-α-methylbenzyl |
| 188 | 4-fluorophenyl | methyl | N-acetylpiperidin-4-yl | (R)-α-methylbenzyl |

The following is an example of the preparation of compounds encompassed within the second aspect of Category II analogs according to the present invention.

Scheme IV:
Preparation of Second Aspect of Category II

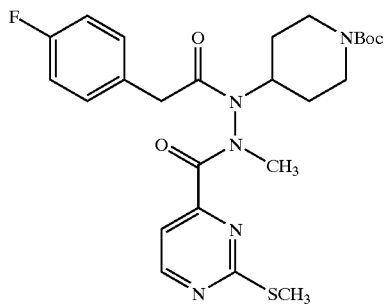

17

Reagents and conditions: (d) NaH, DMF; 0° C., 1 hr.

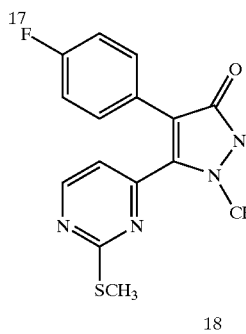

18

Reagents and conditions: (e) m-CPBA, CHCl₃; 0° C., 5 min.

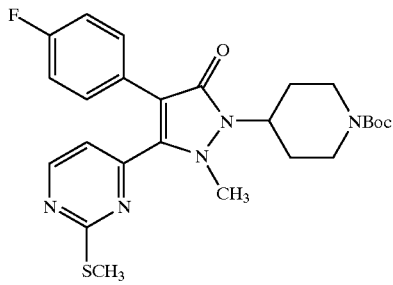

19

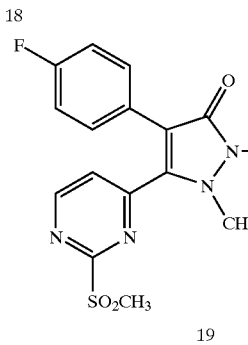

19

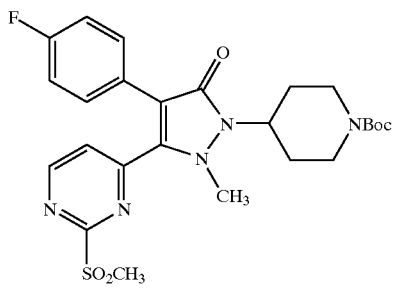

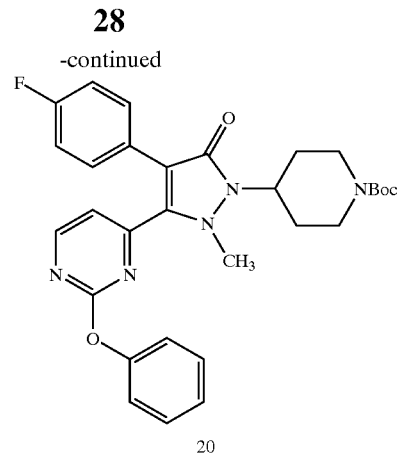

20

Reagents and conditions: (f) phenol, NaH, THF; rt, 14 hr.

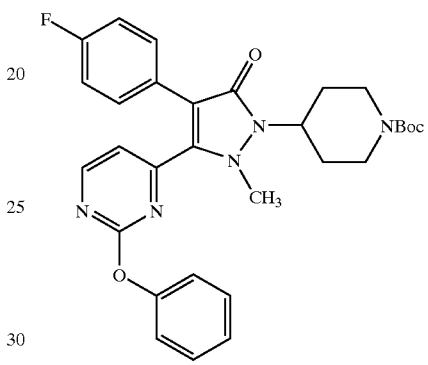

20

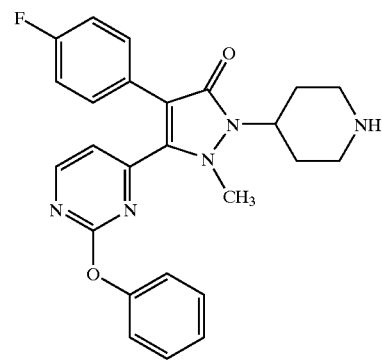

21

Reagents and conditions: (g) TFA, CH₂Cl₂; rt, 30 min.

EXAMPLE 4

4-(4-Fluorophenyl)-2-piperidin-4-yl-5-(2-phenoxy-pyrimidin-4-yl)-1-methyl-1,2-dihydro-pyrazol-3-one (21)

Preparation of 2-Methylsulfanyl-pyrimidine-4-carboxylic acid N-methyl-hydrazide (15): To a −78° C. stirred solution of methyl hydrazine (17 mL, 318 mmol) in CH₂Cl₂ (500 mL) is added dropwise a solution of 2-methylsulfanyl-pyrimidine-4-carbonyl chloride (20 g, 106 mmol) in CH₂Cl₂ (500 mL). The reaction mixture is stirred for 2 hours at −78° C. and then slowly warmed to room temperature. The reaction mixture is concentrated under reduced pressure to give a purple oil. Purification over silica (EtOAc/hexanes 1:1) affords 6.98 g (33% yield) of the desired compound. $^1$H NMR (300 MHz, CDCl₃) δ 8.69–8.64 (m, 1H), 7.35–7.08 (m, 1H), 3.40 (s, 3H), 3.36 (s, 2H), 2.59 (s, 3H); ESI/MS: 199.1 (M+H).

Preparation of 4-[N'-Methyl-N'-(2-methylsulfanyl-pyrimidine-4-carbonyl)-hydrazino]-piperidine-1-carboxylic acid tert-butyl ester (16). To a stirred solution of 2-Methylsulfanyl-pyrimidine-4-carboxylic acid N-methyl-hydrazide, 15, (15 g, 75.8 mmol) in ethanol (60 mL) is added 4-oxo-piperidine-1-carboxylic acid tert-butyl ester (15.1 g, 75.8 mmol). The reaction mixture is refluxed for 1.5 hour, cooled to room temperature and NaCNBH$_3$ (7.14 g, 113.7 mmol) added. The pH of the reaction mixture is adjusted to 3 with concentrated HCl and the reaction mixture stirred for 3 hours at room temperature. The mixture is neutralized with saturated sodium bicarbonate and extracted three times with CH$_2$Cl$_2$ and the combined organic layers are dried (MgSO$_4$), filtered and concentrated in vacuo. Purification over silica (EtOAc) affords 19.7 g (68% yield) of the desired product. $^1$H NMR (300 MHz, CDCl$_3$) δ 8.70 (q, J=2.9 Hz, 1H), 7.36–7.27 (m, 2H), 2.61 (s, 1H), 4.16 (q, J=6.9 Hz, 1H), 3.97–3.78 (m, 2H), 3.37 (d, J=16 Hz, 3H), 2.91–2.79 (m, 2H), 2.61 (s, 3H), 1.93–1.89 (m, 2H), 1.70–1.65 (m, 2H), 1.48 (d, J=8 Hz, 9H); ESI/MS: 382.3 (M+H).

Preparation of 4-{N-[2-(4-fluoro-phenyl)-acetyl]-N'-methyl-N'-(2-methylsulfanyl-pyrimidine-4-carbonyl)-hydrazino}-piperidine-1-carboxylic acid tert-butyl ester (17). To a stirred 0° C. solution of 4-[N'-Methyl-N'-(2-methylsulfanyl-pyrimidine-4-carbonyl)-hydrazino]-piperidine-1-carboxylic acid tert-butyl ester, 16, (19.8 g, 51.7 mmol) in pyridine (25 mL) is added (4-fluorophenyl) acetyl chloride (10 g, 57.9 mmol). The reaction mixture is slowly warmed to room temperature and then stirred for 2 hours. The reaction mixture is then concentrated in vacuo. Purification over silica (100% EtOAc) affords 42 g of the desired product: $^1$H NMR (300 MHz, CDCl$_3$) δ 8.80–8.70 (m, 1H), 7.40–7.32 (m, 1H), 7.29–7.18 (m, 2H), 7.07–6.94 (m, 2H), 4.24–4.10 (m, 3H), 3.82–3.59 (m, 2H), 3.33 (d, J=8.4 Hz, 3H), 2.88–2.67 (m, 2H), 2.60 (d, J=18.6 Hz, 3H), 1.96–1.92 (m, 2H), 1.70–1.65 (m, 2H), 1.48 (d, J=4.0 Hz, 9H); ESI/MS: 518.2 (M+H).

Preparation of 4-[4-(4-Fluorophenyl)-2-methyl-3-(2-methylsulfanyl-pyrimidin-4-yl)-5-oxo-2,5-dihydro-pyrazol-1-yl]-piperidine-1 carboxylic acid tert-butyl ester (18). To a 0° C. solution of 4-{N-[2-(4-fluoro-phenyl)-acetyl]-N'-methyl-N'-(2-methylsulfanyl-pyrimidine-4-carbonyl)-hydrazino}-piperidine-1-carboxylic acid tert-butyl ester, 17, (26.7 g, 51.7 mmol) in DMF (50 mL) is slowly added NaH (3.1 g of a 60% dispersion in mineral oil, 77.55 mmol). The reaction mixture is stirred for 0.5 h at 0° C. and then quenched with 1.0 N HCl. The aqueous layer is extracted threee times with CH$_2$Cl$_2$. The combined organic layers are dried (MgSO$_4$), filtered and concentrated in vacuo. Purification over silica (100% EtOAc) affords 12 g (45% yield) of the desired product: $^1$H NMR (300 MHz, CDCl$_3$) δ 8.50 (d, J=4.9 Hz, 1H), 7.35–7.29 (m, 2H), 7.02 (t, J=6.8 Hz, 2H), 6.85 (d, J=5.1 Hz, 1H), 4.42–4.32 (m, 3H), 3.28 (s, 3H), 2.88 (t, 12.8 Hz, 2H), 2.58 (s, 3H), 2.79–2.39 (m, 2H), 1.94 (d, J=11.7 Hz, 2H), 1.50 (s, 9H); ESI/MS: 500.3 (M+H).

The same procedures which are used to convert compound 11 to the analog compound 14 as depicted in Scheme III, can be utilized for the conversion of compound 18 to analog compound 21 in Scheme IV.

4-(4-Fluorophenyl)-1-methyl-5-(2-phenoxy-pyrimidin-4-yl)-2-piperidin-4-yl-1,2-dihydro-pyrazol-3-one trifluoroacetic acid salt (21): $^1$H NMR (300 MHz, CD$_3$OD) δ 8.64 (dd, J=5.4, 2.1 Hz, 1H), 7.44–7.05 (m, 10H), 4.61–4.47 (m, 1H), 3.55 (m, 2H), 3.39 (bs, 3H), 3.21–3.13 (m, 2H), 2.89–2.78 (m, 2H), 2.09 (m, 2H). HRMS calcd for C$_{25}$H$_{24}$FN$_5$O$_2$ (M+H)$^+$446.1992; found 446.2013.

The compounds which comprise Category III analogs of the present invention have the formula:

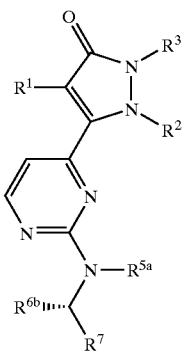

wherein the compounds comprising the first aspect of Category III have the formula:

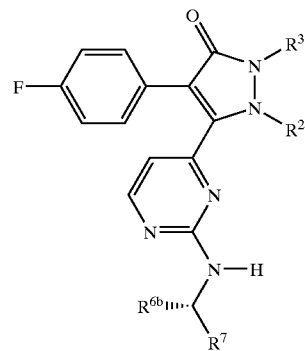

wherein R$^3$ is C$_1$–C$_4$ alkyl, R$^7$ is aryl, and R$^2$, R$^3$, R$^{6b}$, and R$^7$ are described herein below in Table V. The analogs described herein have the indicated stereochemistry when R$^{6b}$ is not hydrogen.

TABLE V

| No. | R$^2$ | R$^3$ | R$^{bb}$ | R$^7$ |
|---|---|---|---|---|
| 189 | piperidin-4-yl | methyl | hydrogen | phenyl |
| 190 | piperidin-4-yl | methyl | hydrogen | 4-fluorophenyl |
| 191 | piperidin-4-yl | methyl | hydrogen | 2-aminophenyl |
| 192 | piperidin-4-yl | methyl | hydrogen | 2-methylphenyl |
| 193 | piperidin-4-yl | methyl | hydrogen | 4-methylphenyl |
| 194 | piperidin-4-yl | methyl | hydrogen | 4-methoxyphenyl |
| 195 | piperidin-4-yl | methyl | hydrogen | 4-(propane-sulfonyl)phenyl |
| 196 | piperidin-4-yl | methyl | hydrogen | 3-benzo[1,3]dioxol-5-yl |
| 197 | piperidin-4-yl | methyl | hydrogen | pyridin-2-yl |
| 198 | piperidin-4-yl | methyl | hydrogen | pyridin-3-yl |
| 199 | N-methylpiperidin-4-yl | methyl | hydrogen | phenyl |
| 200 | N-methylpiperidin-4-yl | methyl | hydrogen | 4-fluorophenyl |
| 201 | N-methylpiperidin-4-yl | methyl | hydrogen | 2-aminophenyl |
| 202 | N-methylpiperidin-4-yl | methyl | hydrogen | 2-methylphenyl |
| 203 | N-methylpiperidin-4-yl | methyl | hydrogen | 4-methylphenyl |
| 204 | N-methylpiperidin-4-yl | methyl | hydrogen | 4-methoxyphenyl |
| 205 | N-methylpiperidin-4-yl | methyl | hydrogen | 4-(propane-sulfonyl)phenyl |
| 206 | N-methylpiperidin-4-yl | methyl | hydrogen | 3-benzo[1,3]dioxol-5-yl |
| 207 | N-methylpiperidin-4-yl | methyl | hydrogen | pyridin-2-yl |
| 208 | N-methylpiperidin-4-yl | methyl | hydrogen | pyridin-3-yl |
| 209 | morpholin-4-yl | methyl | hydrogen | phenyl |
| 210 | morpholin-4-yl | methyl | hydrogen | 4-fluorophenyl |
| 211 | morpholin-4-yl | methyl | hydrogen | 2-aminophenyl |
| 212 | morpholin-4-yl | methyl | hydrogen | 2-methylphenyl |
| 213 | morpholin-4-yl | methyl | hydrogen | 4-methylphenyl |

TABLE V-continued

| No. | R² | R³ | R^bb | R⁷ |
|---|---|---|---|---|
| 214 | morpholin-4-yl | methyl | hydrogen | 4-methoxyphenyl |
| 215 | morpholin-4-yl | methyl | hydrogen | 4-(propane-sulfonyl)phenyl |
| 216 | morpholin-4-yl | methyl | hydrogen | 3-benzo[1,3]dioxol-5-yl |
| 217 | morpholin-4-yl | methyl | hydrogen | pyridin-2-yl |
| 218 | morpholin-4-yl | methyl | hydrogen | pyridin-3-yl |
| 219 | N-acetylpiperidin-4-yl | methyl | hydrogen | phenyl |
| 220 | N-acetylpiperidin-4-yl | methyl | hydrogen | 4-fluorophenyl |
| 221 | N-acetylpiperidin-4-yl | methyl | hydrogen | 2-aminophenyl |
| 222 | N-acetylpiperidin-4-yl | methyl | hydrogen | 2-methylphenyl |
| 223 | N-acetylpiperidin-4-yl | methyl | hydrogen | 4-methylphenyl |
| 224 | N-acetylpiperidin-4-yl | methyl | hydrogen | 4-methoxyphenyl |
| 225 | N-acetylpiperidin-4-yl | methyl | hydrogen | 4-(propane-sulfonyl)phenyl |
| 226 | N-acetylpiperidin-4-yl | methyl | hydrogen | 3-benzo[1,3]dioxol-5-yl |
| 227 | N-acetylpiperidin-4-yl | methyl | hydrogen | pyridin-2-yl |
| 228 | N-acetylpiperidin-4-yl | methyl | hydrogen | pyridin-3-yl |
| 229 | piperidin-4-yl | methyl | methyl | phenyl |
| 230 | piperidin-4-yl | methyl | methyl | 4-fluorophenyl |
| 231 | piperidin-4-yl | methyl | methyl | 2-aminophenyl |
| 232 | piperidin-4-yl | methyl | methyl | 2-methylphenyl |
| 233 | piperidin-4-yl | methyl | methyl | 4-methylphenyl |
| 234 | piperidin-4-yl | methyl | methyl | 4-methoxy-phenyl |
| 235 | piperidin-4-yl | methyl | methyl | 4-(propane-sulfonyl)phenyl |
| 236 | piperidin-4-yl | methyl | methyl | 3-benzo[1,3]dioxol-5-yl |
| 237 | piperidin-4-yl | methyl | methyl | pyridin-2-yl |
| 238 | piperidin-4-yl | methyl | methyl | pryidin-3-yl |
| 239 | N-methylpiperidin-4-yl | methyl | methyl | phenyl |
| 240 | N-methylpiperidin-4-yl | methyl | methyl | 4-fluorophenyl |
| 241 | N-methylpiperidin-4-yl | methyl | methyl | 2-aminophenyl |
| 242 | N-methylpiperidin-4-yl | methyl | methyl | 2-methylphenyl |
| 243 | N-methylpiperidin-4-yl | methyl | methyl | 4-methylphenyl |
| 244 | N-methylpiperidin-4-yl | methyl | methyl | 4-methoxyphenyl |
| 245 | N-methylpiperidin-4-yl | methyl | methyl | 4-(propane-sulfonyl)phenyl |
| 246 | N-methylpiperidin-4-yl | methyl | methyl | 3-benzo[1,3]dioxol-5-yl |
| 247 | N-methylpiperidin-4-yl | methyl | methyl | pyridin-2-yl |
| 248 | N-methylpiperidin-4-yl | methyl | methyl | pyridin-3-yl |
| 249 | morpholin-4-yl | methyl | methyl | phenyl |
| 250 | morpholin-4-yl | methyl | methyl | 4-fluorophenyl |
| 251 | morpholin-4-yl | methyl | methyl | 2-aminophenyl |
| 252 | morpholin-4-yl | methyl | methyl | 2-methylphenyl |
| 253 | morpholin-4-yl | methyl | methyl | 4-methylphenyl |
| 254 | morpholin-4-yl | methyl | methyl | 4-methoxyphenyl |
| 255 | morpholin-4-yl | methyl | methyl | 4-(propane-sulfonyl)phenyl |
| 256 | morpholin-4-yl | methyl | methyl | 3-benzo[1,3]dioxol-5-yl |
| 257 | morpholin-4-yl | methyl | methyl | pyridin-2-yl |
| 258 | morpholin-4-yl | methyl | methyl | pyridin-3-yl |
| 259 | N-acetylpiperidin-4-yl | methyl | methyl | phenyl |
| 260 | N-acetylpiperidin-4-yl | methyl | methyl | 4-fluorophenyl |
| 261 | N-acetylpiperidin-4-yl | methyl | methyl | 2-aminophenyl |
| 262 | N-acetylpiperidin-4-yl | methyl | methyl | 2-methylphenyl |
| 263 | N-acetylpiperidin-4-yl | methyl | methyl | 4-methylphenyl |
| 264 | N-acetylpiperidin-4-yl | methyl | methyl | 4-methoxyphenyl |
| 265 | N-acetylpiperidin-4-yl | methyl | methyl | 4-(propane-sulfonyl)phenyl |
| 266 | N-acetylpiperidin-4-yl | methyl | methyl | 3-benzo[1,3]dioxol-5-yl |
| 267 | N-acetylpiperidin-4-yl | methyl | methyl | pyridin-2-yl |
| 268 | N-acetylpiperidin-4-yl | methyl | methyl | pyridin-3-yl |

Utilizing intermediates such as compound 12, as a convenient starting point the analogs 189–268 and others encompassed within the description of this category can be suitably prepared by the procedure outlined herein below. In the following example, $R^1$ is 4-fluorophenyl, however, the formulator may suitably substitute any starting material compatible with this procedure, inter alia, methyl phenylacetate, methyl 4-chlorophenyl-acetate, and methyl 3-(trifluoromethyl)phenyl acetate.

Scheme V: Preparation of First Aspect of Category III

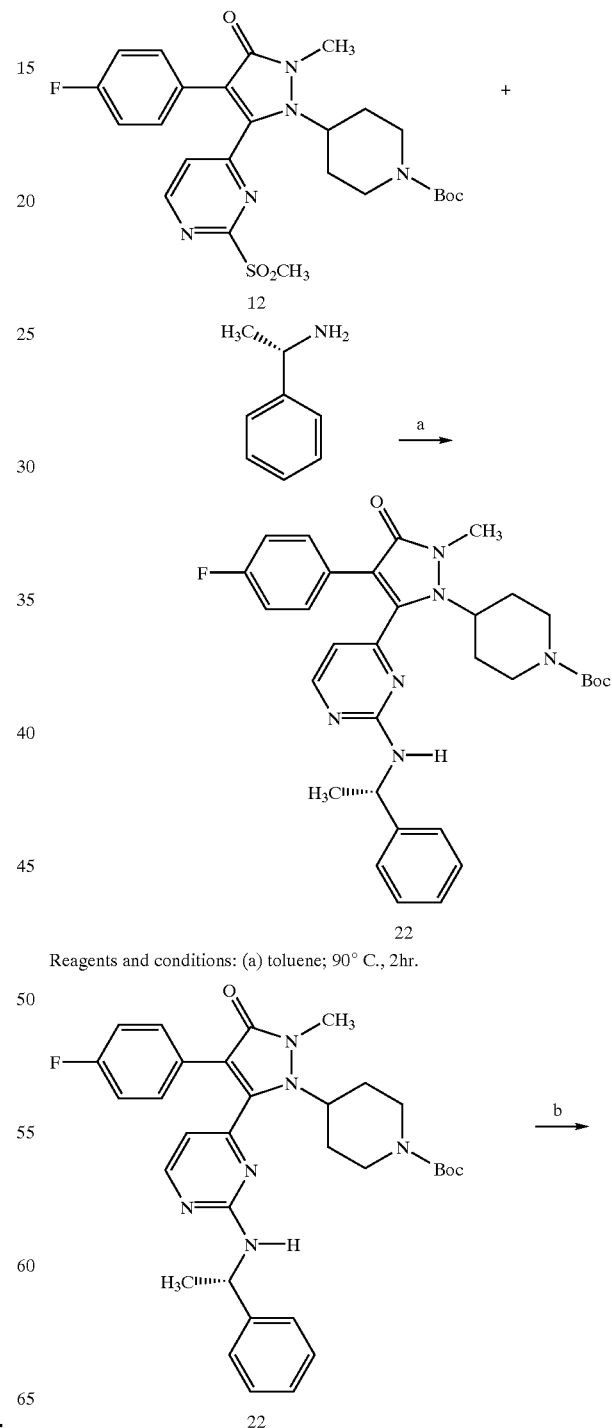

Reagents and conditions: (a) toluene; 90° C., 2hr.

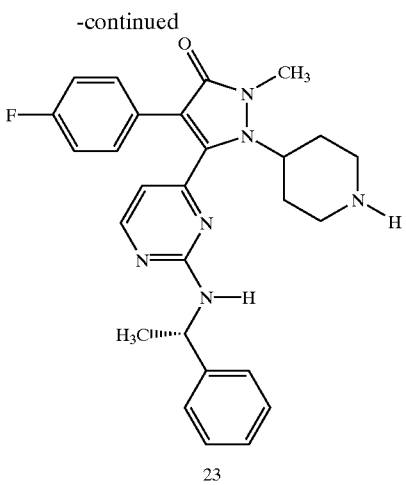

23

Reagents and conditions: (b) TFA, CH$_2$Cl$_2$; rt, 30 min.

EXAMPLE 5

4-(4-Fluorophenyl)-2-methyl-5-[2-(1-phenylethylamino)-pyrimidin-4-yl]-1-piperidin-4-yl-1,2-dihydropyrazol-3-one (23)

Preparation of 4-{4-(4-fluorophenyl)-2-methyl-3-oxo-5-[2-(1-phenylethylamino)-pyrimidin-4-yl]-2,3-dihydro-pyrazol-1-yl}-piperidine-1-carboxylic acid tert-butyl ester (22): To a solution of 4-[4-(4-fluorophenyl)-2-methyl-5-(2-methanesulfonyl-pyrimidin-4-yl)-3-oxo-2,3-dihydro-pyrazol-1-yl]-piperidine-1 carboxylic acid tert-butyl ester, 12, (6 g, 12 mmol) in toluene (30 mL) is added (S)-(α)-methylbenzyl amine (1.55 mL, 24 mmol). After stirring at 90° C. for 2 hours, the reaction mixture is cooled to room temperature and then concentrated in vacuo. Purification over silica (50% EtOAc/hexane) affords the desired product.

Preparation of 4-(4-fluorophenyl)-2-methyl-5-[2-(1-phenylethylamino)-pyrimidin-4-yl]-1-piperidin-4-yl-1,2-dihydropyrazol-3-one (23): To a solution of 4-[4-(4-fluorophenyl)-2-methyl-5-(2-methanesulfonyl-pyrimidin-4-yl)-3-oxo-2,3-dihydro-pyrazol-1-yl]-piperidine-1 carboxylic acid tert-butyl ester, 22, (6 g, 12 mmol) (9 g, 15.7 mmol) in CH$_2$Cl$_2$ (90 mL) was added 20% TFA in CH$_2$Cl$_2$. After stirring at room temperature for 0.5 hour, the reaction mixture is concentrated in vacuo. Purification by preparatory HPLC affords the desired product as the trifluoroacetate salt. $[\alpha]_D$ −40° (c 1.8, MeOH), $^1$H NMR (300 MHz, CD$_3$OD) δ 8.30 (d, J=4.8 Hz, 1H), 7.42–6.96 (m, 9H), 6.50 (d, J=4.8 Hz, 1H), 5.14–5.08 (m, 1H), 4.10–4.02 (m, 1H), 3.56 (s, 3H), 3.50–3.42 (m, 1H), 3.38–3.22 (m, 2H), 3.01–2.85 (m, 2H), 2.22–1.70 (m, 3H), 1.52 (d, J=6.9 Hz, 3H). HRMS calcd for C$_{27}$H$_{29}$FN$_6$O (M+H)$^+$473.2465; found 473.2486.

Non-limiting examples of other compounds comprising the first aspect of Category III include:

4-(4-Fluorophenyl)-2-methyl-5-{2-[1-(4-fluorophenyl) ethylamino]-pyrimidin-4-yl}-1-piperidin-4-yl-1,2-dihydropyrazol-3-one;

4-(4-Fluorophenyl)-2-methyl-5-{2-[1-(3-fluorophenyl) ethylamino]-pyrimidin-4-yl}-1-piperidin-4-yl-1,2-dihydropyrazol-3-one;

4-(4-Fluorophenyl)-2-methyl-5-{2-[1-(2-fluorophenyl) ethylamino]-pyrimidin-4-yl}-1-piperidin-4-yl-1,2-dihydropyrazol-3-one;

The second aspect of Category III inflammatory cytokine release inhibiting compounds according to the present invention are 4-fluorophenyl-5-(2-R-substituted-pyrimidin-4-yl)-1,2-dihydropyrazol-3-ones having the general scaffold with the formula:

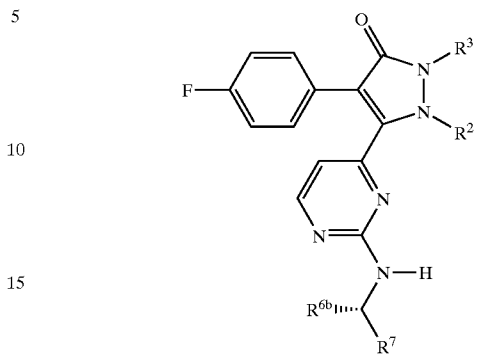

wherein R$^3$ is C$_1$–C$_4$ alkyl, R$^7$ is substituted or unsubstituted C$_1$–C$_4$ alkyl, and R$^2$, R$^3$, R$^{6b}$, and R$^7$ are described herein below in Table VI. The analogs described herein have the indicated stereochemistry when R$^{6b}$ is not hydrogen.

TABLE VI

| No. | R$^2$ | R$^3$ | R$^{6b}$ | R$^7$ |
|---|---|---|---|---|
| 269 | piperidin-4-yl | methyl | hydrogen | hydrogen |
| 270 | piperidin-4-yl | methyl | hydrogen | methyl |
| 271 | piperidin-4-yl | methyl | hydrogen | ethyl |
| 272 | piperidin-4-yl | methyl | hydrogen | vinyl |
| 273 | piperidin-4-yl | methyl | hydrogen | cyclopropyl |
| 274 | piperidin-4-yl | methyl | hydrogen | cyclohexyl |
| 275 | piperidin-4-yl | methyl | hydrogen | methoxymethyl |
| 276 | piperidin-4-yl | methyl | hydrogen | methoxyethyl |
| 277 | piperidin-4-yl | methyl | hydrogen | 1-hydroxy-1-methylethyl |
| 278 | piperidin-4-yl | methyl | hydrogen | —CO$_2$H |
| 279 | N-methylpiperidin-4-yl | methyl | hydrogen | hydrogen |
| 280 | N-methylpiperidin-4-yl | methyl | hydrogen | methyl |
| 281 | N-methylpiperidin-4-yl | methyl | hydrogen | ethyl |
| 282 | N-methylpiperidin-4-yl | methyl | hydrogen | vinyl |
| 283 | N-methylpiperidin-4-yl | methyl | hydrogen | cyclopropyl |
| 284 | N-methylpiperidin-4-yl | methyl | hydrogen | cyclohexyl |
| 285 | N-methylpiperidin-4-yl | methyl | hydrogen | methoxymethyl |
| 286 | N-methylpiperidin-4-yl | methyl | hydrogen | methoxyethyl |
| 287 | N-methylpiperidin-4-yl | methyl | hydrogen | 1-hydroxy-1-methylethyl |
| 288 | N-methylpiperidin-4-yl | methyl | hydrogen | —CO$_2$H |
| 289 | morpholin-4-yl | methyl | hydrogen | hydrogen |
| 290 | morpholin-4-yl | methyl | hydrogen | methyl |
| 291 | morpholin-4-yl | methyl | hydrogen | ethyl |
| 292 | morpholin-4-yl | methyl | hydrogen | vinyl |
| 293 | morpholin-4-yl | methyl | hydrogen | cyclopropyl |
| 294 | morpholin-4-yl | methyl | hydrogen | cyclohexyl |
| 295 | morpholin-4-yl | methyl | hydrogen | methoxymethyl |
| 296 | morpholin-4-yl | methyl | hydrogen | methoxyethyl |
| 297 | morpholin-4-yl | methyl | hydrogen | 1-hydroxy-1-methylethyl |
| 298 | morpholin-4-yl | methyl | hydrogen | —CO$_2$H |
| 299 | N-acetylpiperidin-4-yl | methyl | hydrogen | hydrogen |
| 300 | N-acetylpiperidin-4-yl | methyl | hydrogen | methyl |
| 301 | N-acetylpiperidin-4-yl | methyl | hydrogen | ethyl |
| 302 | N-acetylpiperidin-4-yl | methyl | hydrogen | vinyl |
| 303 | N-acetylpiperidin-4-yl | methyl | hydrogen | cyclopropyl |
| 304 | N-acetylpiperidin-4-yl | methyl | hydrogen | cyclohexyl |
| 305 | N-acetylpiperidin-4-yl | methyl | hydrogen | methoxymethyl |
| 306 | N-acetylpiperidin-4-yl | methyl | hydrogen | methoxyethyl |
| 307 | N-acetylpiperidin-4-yl | methyl | hydrogen | 1-hydroxy-1-methylethyl |
| 308 | N-acetylpiperidin-4-yl | methyl | hydrogen | —CO$_2$H |
| 309 | piperidin-4-yl | methyl | methyl | hydrogen |
| 310 | piperidin-4-yl | methyl | methyl | methyl |
| 311 | piperidin-4-yl | methyl | methyl | ethyl |
| 312 | piperidin-4-yl | methyl | methyl | vinyl |

TABLE VI-continued

| No. | R² | R³ | R⁶ᵇ | R⁷ |
|---|---|---|---|---|
| 313 | piperidin-4-yl | methyl | methyl | cyclopropyl |
| 314 | piperidin-4-yl | methyl | methyl | cyclohexyl |
| 315 | piperidin-4-yl | methyl | methyl | methoxymethyl |
| 316 | piperidin-4-yl | methyl | methyl | methoxyethyl |
| 317 | piperidin-4-yl | methyl | methyl | 1-hydroxy-1-methylethyl |
| 318 | piperidin-4-yl | methyl | methyl | —CO₂H |
| 319 | N-methylpiperidin-4-yl | methyl | methyl | hydrogen |
| 320 | N-methylpiperidin-4-yl | methyl | methyl | methyl |
| 321 | N-methylpiperidin-4-yl | methyl | methyl | ethyl |
| 322 | N-methylpiperidin-4-yl | methyl | methyl | vinyl |
| 323 | N-methylpiperidin-4-yl | methyl | methyl | cyclopropyl |
| 324 | N-methylpiperidin-4-yl | methyl | methyl | cyclohexyl |
| 325 | N-methylpiperidin-4-yl | methyl | methyl | methoxymethyl |
| 326 | N-methylpiperidin-4-yl | methyl | methyl | methoxyethyl |
| 327 | N-methylpiperidin-4-yl | methyl | methyl | 1-hydroxy-1-methylethyl |
| 328 | N-methylpiperidin-4-yl | methyl | methyl | —CO₂H |
| 329 | morpholin-4-yl | methyl | methyl | hydrogen |
| 330 | morpholin-4-yl | methyl | methyl | methyl |
| 331 | morpholin-4-yl | methyl | methyl | ethyl |
| 332 | morpholin-4-yl | methyl | methyl | vinyl |
| 333 | morpholin-4-yl | methyl | methyl | cyclopropyl |
| 334 | morpholin-4-yl | methyl | methyl | cyclohexyl |
| 335 | morpholin-4-yl | methyl | methyl | methoxymethyl |
| 336 | morpholin-4-yl | methyl | methyl | methoxyethyl |
| 337 | morpholin-4-yl | methyl | methyl | 1-hydroxy-1-methylethyl |
| 338 | morpholin-4-yl | methyl | methyl | —CO₂H |
| 339 | N-acetylpiperidin-4-yl | methyl | methyl | hydrogen |
| 340 | N-acetylpiperidin-4-yl | methyl | methyl | methyl |
| 341 | N-acetylpiperidin-4-yl | methyl | methyl | ethyl |
| 342 | N-acetylpiperidin-4-yl | methyl | methyl | vinyl |
| 343 | N-acetylpiperidin-4-yl | methyl | methyl | cyclopropyl |
| 344 | N-acetylpiperidin-4-yl | methyl | methyl | cyclohexyl |
| 345 | N-acetylpiperidin-4-yl | methyl | methyl | methoxymethyl |
| 346 | N-acetylpiperidin-4-yl | methyl | methyl | methoxyethyl |
| 347 | N-acetylpiperidin-4-yl | methyl | methyl | 1-hydroxy-1-methylethyl |
| 348 | N-acetylpiperidin-4-yl | methyl | methyl | —CO₂H |

Utilizing intermediates such as compound 12, as a convenient starting point the analogs 269–348 and others encompassed within the description of this category can be suitably prepared by the procedure outlined herein below. In the following example, $R^1$ is 4-fluorophenyl, however, the formulator may suitably substitute any starting material compatible with this procedure, inter alia, methyl phenylacetate, methyl 4-chlorophenyl-acetate, and methyl 3-(trifluoromethyl)phenyl acetate.

Scheme VI: Preparation of Second Aspect of Category III

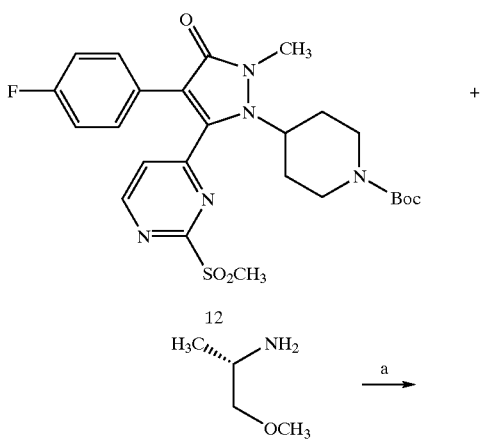

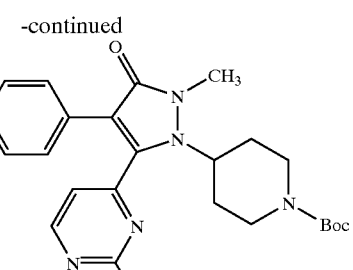

Reagents and conditions: (a) toluene; 90° C. 2 hr.

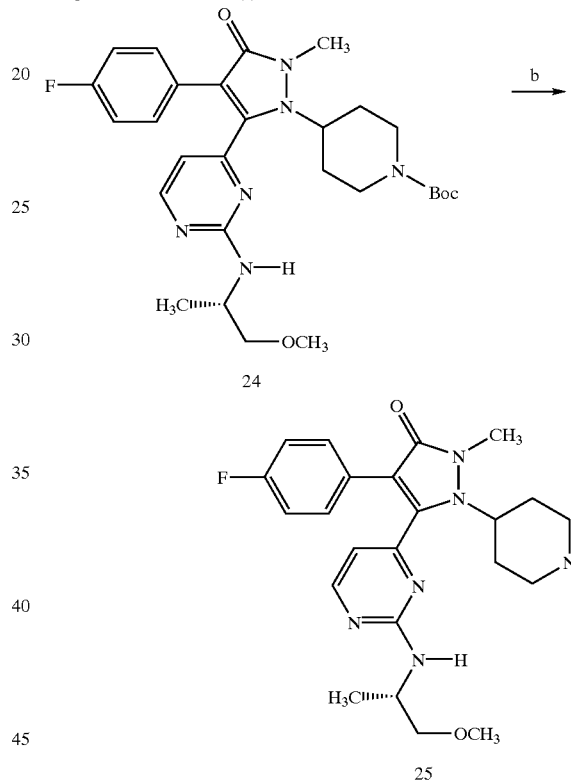

Reagents and conditions: (b) TFA, CH₂Cl₂; rt, 30 min.

EXAMPLE 6

4-(4-Fluorophenyl)-5-[2-(2-methoxy-1-(S)-methyl-ethylamino)pyrimidin-4-yl]-2-methyl-1-piperidin-4-yl-1,2-dihydropyrazol-3-one (25)

Preparation of 4-{4-(4-fluorophenyl)-2-methyl-3-oxo-5-[2-(2-methoxy-1-(S)-methyl-ethylamino)-pyrimidin-4-yl]-2,3-dihydro-pyrazol-1-yl}-piperidine-1-carboxylic acid tert-butyl ester (24): To a solution of 4-[4-(4-fluorophenyl)-2-methyl-5-(2-methanesulfonyl-pyrimidin-4-yl)-3-oxo-2,3-dihydro-pyrazol-1-yl]-piperidine-1 carboxylic acid tert-butyl ester, 12, (6 g, 12 mmol) in toluene (30 mL) is added (S)-2-amino-3-methoxypropane (2.14 g, 24 mmol). After stirring at 90° C. for 2 hours, the reaction mixture is cooled to room temperature and then concentrated in vacuo. Purification over silica (50% EtOAc/hexane) affords the desired product.

Preparation of 4-(4-fluorophenyl)-5-[2-(2-methoxy-1-(S)-methyl-ethylamino)-pyrimidin-4-yl]-2-methyl-1-piperidin-4-yl-1,2-dihydropyrazol-3-one (25): To a solution of 4-{4-(4-fluorophenyl)-2-methyl-3-oxo-5-[2-(2-methoxy-1-methyl-ethylamino)-pyrimidin-4-yl]-2,3-dihydro-pyrazol-1-yl}-piperidine-1-carboxylic acid tert-butyl ester, 24, (6.5 g, 12 mmol) in $CH_2Cl_2$ (90 mL) was added 20% TFA in $CH_2Cl_2$. After stirring at room temperature for 0.5 hour, the reaction mixture is concentrated in vacuo. Purification by preparatory HPLC affords the desired product as the trifluoroacetate salt. $[\alpha]_D$ −15° (c 1.7, MeOH), $^1$H NMR (300 MHz, $CD_3OD$) δ 8.32 (d, J=4.8 Hz, 1H), 7.33–7.28 (m, 2H) 7.10–7.04 (m, 2H), 6.64 (d, J=4.8 Hz, 1H), 4.35–4.19 (m, 2H), 3.63 (s, 3H), 3.59–3.35 (m, 4H), 3.37 (s, 3H), 3.12–3.01 (m, 2H), 2.26–2.17 (m, 4H), 1.21 (d, J=6.9 Hz, 3H). HRMS calcd for $C_{23}H_{29}FN_6O_2$ (M +H)$^+$441.2414; found 441.2410.

Non-limiting examples of other compounds comprising the second aspect of Category III include:

4-(4-fluorophenyl)-5-[2-(2-methoxy-1-(S)-methyl-ethylamino)-pyrimidin-4-yl]-2-methyl-1-(N-acetyl)piperidin-4-yl-1,2-dihydropyrazol-3-one;

4-(4-fluorophenyl)-5-[2-(1-(S)-methyl-propylamino)-pyrimidin-4-yl]-2-methyl-1-(N-acetyl)piperidin-4-yl-1,2-dihydropyrazol-3-one;

The third aspect of Category III inflammatory cytokine release inhibiting compounds according to the present invention are 4-fluorophenyl-5-(2-R-substituted-pyrimidin-4-yl)-1,2-dihydropyrazol-3-ones having the general scaffold with the formula:

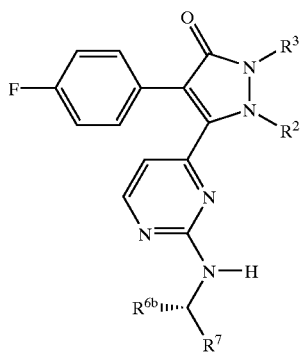

wherein $R^2$ is $C_1$–$C_4$ alkyl, $R^7$ is aryl, and $R^2$, $R^3$, $R^{6b}$, and $R^7$ are described herein below in Table VII. The analogs described herein have the indicated stereochemistry when $R^{6b}$ is not hydrogen.

TABLE VII

| No. | $R^2$ | $R^3$ | $R^{6b}$ | $R^7$ |
| --- | --- | --- | --- | --- |
| 349 | methyl | piperidin-4-yl | hydrogen | phenyl |
| 350 | methyl | piperidin-4-yl | hydrogen | 4-fluorophenyl |
| 351 | methyl | piperidin-4-yl | hydrogen | 2-aminophenyl |
| 352 | methyl | piperidin-4-yl | hydrogen | 2-methylphenyl |
| 353 | methyl | piperidin-4-yl | hydrogen | 4-methylphenyl |
| 354 | methyl | piperidin-4-yl | hydrogen | 4-methoxyphenyl |
| 355 | methyl | piperidin-4-yl | hydrogen | 4-(propane-sulfonyl)phenyl |
| 356 | methyl | piperidin-4-yl | hydrogen | 3-benzo[1,3]dioxol-5-yl |
| 357 | methyl | piperidin-4-yl | hydrogen | pyridin-2-yl |
| 358 | methyl | piperidin-4-yl | hydrogen | pyridin-3-yl |
| 359 | methyl | N-methylpiperidin-4-yl | hydrogen | phenyl |
| 360 | methyl | N-methylpiperidin-4-yl | hydrogen | 4-fluorophenyl |
| 361 | methyl | N-methylpiperidin-4-yl | hydrogen | 2-aminophenyl |
| 362 | methyl | N-methylpiperidin-4-yl | hydrogen | 2-methylphenyl |
| 363 | methyl | N-methylpiperidin-4-yl | hydrogen | 4-methylphenyl |
| 364 | methyl | N-methylpiperidin-4-yl | hydrogen | 4-methoxyphenyl |
| 365 | methyl | N-methylpiperidin-4-yl | hydrogen | 4-(propane-sulfonyl)phenyl |
| 366 | methyl | N-methylpiperidin-4-yl | hydrogen | 3-benzo[1,3]dioxol-5-yl |
| 367 | methyl | N-methylpiperidin-4-yl | hydrogen | pyridin-2-yl |
| 368 | methyl | N-methylpiperidin-4-yl | hydrogen | pyridin-3-yl |
| 369 | methyl | morpholin-4-yl | hydrogen | phenyl |
| 370 | methyl | morpholin-4-yl | hydrogen | 4-fluorophenyl |
| 371 | methyl | morpholin-4-yl | hydrogen | 2-aminophenyl |
| 372 | methyl | morpholin-4-yl | hydrogen | 2-methylphenyl |
| 373 | methyl | morpholin-4-yl | hydrogen | 4-methylphenyl |
| 374 | methyl | morpholin-4-yl | hydrogen | 4-methoxyphenyl |
| 375 | methyl | morpholin-4-yl | hydrogen | 4-(propane-sulfonyl)phenyl |
| 376 | methyl | morpholin-4-yl | hydrogen | 3-benzo[1,3]dioxol-5-yl |
| 377 | methyl | morpholin-4-yl | hydrogen | pyridin-2-yl |
| 378 | methyl | morpholin-4-yl | hydrogen | pyridin-3-yl |
| 379 | methyl | N-acetylpiperidin-4-yl | hydrogen | phenyl |
| 380 | methyl | N-acetylpiperidin-4-yl | hydrogen | 4-fluorophenyl |
| 381 | methyl | N-acetylpiperidin-4-yl | hydrogen | 2-aminophenyl |
| 382 | methyl | N-acetylpiperidin-4-yl | hydrogen | 2-methylphenyl |
| 383 | methyl | N-acetylpiperidin-4-yl | hydrogen | 4-methylphenyl |
| 384 | methyl | N-acetylpiperidin-4-yl | hydrogen | 4-methoxyphenyl |
| 385 | methyl | N-acetylpiperidin-4-yl | hydrogen | 4-(propane-sulfonyl)phenyl |
| 386 | methyl | N-acetylpiperidin-4-yl | hydrogen | 3-benzo[1,3]dioxol-5-yl |
| 387 | methyl | N-acetylpiperidin-4-yl | hydrogen | pyridin-2-yl |
| 388 | methyl | N-acetylpiperidin-4-yl | hydrogen | pyridin-3-yl |
| 389 | methyl | piperidin-4-yl | methyl | phenyl |
| 390 | methyl | piperidin-4-yl | methyl | 4-fluorophenyl |
| 391 | methyl | piperidin-4-yl | methyl | 2-aminophenyl |
| 392 | methyl | piperidin-4-yl | methyl | 2-methylphenyl |
| 393 | methyl | piperidin-4-yl | methyl | 4-methylphenyl |
| 394 | methyl | piperidin-4-yl | methyl | 4-methoxyphenyl |
| 395 | methyl | piperidin-4-yl | methyl | 4-(propane-sulfonyl)phenyl |
| 396 | methyl | piperidin-4-yl | methyl | 3-benzo[1,3]dioxol-5-yl |
| 397 | methyl | piperidin-4-yl | methyl | pyridin-2-yl |
| 398 | methyl | piperidin-4-yl | methyl | pyridin-3-yl |
| 399 | methyl | N-methylpiperidin-4-yl | methyl | phenyl |
| 400 | methyl | N-methylpiperidin-4-yl | methyl | 4-fluorophenyl |
| 401 | methyl | N-methylpiperidin-4-yl | methyl | 2-aminophenyl |
| 402 | methyl | N-methylpiperidin-4-yl | methyl | 2-methylphenyl |
| 403 | methyl | N-methylpiperidin-4-yl | methyl | 4-methylphenyl |
| 404 | methyl | N-methylpiperidin-4-yl | methyl | 4-methoxyphenyl |
| 405 | methyl | N-methylpiperidin-4-yl | methyl | 4-(propane-sulfonyl)phenyl |
| 406 | methyl | N-methylpiperidin-4-yl | methyl | 3-benzo[1,3]dioxol-5-yl |
| 407 | methyl | N-methylpiperidin-4-yl | methyl | pyridin-2-yl |
| 408 | methyl | N-methylpiperidin-4-yl | methyl | pyridin-3-yl |
| 409 | methyl | morpholin-4-yl | methyl | phenyl |
| 410 | methyl | morpholin-4-yl | methyl | 4-fluorophenyl |
| 411 | methyl | morpholin-4-yl | methyl | 2-aminophenyl |
| 412 | methyl | morpholin-4-yl | methyl | 2-methylphenyl |
| 413 | methyl | morpholin-4-yl | methyl | 4-methylphenyl |
| 414 | methyl | morpholin-4-yl | methyl | 4-methoxyphenyl |
| 415 | methyl | morpholin-4-yl | methyl | 4-(propane-sulfonyl)phenyl |
| 416 | methyl | morpholin-4-yl | methyl | 3-benzo[1,3]dioxol-5-yl |
| 417 | methyl | morpholin-4-yl | methyl | pyridin-2-yl |
| 418 | methyl | morpholin-4-yl | methyl | pyridin-3-yl |
| 419 | methyl | N-acetylpiperidin-4-yl | methyl | phenyl |
| 420 | methyl | N-acetylpiperidin-4-yl | methyl | 4-fluorophenyl |
| 421 | methyl | N-acetylpiperidin-4-yl | methyl | 2-aminophenyl |
| 422 | methyl | N-acetylpiperidin-4-yl | methyl | 2-methylphenyl |
| 423 | methyl | N-acetylpiperidin-4-yl | methyl | 4-methylphenyl |

TABLE VII-continued

| No. | R² | R³ | R⁶ᵇ | R⁷ |
|---|---|---|---|---|
| 424 | methyl | N-acetylpiperidin-4-yl | methyl | 4-methoxyphenyl |
| 425 | methyl | N-acetylpiperidin-4-yl | methyl | 4-(propane-sulfonyl)phenyl |
| 426 | methyl | N-acetylpiperidin-4-yl | methyl | 3-benzo[1,3]dioxol-5-yl |
| 427 | methyl | N-acetylpiperidin-4-yl | methyl | pyridin-2-yl |
| 428 | methyl | N-acetylpiperidin-4-yl | methyl | pyridin-3-yl |

Utilizing intermediates such as compound 19, as a convenient starting point the analogs 349–428 and others encompassed within the description of this category can be suitably prepared by the procedure outlined herein below. In the following example, R¹ is 4-fluorophenyl, however, the formulator may suitably substitute any starting material compatible with this procedure, inter alia, methyl phenylacetate, methyl 4-chlorophenyl-acetate, and methyl 3-(trifluoromethyl)phenyl acetate.

Scheme VII: Preparation of Third Aspect of Category III

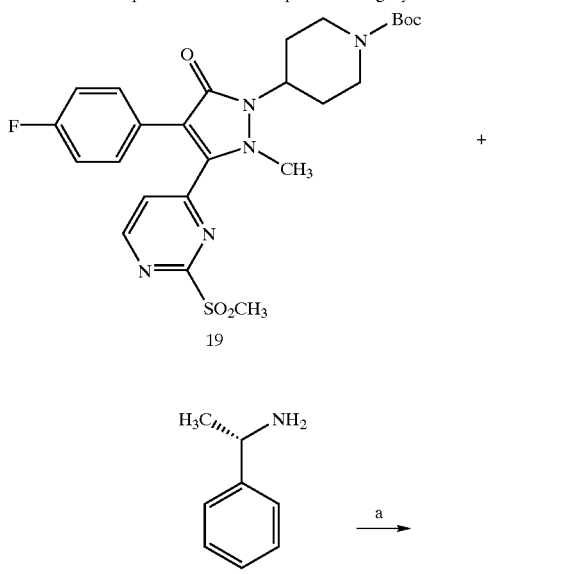

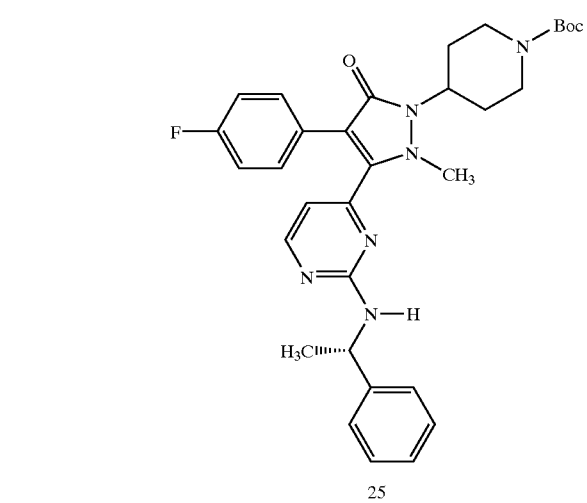

Reagents and conditions: (a) toluene; 90° C. 2hr.

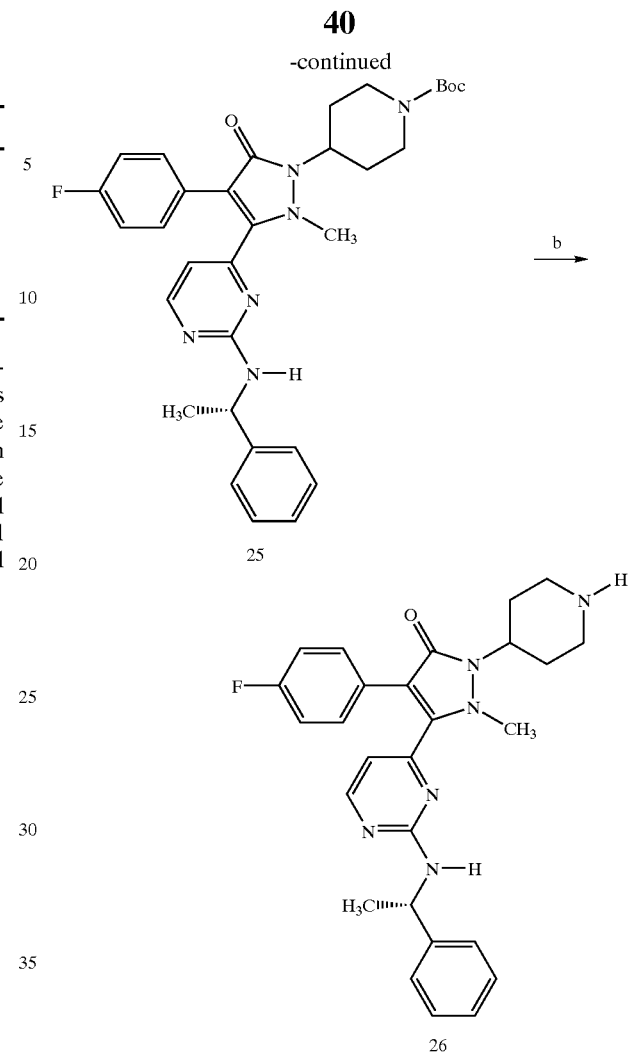

Reagents and conditions: (b) TFA, CH₂Cl₂; rt, 30 min.

EXAMPLE 7

4-(4-Fluorophenyl)-1-methyl-5-[2-(1-phenylethylamino)-pyrimidin-4-yl]-2-piperidin-4-yl-2-piperidin-4-yl-1,2-dihydropyrazol-3-one (27)

Preparation of 4-{4-(4-fluorophenyl)-2-methyl-5-oxo-3-[2-(1-phenylethylamino)-pyrimidin-4-yl]-2,5-dihydro-pyrazol-1-yl}-piperidine-1-carboxylic acid tert-butyl ester (26): To a solution of 4-[4-(4-fluorophenyl)-2-methyl-5-(2-methanesulfonyl-pyrimidin-4-yl)-3-oxo-2,3-dihydro-pyrazol-1-yl]-piperidine-1 carboxylic acid tert-butyl ester, 12, (6 g, 12 mmol) in toluene (30 mL) is added (S)-(α)-methylbenzyl amine (1.55 mL, 24 mmol). After stirring at 90° C. for 2 hours, the reaction mixture is cooled to room temperature and then concentrated in vacuo. Purification over silica (50% EtOAc in hexanes) affords 5.5 g (80% yield) of the desired product: ¹H NMR (300 MHz, CDCl₃) δ 8.41 (d, J=4.9 Hz, 1H), 7.38–7.31 (m, 7H), 6.98 (t, J=8.7 Hz, 2H), 6.40 (d, J=4.9 Hz, 1H), 4.40–4.31 (m, 1H), 4.19–4.08 (m, 1H), 2.86–2.78 (m, 4H), 2.23 (t, J=8 Hz, 2H), 1.91 (d, J=12.4 Hz, 2H), 1.60 (d, J=6.9 Hz, 3H), 1.52(s, 9H); ES/MS: 573.4 (M+H).

Preparation of 4-(4-fluorophenyl)-1-methyl-5-[2-(1-phenylethylamino)-pyrimidin-4-yl]-2-piperidin-4-yl-1,2-dihydropyrazol-3-one (27): To a solution of 4-{4-(4- fluorophenyl)-2-methyl-5-oxo-3-[2-(1-phenylethylamino)-pyrimidin-4-yl]-2,5-dihydro-pyrazol-1-yl}-piperidine-1-carboxylic acid tert-butyl ester, 26, (9 g, 15.7 mmol) in CH$_2$Cl$_2$ (90 mL) is added 20% TFA in CH$_2$Cl$_2$. After stirring at room temperature for 0.5 h, the reaction mixture is concentrated in vacuo. Purification by preparatory HPLC affords 4.2 9 (45% yield) of the desired product: [α]$_D$ −41.0° (c 1.7, MeOH); $^1$H NMR (300 MHz, CD$_3$OD) δ 8.25 (d, J=4.8 Hz, 1H), 7.40–7.00 (m, 9H), 6.40 (d, J=4.8 Hz, 1H), 5.11–5.05 (m, 1H), 4.51–4.41 (m, 1H), 3.61–3.55 (m, 2H), 3.33 (bd, J=1.5 Hz, 3H), 3.24–3.05 (m, 3H), 2.92–2.75 (m, 2H), 2.19–2.10 (m, 2H), 1.52 (d, J=6.9 Hz, 3H). HRMS calcd for C$_{27}$H$_{29}$FN$_6$O (M+H)$^+$473.2465; found 473.2460.

Non-limiting examples of other compounds comprising the third aspect of Category III include:

4-(4-Fluorophenyl)-5-[2-(S)-(α-methylbenzylamino)pyrimidin-4-yl]-1-methyl-2-piperidin-4-yl-1,2-dihydropyrazol-3-one;

4-(4-Fluorophenyl)-5-[2-(S)-(α-methylbenzylamino)pyrimidin-4-yl]-1-methyl-2-(N-acetyl)piperidin-4-yl-1,2-dihydropyrazol-3-one;

4-(4-Fluorophenyl)-5-[2-(S)-(α-methylbenzylamino)pyrimidin-4-yl]-1-methyl-2-(N-methyl)piperidin-4-yl-1,2-dihydropyrazol-3-one;

(4-{4-(4-Fluorophenyl)-2-methyl-5-oxo-3-[2-(S)-(α-methylbenzylamino)pyrimidin-4-yl]-2,5-dihydropyrazol-1-yl}piperidin-1-yl) acetic acid;

2-(4-{4-(4-Fluorophenyl)-2-methyl-5-oxo-3-[2-(S)-(α-methylbenzylamino)pyrimidin-4-yl]-2,5-dihydropyrazol-1-yl}piperidin-1-yl)-2-methyl propionic acid;

(4-{4-(4-Fluorophenyl)-2-methyl-5-oxo-3-[2-(S)-(α-methylbenzylamino)pyrimidin-4-yl]-2,5-dihydropyrazol-1-yl}piperidin-1-yl) acetic acid ethyl ester;

2-(4-{4-(4-Fluorophenyl)-2-methyl-5-oxo-3-[2-(S)-(α-methylbenzylamino)pyrimidin-4-yl]-2,5-dihydropyrazol-1-yl}piperidin-1-yl)-2-methyl propionic acid ethyl ester.

The fourth aspect of Category III inflammatory cytokine release inhibiting compounds according to the present invention are 4-fluorophenyl-5-(2-R-substituted-pyrimidin-4-yl)-1,2-dihydropyrazol-3-ones having the general scaffold with the formula:

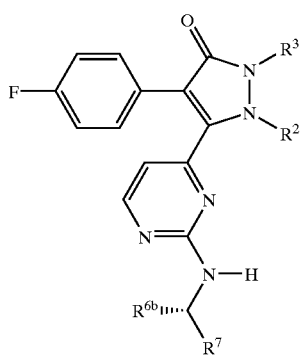

is R$^2$ C$_1$–C$_4$ alkyl, R$^7$ is substituted or unsubstituted C$_1$–C$_4$ alkyl, and R$^2$, R$^3$, R$^{6b}$, and R$^7$ are described herein below in Table VIII. The analogs described herein have the indicated stereochemistry when R$^{6b}$ is not hydrogen.

TABLE VIII

| No. | R$^2$ | R$^3$ | R$^{6b}$ | R$^7$ |
|---|---|---|---|---|
| 429 | methyl | piperidin-4-yl | hydrogen | hydrogen |
| 430 | methyl | piperidin-4-yl | hydrogen | methyl |
| 431 | methyl | piperidin-4-yl | hydrogen | ethyl |
| 432 | methyl | piperidin-4-yl | hydrogen | vinyl |
| 433 | methyl | piperidin-4-yl | hydrogen | cyclopropyl |
| 434 | methyl | piperidin-4-yl | hydrogen | cyclohexyl |
| 435 | methyl | piperidin-4-yl | hydrogen | methoxymethyl |
| 436 | methyl | piperidin-4-yl | hydrogen | methoxyethyl |
| 437 | methyl | piperidin-4-yl | hydrogen | 1-hydroxy-1-methylethyl |
| 438 | methyl | piperidin-4-yl | hydrogen | —CO$_2$H |
| 439 | methyl | N-methylpiperidin-4-yl | hydrogen | hydrogen |
| 440 | methyl | N-methylpiperidin-4-yl | hydrogen | methyl |
| 441 | methyl | N-methylpiperidin-4-yl | hydrogen | ethyl |
| 442 | methyl | N-methylpiperidin-4-yl | hydrogen | vinyl |
| 443 | methyl | N-methylpiperidin-4-yl | hydrogen | cyclopropyl |
| 444 | methyl | N-methylpiperidin-4-yl | hydrogen | cyclohexyl |
| 445 | methyl | N-methylpiperidin-4-yl | hydrogen | methoxymethyl |
| 446 | methyl | N-methylpiperidin-4-yl | hydrogen | methoxyethyl |
| 447 | methyl | N-methylpiperidin-4-yl | hydrogen | 1-hydroxy-1-methylethyl |
| 448 | methyl | N-methylpiperidin-4-yl | hydrogen | —CO$_2$H |
| 449 | methyl | morpholin-4-yl | hydrogen | hydrogen |
| 450 | methyl | morpholin-4-yl | hydrogen | methyl |
| 451 | methyl | morpholin-4-yl | hydrogen | ethyl |
| 452 | methyl | morpholin-4-yl | hydrogen | vinyl |
| 453 | methyl | morpholin-4-yl | hydrogen | cyclopropyl |
| 454 | methyl | morpholin-4-yl | hydrogen | cyclohexyl |
| 455 | methyl | morpholin-4-yl | hydrogen | methoxymethyl |
| 456 | methyl | morpholin-4-yl | hydrogen | methoxyethyl |
| 457 | methyl | morpholin-4-yl | hydrogen | 1-hydroxy-1-methylethyl |
| 458 | methyl | morpholin-4-yl | hydrogen | —CO$_2$H |
| 459 | methyl | N-acetylpiperidin-4-yl | hydrogen | hydrogen |
| 460 | methyl | N-acetylpiperidin-4-yl | hydrogen | methyl |
| 461 | methyl | N-acetylpiperidin-4-yl | hydrogen | ethyl |
| 462 | methyl | N-acetylpiperidin-4-yl | hydrogen | vinyl |
| 463 | methyl | N-acetylpiperidin-4-yl | hydrogen | cyclopropyl |
| 464 | methyl | N-acetylpiperidin-4-yl | hydrogen | cyclohexyl |
| 465 | methyl | N-acetylpiperidin-4-yl | hydrogen | methoxymethyl |
| 466 | methyl | N-acetylpiperidin-4-yl | hydrogen | methoxyethyl |
| 467 | methyl | N-acetylpiperidin-4-yl | hydrogen | 1-hydroxy-1-methylethyl |
| 468 | methyl | N-acetylpiperidin-4-yl | hydrogen | —CO$_2$H |
| 469 | methyl | piperidin-4-yl | methyl | hydrogen |
| 470 | methyl | piperidin-4-yl | methyl | methyl |
| 471 | methyl | piperidin-4-yl | methyl | ethyl |
| 472 | methyl | piperidin-4-yl | methyl | vinyl |
| 473 | methyl | piperidin-4-yl | methyl | cyclopropyl |
| 474 | methyl | piperidin-4-yl | methyl | cyclohexyl |
| 475 | methyl | piperidin-4-yl | methyl | methoxymethyl |
| 476 | methyl | piperidin-4-yl | methyl | methoxyethyl |
| 477 | methyl | piperidin-4-yl | methyl | 1-hydroxy-1-methylethyl |
| 478 | methyl | piperidin-4-yl | methyl | —CO$_2$H |
| 479 | methyl | N-methylpiperazin-4-yl | methyl | hydrogen |
| 480 | methyl | N-methylpiperazin-4-yl | methyl | methyl |
| 481 | methyl | N-methylpiperazin-4-yl | methyl | ethyl |
| 482 | methyl | N-methylpiperazin-4-yl | methyl | vinyl |
| 483 | methyl | N-methylpiperazin-4-yl | methyl | cyclopropyl |
| 484 | methyl | N-methylpiperazin-4-yl | methyl | cyclohexyl |
| 485 | methyl | N-methylpiperazin-4-yl | methyl | methoxymethyl |
| 486 | methyl | N-methylpiperazin-4-yl | methyl | methoxyethyl |
| 487 | methyl | N-methylpiperazin-4-yl | methyl | 1-hydroxy-1-methylethyl |
| 488 | methyl | N-methylpiperazin-4-yl | methyl | —CO$_2$H |
| 489 | methyl | morpholin-4-yl | methyl | hydrogen |
| 490 | methyl | morpholin-4-yl | methyl | methyl |
| 491 | methyl | morpholin-4-yl | methyl | ethyl |
| 492 | methyl | morpholin-4-yl | methyl | vinyl |
| 493 | methyl | morpholin-4-yl | methyl | cyclopropyl |
| 494 | methyl | morpholin-4-yl | methyl | cyclohexyl |
| 495 | methyl | morpholin-4-yl | methyl | methoxymethyl |
| 496 | methyl | morpholin-4-yl | methyl | methoxyethyl |

TABLE VIII-continued

| No. | R² | R³ | R⁶ᵇ | R⁷ |
|---|---|---|---|---|
| 497 | methyl | morpholin-4-yl | methyl | 1-hydroxy-1-methylethyl |
| 498 | methyl | morpholin-4-yl | methyl | —CO₂H |
| 499 | methyl | N-acetylpiperidin-4-yl | methyl | hydrogen |
| 500 | methyl | N-acetylpiperidin-4-yl | methyl | methyl |
| 501 | methyl | N-acetylpiperidin-4-yl | methyl | ethyl |
| 502 | methyl | N-acetylpiperidin-4-yl | methyl | vinyl |
| 503 | methyl | N-acetylpiperidin-4-yl | methyl | cyclopropyl |
| 504 | methyl | N-acetylpiperidin-4-yl | methyl | cyclohexyl |
| 505 | methyl | N-acetylpiperidin-4-yl | methyl | methoxymethyl |
| 506 | methyl | N-acetylpiperidin-4-yl | methyl | methoxyethyl |
| 507 | methyl | N-acetylpiperidin-4-yl | methyl | 1-hydroxy-1-methylethyl |
| 508 | methyl | N-acetylpiperidin-4-yl | methyl | —CO₂H |

Utilizing intermediates such as compound 19, as a convenient starting point the analogs 429–508 and others encompassed within the description of this category can be suitably prepared by the procedure outlined herein below. In the following example, R¹ is 4-fluorophenyl, however, the formulator may suitably substitute any starting material compatible with this procedure, inter alia, methyl phenylacetate, methyl 4-chlorophenyl-acetate, and methyl 3-(trifluoromethyl)phenyl acetate.

Scheme VIII: Preparation of Fourth Aspect of Category III

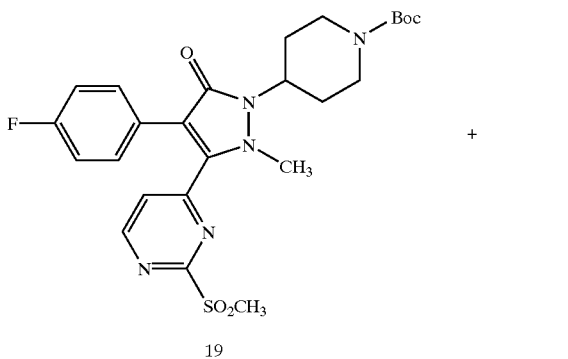

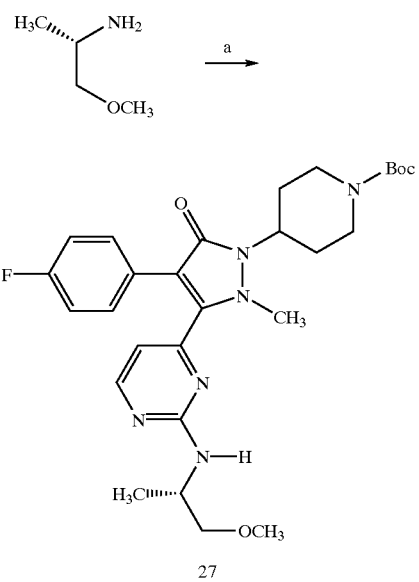

Reagents and conditions: (a) toluene; 90° C. 2 hr.

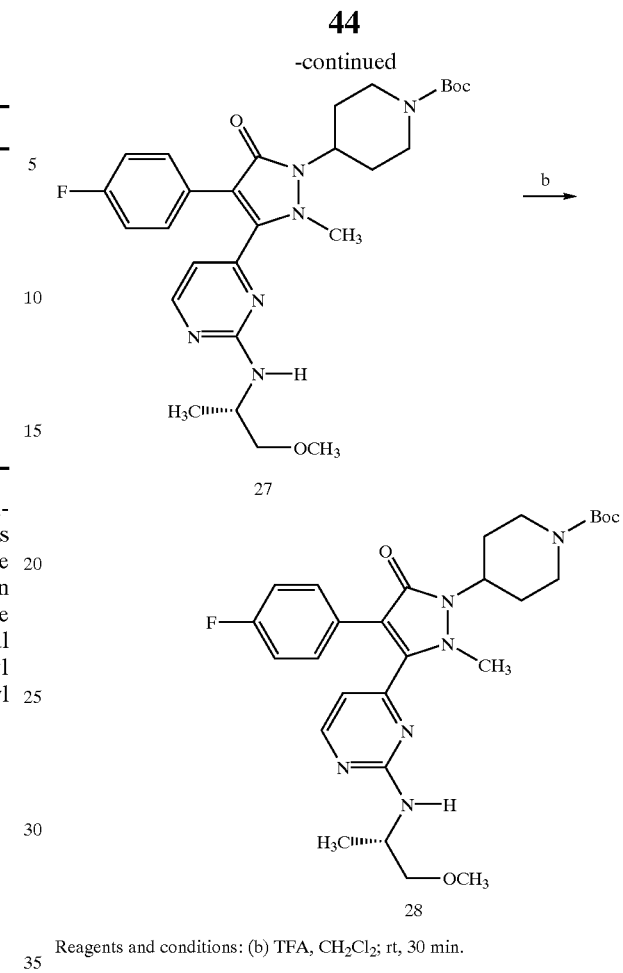

Reagents and conditions: (b) TFA, CH₂Cl₂; rt, 30 min.

EXAMPLE 8

4-(4-Fluorophenyl)-5-[2-(2-methoxy-1-(S)-methylethylamino)-pyrimidin-4-yl]-1-methyl-2-piperidin-4-yl-1,2-dihydropyrazol-3-one (28)

Preparation of 4-{4-(4-fluorophenyl)-3-[2-(2-methoxy-1-(S)-methylethylamino)-pyrimidin-4-yl]-2-methyl-5-oxo-2,5-dihydropyrazol-1-yl]-1-carboxylic acid tert-butyl ester (27): To a solution of 4-[4-(4-fluorophenyl)-2-methyl-3-(2-methanesulfonyl-pyrimidin-4-yl)-5-oxo-2,5-dihydro-pyrazol-1-yl]-piperidine-1 carboxylic acid tert-butyl ester, 19, (6 g, 12 mmol) in toluene (30 mL) is added (S)-2-amino-3-methoxypropane (2.14 g, 24 mmol). After stirring at 90° C. for 2 hours, the reaction mixture is cooled to room temperature and then concentrated in vacuo. Purification over silica (50% EtOAc/hexane) affords the desired product.

Preparation of 4-(4-fluorophenyl)-5-[2-(2-methoxy-1-(S)-methylethylamino)-pyrimidin-4-yl]-1-methyl-2-piperidin-4-yl-1,2-dihydropyrazol-3-one (28): To a solution of 4-{4-(4-fluorophenyl)-3-[2-(2-(S)-methoxy-1-methylethylamino)pyrimidin-4-yl]-2-methyl-5-oxo-2,5-dihydropyrazol-1-yl]-1-carboxylic acid tert-butyl ester, 27, (6.5 g, 12 mmol) in CH₂Cl₂ (90 mL) was added 20% TFA in CH₂Cl₂. After stirring at room temperature for 0.5 hour, the reaction mixture is concentrated in vacuo. Purification by preparatory HPLC affords the desired product as the trifluoroacetate salt. ¹H NMR (300 MHz, CD₃OD) δ 8.30 (d, J=4.8 Hz, 1H), 7.33–7.28 (m, 2H), 7.10–7.04 (m, 2H), 6.47 (d, J=4.8 Hz,1H), 4.55–4.47 (m, 1H), 4.24–4.18 (m, 1H), 3.62–3.53 (m, 2H), 3.45–3.26 (m, 9H), 3.23–3.14 (m, 2H), 2.93–2.78 (m, 2H), 2.20–2.13 (m, 2H), 1.21 (d, J=6.6 Hz, 3H). HRMS calcd for $C_{23}H_{29}FN_6O_2$ (M+H)$^+$441.2414; found 441.2425.

Non-limiting examples of other compounds comprising the second aspect of Category IV include:

4-(4-fluorophenyl)-5-[2-(S)-(1,2-dimethyl-2-hydroxypropylamino)pyrimidin-4-yl]-1-methyl-2-piperidin-4-yl-1,2-dihydropyrazol-3-one.

The compounds which comprise Category IV analogs of the present invention are 4-$R^1$-substituted-5-(2-R-substituted-pyrimidin-4-yl)-1,2-dihydropyrazol-3-ones having the general scaffold with the formula:

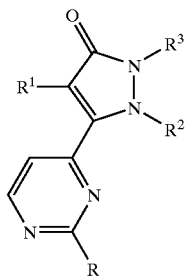

wherein the first aspect of Category IV has the formula:

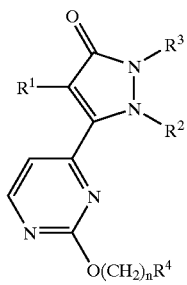

$R^2$ and $R^3$ are the same $C_1$–$C_4$ linear, branched, or cyclic alkyl and $R^1$, $R^2$, $R^3$ and $R^4$ are described herein below in Table IX. The index n can be 0 or 1.

| No. | $R^1$ | $R^2/R^3$ | $R^4$ |
|---|---|---|---|
| 509 | 4-fluorophenyl | methyl | phenyl |
| 510 | 4-fluorophenyl | methyl | 2-fluorophenyl |
| 511 | 4-fluorophenyl | methyl | 3-fluorophenyl |
| 512 | 4-fluorophenyl | methyl | 4-fluorophenyl |
| 513 | 4-fluorophenyl | methyl | 2,6-difluorophenyl |
| 514 | 4-fluorophenyl | methyl | 2-cyanophenyl |
| 515 | 4-fluorophenyl | methyl | 3-cyanophenyl |
| 516 | 4-fluorophenyl | methyl | 2-trifluoromethylphenyl |
| 517 | 4-fluorophenyl | methyl | 4-trifluoromethylphenyl |
| 518 | 4-fluorophenyl | methyl | N-methylpiperadin-4-yl |
| 519 | 4-fluorophenyl | methyl | 4-methylphenyl |
| 520 | 4-fluorophenyl | methyl | 2,4-dimethylphenyl |
| 521 | 4-fluorophenyl | methyl | 3-N-acetylaminophenyl |
| 522 | 4-fluorophenyl | methyl | pyran-4-yl |
| 523 | 4-fluorophenyl | methyl | 4-methoxyphenyl |
| 524 | 4-fluorophenyl | methyl | 3-benzo[1,3]dioxol-5-yl |
| 525 | 4-fluorophenyl | ethyl | phenyl |
| 526 | 4-fluorophenyl | ethyl | 2-fluorophenyl |
| 527 | 4-fluorophenyl | ethyl | 3-fluorophenyl |
| 528 | 4-fluorophenyl | ethyl | 4-fluorophenyl |
| 529 | 4-fluorophenyl | ethyl | 2,6-difluorophenyl |
| 530 | 4-fluorophenyl | ethyl | 2-cyanophenyl |
| 531 | 4-fluorophenyl | ethyl | 3-cyanophenyl |
| 532 | 4-fluorophenyl | ethyl | 2-trifluoromethylphenyl |
| 533 | 4-fluorophenyl | ethyl | 4-trifluoromethylphenyl |
| 534 | 4-fluorophenyl | ethyl | N-methylpiperadin-4-yl |
| 535 | 4-fluorophenyl | ethyl | 4-methylphenyl |
| 536 | 4-fluorophenyl | ethyl | 2,4-dimethylphenyl |
| 537 | 4-fluorophenyl | ethyl | 3-N-acetylaminophenyl |
| 538 | 4-fluorophenyl | ethyl | pyran-4-yl |
| 539 | 4-fluorophenyl | ethyl | 4-methoxyphenyl |
| 540 | 4-fluorophenyl | ethyl | 3-benzo[1,3]dioxol-5-yl |

Utilizing intermediates such as compound 3, as a convenient starting point the analogs 509–540 and others encompassed within the description of this category can be suitably prepared by the procedure outlined herein below. In the following example the formulator may suitably substitute any starting material compatible with this procedure, inter alia, methyl phenylacetate, methyl 4-chlorophenyl-acetate, and methyl 3-(trifluoromethyl)phenyl acetate. In addition, other alkyl hydrazines, for example, 1,2-diethylhydrazine dihydrochloride, can be substituted for 1,2-dimethylhydrazine dihydrochloride.

Scheme IX: Preparation of First Aspect of Category IV

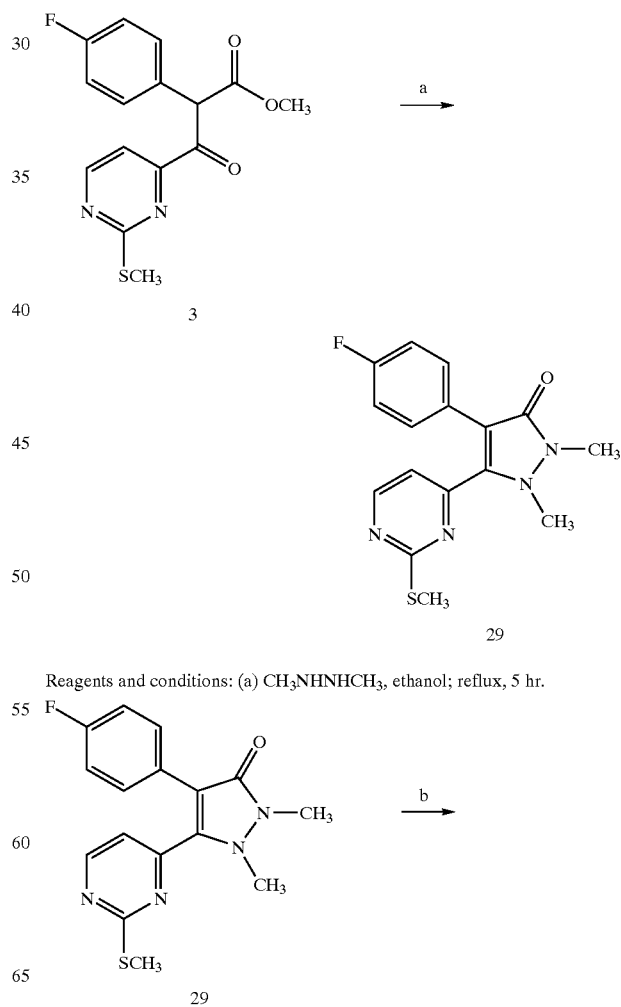

Reagents and conditions: (a) $CH_3NHNHCH_3$, ethanol; reflux, 5 hr.

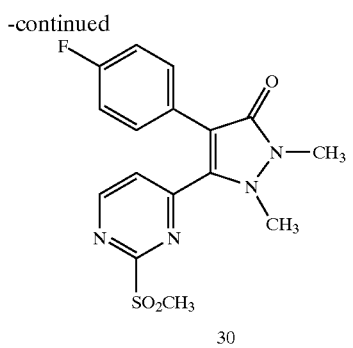

Reagents and conditions: (b) Oxone®, MeOH/THF/H2O; rt, 5 hr.

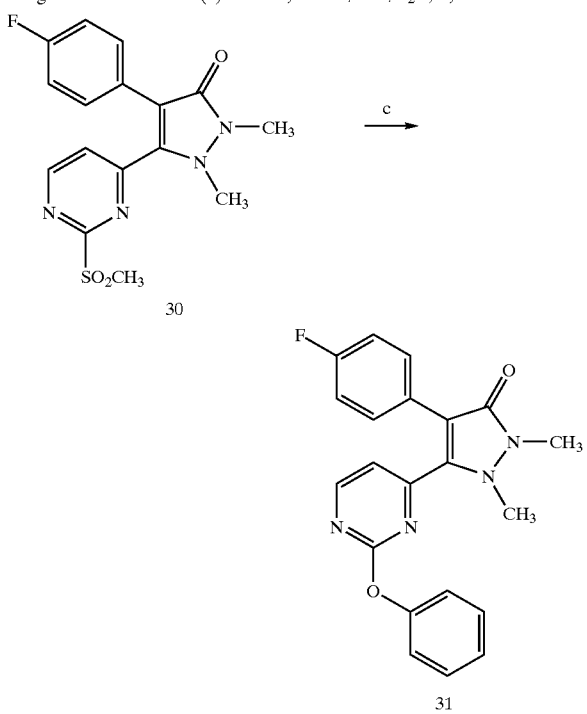

Reagents and conditions: (c) phenol, NaH, THF; rt, 14 hr.

EXAMPLE 9

4-(4-Fluorophenyl)-1,2-dimethyl-5-(2-phenoxypyrimidin-4-yl)-1,2-dihydropyrazol-3-one (31)

Preparation of 4-(4-fluorophenyl)-1,2-dimethyl-5-(2-methylsulfanyl-pyrimidin-4-yl)-1,2-dihydropyrazol-3-one (29): To a solution of 4 (4.0 g, 12.5 mmol) in ethanol (60 mL) was added 1,2-dimethylhydrazine dihydrochloride (2.5g, 18.8 mmol). After refluxing the mixture at 78° C. for 5 days, the solution was cooled to room temp. and partitioned between EtOAc (100 mL) and aqueous saturated NaHCO$_3$ solution (100 mL). The organic phase was separated, dried (MgSO$_4$), filtered and concentrated in vacuo. The crude residue was purified by silica gel chromatography (biotage system) (5% EtOAc/hexanes) to yield 1.4 g (33%) of 5 as a yellow solid: $^1$H NMR (300 MHz, CDCl$_3$) δ 8.49 (d, J=5.1 Hz, 2H), 7.31–7.36 (m, 2H), 6.83–7.05 (m, 2H), 6.83 (d, J=5.1 Hz, 1H), 3.55 (s, 3H), 3.40 (s, 3H), 2.60 (s, 3H); MS-ESI m/z 330 (M+H)$^+$.

Preparation of 4-(4-fluorophenyl)-1,2-dimethyl-5-(2-methanesulfonyl-pyrimidin-4-yl)-1,2-dihydropyrazol-3-one (30): To a solution 2-(4-fluorophenyl)-3-(2-methylsulfanyl-pyrimidin-4-yl)-3-oxo-propionic acid methyl ester, 3, (1.4 g, 4.1 mmol) in THF (25 mL) and MeOH (25 mL) is added dropwise a solution of Oxone® (10.1 g, 16.4 mmol) in water (40 mL). After stirring at room temperature for 5 hours, the reaction mixture is concentrated in vacuo. The resulting residue is diluted with CH$_2$Cl$_2$ (150 mL) and washed with aqueous saturated NaHCO$_3$ solution (2×50 mL). The aqueous phase is extracted with CH$_2$Cl$_2$ (3×50 mL) and the combined organic phases dried (MgSO$_4$), filtered and concentrated in vacuo to afford 1.1 g (72% yield) of the desired product as a yellow solid which is used without further purification: MS-ESI m/z 363 [M+H]$^+$.

Preparation of 4-(4-fluorophenyl)-1,2-dimethyl-5-(2-phenoxypyrimidin-4-yl)-1,2-dihydropyrazol-3-one (31): To a solution of phenol (0.12 g, 1.29 mmol) in THF (5 mL) is added sodium hydride (0.04 g, 1.08 mmol). After stirring at room temperature for 10 min, a solution of 4-(4-fluorophenyl)-1,2-dimethyl-5-(2-methanesulfonyl-pyrimidin-4-yl)-1,2-dihydropyrazol-3-one, 30, (0.20 g, 0.55 mmol) in THF (5 mL) is added to the reaction mixture. The mixture is stirred at room temperature for 4 hours. The reaction is then quenched with H$_2$O and diluted with EtOAc. The organic phase is washed with 1N NaOH (×2), dried (MgSO$_4$), filtered and concentrated in vacuo. The crude residue is purified by preparatory HPLC to the desired product: $^1$H NMR (300 MHz, CDCl$_3$) δ 8.51 (d, J=4.8 Hz, 1H), 7.48 (t, J=8.1 Hz, 2H), 7.36–7.31 (m, 3H), 7.24 (dd, J=7.5, 1.2 Hz, 2H), 7.04 (t, J=9.0 Hz, 2H), 6.94 (d, J=5.1 Hz, 1H), 3.53 (s, 3H), 3.38 (s, 3H); HRMS calcd for C$_{21}$H$_{18}$FN$_4$O$_2$ (M+H)$^+$377.1418; found 377.1397.

1,2-Diethyl-4-(4-fluorophenyl)-5-(2-phenoxypyrimidin-4-yl)-1,2-dihydropyrazol-3-one; $^1$H NMR (300 MHz, CDCl$_3$) δ 8.50 (d, J=4.9 Hz, 1H), 7.51–7.24 (m, 7H), 7.03 (t, J=8.8 Hz, 2H), 6.94 (d, J=8.8 Hz, 1H), 4.01 (q, J=7.1 Hz, 2H), 3.90 (q, J=6.9 Hz, 2H), 1.32 (t, J=7.1 Hz, 3H), 0.883 (t, J=6.9 Hz, 3H); MS-ESI m/z405 [M+H]$^+$; HRMS m/z calcd for C$_{23}$H$_{22}$FN$_4$O$_2$ [M+H$^+$] 405.1727, found 405.1715.

The second aspect of Category IV inflammatory cytokine release inhibiting compounds

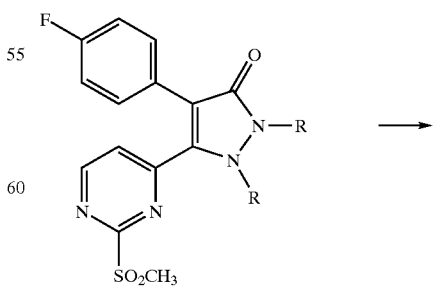

7 (R = Me)
8 (R = Et)

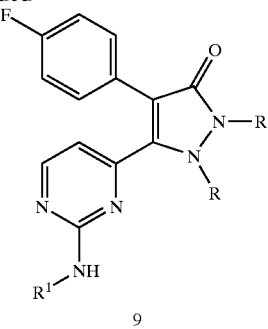

9 according to the present invention are 4-fluorophenyl-5-(2-R-substituted-pyrimidin-4-yl)-1,2-dihydropyrazol-3-ones having the general scaffold with the formula:

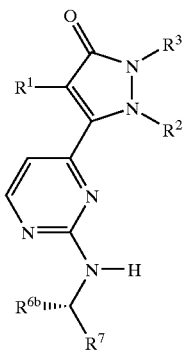

$R^2$ and $R^3$ are the same $C_1$–$C_4$ linear, branched, or cyclic alkyl and $R^2$, $R^3$, $R^{6b}$, and $R^7$ are described herein below in Table X. The analogs described herein have the indicated stereochemistry when $R^{6b}$ is not hydrogen.

TABLE X

| No. | $R^1$ | $R^2/R^3$ | $R^{6b}$ | $R^7$ |
|---|---|---|---|---|
| 541 | 4-fluorophenyl | methyl | hydrogen | phenyl |
| 542 | 4-fluorophenyl | methyl | hydrogen | 4-fluorophenyl |
| 543 | 4-fluorophenyl | methyl | hydrogen | 2-aminophenyl |
| 544 | 4-fluorophenyl | methyl | hydrogen | 2-methylphenyl |
| 545 | 4-fluorophenyl | methyl | hydrogen | 4-methylphenyl |
| 546 | 4-fluorophenyl | methyl | hydrogen | 4-methoxyphenyl |
| 547 | 4-fluorophenyl | methyl | hydrogen | 4-(propanesulfonyl)phenyl |
| 548 | 4-fluorophenyl | methyl | hydrogen | 3-benzo[1,3]dioxol-5-yl |
| 549 | 4-fluorophenyl | methyl | hydrogen | pyridin-2-yl |
| 550 | 4-fluorophenyl | methyl | hydrogen | pyridin-3-yl |
| 551 | 4-fluorophenyl | methyl | methyl | phenyl |
| 552 | 4-fluorophenyl | methyl | methyl | 4-fluorophenyl |
| 553 | 4-fluorophenyl | methyl | methyl | 2-aminophenyl |
| 554 | 4-fluorophenyl | methyl | methyl | 2-methylphenyl |
| 555 | 4-fluorophenyl | methyl | methyl | 4-methylphenyl |
| 556 | 4-fluorophenyl | methyl | methyl | 4-methoxyphenyl |
| 557 | 4-fluorophenyl | methyl | methyl | 4-(propanesulfonyl)phenyl |
| 558 | 4-fluorophenyl | methyl | methyl | 3-benzo[1,3]dioxol-5-yl |
| 559 | 4-fluorophenyl | methyl | methyl | pyridin-2-yl |
| 560 | 4-fluorophenyl | methyl | methyl | pyridin-3-yl |
| 561 | 4-fluorophenyl | methyl | hydrogen | H |
| 562 | 4-fluorophenyl | methyl | hydrogen | methyl |
| 563 | 4-fluorophenyl | methyl | hydrogen | ethyl |
| 564 | 4-fluorophenyl | methyl | hydrogen | vinyl |
| 565 | 4-fluorophenyl | methyl | hydrogen | cyclopropyl |
| 566 | 4-fluorophenyl | methyl | hydrogen | cyclohexyl |
| 567 | 4-fluorophenyl | methyl | hydrogen | methoxymethyl |
| 568 | 4-fluorophenyl | methyl | hydrogen | methoxyethyl |

TABLE X-continued

| No. | $R^1$ | $R^2/R^3$ | $R^{6b}$ | $R^7$ |
|---|---|---|---|---|
| 569 | 4-fluorophenyl | methyl | hydrogen | 1-hydroxy-1-methylethyl |
| 570 | 4-fluorophenyl | methyl | hydrogen | —$CO_2H$ |
| 571 | 4-fluorophenyl | methyl | methyl | H |
| 572 | 4-fluorophenyl | methyl | methyl | methyl |
| 573 | 4-fluorophenyl | methyl | methyl | ethyl |
| 574 | 4-fluorophenyl | methyl | methyl | vinyl |
| 575 | 4-fluorophenyl | methyl | methyl | cyclopropyl |
| 576 | 4-fluorophenyl | methyl | methyl | cyclohexyl |
| 577 | 4-fluorophenyl | methyl | methyl | methoxymethyl |
| 578 | 4-fluorophenyl | methyl | methyl | methoxyethyl |
| 579 | 4-fluorophenyl | methyl | methyl | 1-hydroxy-1-methylethyl |
| 580 | 4-fluorophenyl | methyl | methyl | —$CO_2H$ |
| 581 | 4-fluorophenyl | ethyl | hydrogen | phenyl |
| 582 | 4-fluorophenyl | ethyl | hydrogen | 4-fluorophenyl |
| 583 | 4-fluorophenyl | ethyl | hydrogen | 2-aminophenyl |
| 584 | 4-fluorophenyl | ethyl | hydrogen | 2-methylphenyl |
| 585 | 4-fluorophenyl | ethyl | hydrogen | 4-methylphenyl |
| 586 | 4-fluorophenyl | ethyl | hydrogen | 4-methoxyphenyl |
| 587 | 4-fluorophenyl | ethyl | hydrogen | 4-(propanesulfonyl)phenyl |
| 588 | 4-fluorophenyl | ethyl | hydrogen | 3-benzo[1,3]dioxol-5-yl |
| 589 | 4-fluorophenyl | ethyl | hydrogen | pyridin-2-yl |
| 590 | 4-fluorophenyl | ethyl | hydrogen | pyridin-3-yl |
| 591 | 4-fluorophenyl | ethyl | methyl | phenyl |
| 592 | 4-fluorophenyl | ethyl | methyl | 4-fluorophenyl |
| 593 | 4-fluorophenyl | ethyl | methyl | 2-aminophenyl |
| 594 | 4-fluorophenyl | ethyl | methyl | 2-methylphenyl |
| 595 | 4-fluorophenyl | ethyl | methyl | 4-methylphenyl |
| 596 | 4-fluorophenyl | ethyl | methyl | 4-methoxyphenyl |
| 597 | 4-fluorophenyl | ethyl | methyl | 4-(propanesulfonyl)phenyl |
| 598 | 4-fluorophenyl | ethyl | methyl | 3-benzo[1,3]dioxol-5-yl |
| 599 | 4-fluorophenyl | ethyl | methyl | pyridin-2-yl |
| 600 | 4-fluorophenyl | ethyl | methyl | pyridin-3-yl |
| 601 | 4-fluorophenyl | ethyl | hydrogen | H |
| 602 | 4-fluorophenyl | ethyl | hydrogen | methyl |
| 603 | 4-fluorophenyl | ethyl | hydrogen | ethyl |
| 604 | 4-fluorophenyl | ethyl | hydrogen | vinyl |
| 605 | 4-fluorophenyl | ethyl | hydrogen | cyclopropyl |
| 606 | 4-fluorophenyl | ethyl | hydrogen | cyclohexyl |
| 607 | 4-fluorophenyl | ethyl | hydrogen | methoxymethyl |
| 608 | 4-fluorophenyl | ethyl | hydrogen | methoxyethyl |
| 609 | 4-fluorophenyl | ethyl | hydrogen | 1-hydroxy-1-methylethyl |
| 610 | 4-fluorophenyl | ethyl | hydrogen | —$CO_2H$ |
| 611 | 4-fluorophenyl | ethyl | methyl | H |
| 612 | 4-fluorophenyl | ethyl | methyl | methyl |
| 613 | 4-fluorophenyl | ethyl | methyl | ethyl |
| 614 | 4-fluorophenyl | ethyl | methyl | vinyl |
| 615 | 4-fluorophenyl | ethyl | methyl | cyclopropyl |
| 616 | 4-fluorophenyl | ethyl | methyl | cyclohexyl |
| 617 | 4-fluorophenyl | ethyl | methyl | methoxymethyl |
| 618 | 4-fluorophenyl | ethyl | methyl | methoxyethyl |
| 619 | 4-fluorophenyl | ethyl | methyl | 1-hydroxy-1-methylethyl |
| 620 | 4-fluorophenyl | ethyl | methyl | —$CO_2H$ |

Utilizing intermediates such as compound 30, as a convenient starting point the analogs 540–620 and others encompassed within the description of this category can be suitably prepared by the procedure outlined herein below. In the following example the formulator may suitably substitute any starting material compatible with this procedure, inter alia, methyl phenylacetate, methyl 4-chlorophenylacetate, and methyl 3-(trifluoromethyl)phenyl acetate. In addition, other alkyl hydrazines, for example, 1,2-diethylhydrazine dihydrochloride, can be substituted for 1,2-dimethylhydrazine dihydrochloride.

Scheme X: Preparation of Second Aspect of Category IV

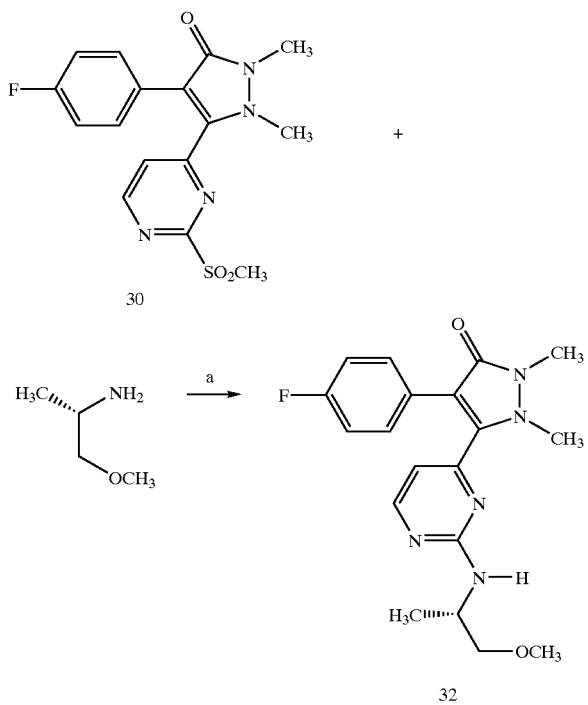

Reagents and conditions: (a) toluene; 140° C., 2 hr.

EXAMPLE 10

4-(4-Fluorophenyl)-1,2-dimethyl-5-(2-methoxy-1-(S)-methylethylamino)-pyrimidin-4-yl]-)-1,2-dihydropyrazol-3-one (32)

Preparation of 4-(4-Fluorophenyl)-1,2-dimethyl-5-(2-methoxy-1-(S)-methylethylamino)-pyrimidin-4-yl]-)-1,2-dihydropyrazol-3-one (32): To a solution of 4-(4-fluorophenyl)-1,2-dimethyl-5-(2-methanesulfonyl-pyrimidin-4-yl)-1,2-dihydropyrazol-3-one, 30, (0.20 g, 0.55 mmol) in toluene (5 mL) is added (S)-2-amino-3-methoxypropane (2.14 g, 24 mmol). The reaction is refluxed at 140° C. for 2 hours then concentrated in vacuo. The crude residue is purified by preparative HPLC to afford 66 mg (43% yield) of the desired product as a yellow solid: $[\alpha]^{25}_D$=−22° (c 0.14, MeOH); $^1$H NMR (300 MHz, CDCl$_3$) δ 8.25 (d, J=5.1 Hz, 1H), 7.41–7.35 (m, 2H), 7.03–6.96 (m, 2H), 6.41 (d, J=4.8 Hz, 1H), 5.57 (d, J=7.8 Hz, 1H), 4.29–4.24 (m, 1H), 3.52 (s, 3H) 3.46 (m, 2H), 3.40 (s, 3H) 3.35 (s, 3H), 1.29 (d, J=6.6, 3H); MS-ESI m/z 372 [M+H]$^+$. HRMS m/z calcd for $C_{19}H_{23}FN_5O_2$ [M+H$^+$] 372.1836, found 372.1824.

1,2-Dimethyl-4-(4-fluorophenyl)-5-[2-(S)-(α-methylbenzylamino)pyrimidin-4-yl]-1,2-dihydropyrazol-3-one; $[\alpha]^{25}_D$=−3° (c0.17, MeOH); $^1$H NMR (300 MHz, CDCl$_3$) δ 8.28 (d, J=4.9 Hz, 1H), 7.35–7.30 (m, 2H), 7.05 (t, J=8.8 Hz, 2H), 6.46 (d, J=4.8 Hz, 1H), 4.02 (m, 1H), 3.61 (s, 3H), 3.57 (s, 3H), 1.24 (s, 3H), 1.23 (s, 3H), 1.21 (d, J=6.9 Hz, 3H); MS-ESI m/z 386 [M+H$^+$]; HRMS m/z calcd for $C_{20}H_{25}FN_5O_2$ [M+H$^+$] 386.1992, found 386.1977.

1,2-Dimethyl-4-(4-fluorophenyl)-5-{2-(S)—[1-(4-fluorophenyl)ethylamino]pyrimidin-4-yl}-1,2-dihydropyrazol-3-one; $[\alpha]^{25}_D$=−78° (c 0.18, MeOH); $^1$H NMR (300 MHz, CDCl$_3$) δ 8.23 (d, J=4.8 Hz, 1H), 7.40–7.29 (m, 4H), 7.08–6.96 (m, 4H), 5.81 (br s, 1H), 5.18–5.13 (m, 1H), 3.49 (s, 3H), 3.06 (br s, 3H), 1.59 (d, J=6.9 Hz, 3H); MS-ESI m/z 422 [M+H$^+$]; HRMS m/z calcd for $C_{23}H_{22}F_2N_5O$ [M+H$^+$] 422.1792, found 422.1788.

1,2-Dimethyl-4-(4-fluorophenyl)-5-[2-(S)-(1-methylpropylamino)pyrimidin-4-yl]-1,2-dihydro-pyrazol-3-one; $[\alpha]^{25}_D$=+14° (c 0.185, MeOH); $^1$H NMR (300 MHz, CDCl$_3$) δ 8.26 (s, 1H), 7.35 (m, 2H), 7.01 (t, J=8.7, 2H), 6.41 (d, J=4.8 Hz, 1H), 4.03 (m, 1H), 3.53 (s, 3H), 3.36 (s, 3H) 1.25 (d, J=6.3 Hz, 3H), 1.0 (t, J=7.5, 3H); MS-APCI m/z 356 [M+H]$^+$. HRMS m/z calcd for $C_{19}H_{23}FN_5O$ [M+H$^+$] 356.1887, found 356.1883.

1,2-Dimethyl-4-(4-fluorophenyl)-5-[2-(S)-(1,2-dimethyl-2-hydroxypropylamino)-pyrimidin-4-yl]-1,2-dihydro-pyrazol-3-one; $^1$H NMR (300 MHz, CDCl$_3$) δ 8.28 (d, J=5.1 Hz, 1H), 7.36 (dd, J=5.5, 8.8 Hz, 2H), 6.97 (t, J=8.8 Hz, 2H), 6.49 (d, J=4.8 Hz, 1H), 3.95 (br s, 1H), 3.80 (m, 2H), 3.53 (s, 3H), 3.33 (s, 3H), 3.04–2.89 (m, 2H), 3.95–2.89 (m, 2H), 2.31–2.02 (m, 2H), 1.95–1.83 (m, 2H), 1.10 (t, J=7.5 Hz, 3H); MS-ESI m/z 489 [M+H]$^+$; HRMS m/z calcd for $C_{23}H_{30}FN_6O_3S$ [M+H$^+$] 488.2084, found 489.2086.

1,2-Dimethyl-4-(4-fluorophenyl)-5-[2-(S)-(1-methyl-2-methoxyethylamino)pyrimidin-4-yl]-1,2-dihydropyrazol-3-one; $[\alpha]^{25}_D$=−22° (c 0.14, MeOH); $^1$H NMR (300 MHz, CDCl$_3$) δ 8.25 (d, J=5.1 Hz, 1H), 7.41–7.35 (m, 2H), 7.03–6.96 (m, 2H), 6.41 (d, J=4.8 Hz, 1H), 5.57 (d, J=7.8 Hz, 1H), 4.29–4.24 (m, 1H), 3.52 (s, 3H) 3.46 (m, 2H), 3.40 (s, 3H) 3.35 (s, 3H), 1.29 (d, J=6.6, 3H); MS-ESI m/z 372 [M+H]$^+$. HRMS m/z calcd for $C_{19}H_{23}FN_5O_2$ [M+H$^+$] 372.1836, found 372.1824.

1,2-Dimethyl-4-(4-fluorophenyl)-5-[2-(isopropylamino)pyrimidin-4-y]-1,2-dihydropyrazol-3-one; $[\alpha]^{25}_D$=−22° (c 0.14, MeOH); $^1$H NMR (300 MHz, CDCl$_3$) δ 8.25 (d, J=5.1 Hz, 1H), 7.41–7.35 (m, 2H), 7.03–6.96 (m, 2H), 6.41 (d, J=4.8 Hz, 1H), 5.57 (d, J=7.8 Hz, 1H), 4.29–4.24 (m, 1H), 3.52 (s, 3H) 3.46 (m, 2H), 3.40 (s, 3H) 3.35 (s, 3H), 1.29 (d, J=6.6, 3H); MS-ESI m/z 372 [M+H]$^+$. HRMS m/z calcd for $C_{19}H_{23}FN_5O_2$ [M+H$^+$] 372.1836, found 372.1824.

1,2-Dimethyl-4-(4-fluorophenyl)-5-[2-(pyridin-4-ylamino)pyrimidin-4-yl]-1,2-dihydropyrazol-3-one; $^1$H NMR (300 MHz, CD$_3$OD) δ 8.47 (d, J=6.0 Hz, 2H), 8.32 (d, J=4.9 Hz, 1H), 7.41 (d, J=5.3 Hz, 1H), 7.27 (m, 2H), 7.03 (t, J=8.8 Hz, 2H), 6.51 (d, J=4.9 Hz, 1H), 3.57 (s, 3H), 3.34 (s, 3H); MS-ESI m/z 391 [M+H$^+$]; HRMS m/z calcd for $C_{21}H_{20}FN_6O$ [M+H$^+$] 391.1683, found 391.1668.

1,2-Dimethyl-4-(4-fluorophenyl)-5-[2-(pyridin-3-ylamino)pyrimidin-4-y]-1,2-dihydropyrazol-3-one; $^1$H NMR (300 MHz, CDCl$_3$) δ 8.62 (d, J=5.9 Hz, 1H), 8.32 (d, J=4.9 Hz, 1H), 7.71 (m, 1H), 7.38 (m, 2H), 7.26 (m, 1H), 6.99 (t, J=8.8 Hz, 2H), 6.52 (m, 1H), 6.46 (d, J=4.9 Hz, 1H), 4.79 (d, J=5.1 Hz, 2H), 3.52 (s, 3H), 3.30 (s, 3H); MS-ESI m/z 391[M+H]$^+$; HRMS m/z calcd for $C_{21}H_{20}FN_6O$ [M+H$^+$] 391.1683, found 391.1684.

1,2-Dimethyl-4-(4-fluorophenyl)-5-[2-(pyridin-2-ylamino)pyrimidin-4-yl]-1,2-dihydropyrazol-3-one; $^1$H NMR (300 MHz, CDCl$_3$) δ 8.62 (d, J=4.0 Hz, 1H), 8.32 (d, J=5.1 Hz, 1H), 7.71 (dt, J=1.5, 7.7 Hz, 1H), 7.61–7.60 (m, 1H), 7.41–7.32 (m, 2H), 7.29–7.23 (m, 1H), 7.00 (t, J=8.8 Hz, 2H), 6.55 (br s, 1H), 6.47 (d, J=4.9 Hz, 1H), 4.80 (d, J=5.1 Hz, 2H), 3.53 (s, 3H), 3.31 (br s, 3H); MS-ESI m/z 391 [M+H$^+$]; HRMS m/z calcd for $C_{21}H_{20}FN_6O$ [M+H$^+$] 391.1683, found 391.1672.

1,2-Diethyl-4-(4-fluorophenyl)-5-[2-(S)-(α-methylbenzylamino)pyrimidin-4-y]-1,2-dihydro-pyrazol-3-one; $[\alpha]^{25}_D$=+74° (c0.035, MeOH); $^1$H NMR (300 MHz, CDCl$_3$) δ 8.23 (d, J=5.1 Hz, 1H), 7.42–7.29 (m, 2H), 7.69 (t, J=8.8 Hz, 2H), 6.43 (d, J=5.1 Hz, 1H), 5.33 (m, 1H), 4.15 (m, 1H), 4.05–3.75 (br s, 2H), 3.75–3.34 (br s, 2H), 1.61 (s, 3H), 1.33–1.28 (m, 6H); MS-ESI m/z 432 [M+H]$^+$; HRMS m/z calcd for C$_{25}$H$_{27}$FN$_5$O [M+H$^+$] 432.2200, found 432.2182.

1,2-Diethyl-4-(4-fluorophenyl)-5-[2-(S)-(1-methyl-2-methoxyethylamino)pyrimidin-4-yl]-1,2-dihydropyrazol-3-one; [α]$^{25}_D$=+58° (c 0.105, MeOH); $^1$H NMR (300 MHz, CDCl$_3$) δ 8.26 (d, J=5.1 Hz, 1H), 7.40 (dd, J=5.5, 8.8 Hz, 2H), 7.00 (t, J=8.8 Hz, 2H), 6.45 (d, J=5.1 Hz, 1H), 5.68 (br s, 1H), 4.29 (m, 1H), 4.01 (q, J=7.1 Hz, 2H), 3.87 (q, J=6.9 Hz, 2H), 3.47 (m, 1H), 3.41 (s, 3H), 1.37–1.29 (m, 6H), 0.929 (t, J=6.9 Hz, 3H), MS-ESI m/z 400 [M+H]$^+$; HRMS m/z calcd for C$_{21}$H$_{27}$FN$_6$O$_2$ [M+H$^+$] 400.2149, found 400.2131.

1,2-Dimethyl-4-(4-fluorophenyl)-5-[2-[(N-propanesulfonylpiperidin-4-yl)amino]-pyrimidin-4-yl]-1,2-dihydro-pyrazol-3-one; $^1$H NMR (300 MHz, CDCl$_3$) δ 8.24 (d, J=4.8 Hz, 1H), 7.36 (m, 2H), 6.98 (t, J=9 Hz, 2H), 6.38 (d, J=5.1 Hz,1H), 5.26 (d, J=7.2 Hz, 1H), 4.16 (m, 1H), 3.51 (s, 3H) 3.35 (s, 3H), 1.27 (d, J=6.3, 6H); MS-APCI m/z 342 [M+H]$^+$; HRMS m/z calcd for C$_{18}$H$_{21}$FN$_5$O [M+H$^+$] 342.1730, found 372.1728.

Non-limiting examples of other compounds comprising the second aspect of Category IV include:

1,2-Diethyl-4-(4-fluorophenyl)-5-[2-(S)-(α-methylbenzylamino)pyrimidin-4-yl]-1,2-dihydropyrazol-3-one;

1,2-Dimethyl-4-(4-fluorophenyl)-5-[2-(thiazole-2-ylamino)pyrimidin-4-yl]-1,2-dihydro-pyrazol-3-one;

1,2-Diethyl-4-(4-fluorophenyl)-5-[2-(benzimidazol-2-ylamino)pyrimidin-4-yl]-1,2-dihydro-pyrazol-3-one.

Other compounds of the present invention, not directly encompassed within the herein above defined categories, which can be prepared by the procedures or modifications thereof disclosed herein above, include the following.

5-(2-Phenoxypyrimidin-4-yl)-4-(4-fluorophenyl)-1,2-dihydropyrazol-3-one;

2-Benzothiazol-2-yl-4-(4-fluorophenyl)-5-[2-(1-phenylethylamino)-pyrimidin-4-yl]-1,2-dihydropyrazol-3-one;

4-(4-Fluorophenyl)-1-(2-methoxyethyl)-5-[2-(2-methoxy-1-methylethylamino)pyrimidin-4-yl]-2-methyl-1,2-dihydropyrazol-3-one;

4-(4-Fluorophenyl)-1-(2-methoxyethyl)-5-[2-(1-phenylethylamino)-pyrimidin-4-yl]-2-methyl-1,2-dihydropyrazol-3-one;

4-(4-Fluorophenyl)-1-(2-methoxyethyl)-5-(2-phenoxypyrimidin-4-yl)-2-methyl-1,2-dihydropyrazol-3-one;

4-(4-Fluorophenyl)-1-methyl-5-[2-methoxypyrimidin-4-yl]-2-piperidin-4-yl-1,2-dihydropyrazol-3-one;

4-(4-Fluorophenyl)-1-(piperidin-4-yl)-5-[2-(2-methoxy-1-methylethylamino)pyrimidin-4-yl]-2-phenyl-1,2-dihydropyrazol-3-one;

4-(4-Fluorophenyl)-1-(piperidin-4-yl)-5-[2-(2-methoxy-1-methylethylamino)pyrimidin-4-yl]-2-(4-chloro)phenyl-1,2-dihydropyrazol-3-one;

4-(4-Fluorophenyl)-2-(2-methoxyethyl)-5-[2-(2-methoxy-1-methylethylamino)pyrimidin-4-yl]-1-methyl-1,2-dihydropyrazol-3-one;

4-(4-Fluorophenyl)-2-(2-methoxyethyl)-5-(2-phenoxypyrimidin-4-yl)-1-methyl-1,2-dihydropyrazol-3-one;

4-(4-Fluorophenyl)-2-(2-methoxyethyl)-5-[2-(2-hydroxy-1,2-dimethylpropylamino)-pyrimidin-4-yl]-1-methyl-1,2-dihydropyrazol-3-one;

2-(4-Chlorophenyl)-4-(4-fluorophenyl)-5-[2-(1-phenylethylamino)-pyrimidin-4-yl]-1,2-dihydropyrazol-3-one;

4-(4-Fluorophenyl)-1-methoxymethyl-5-(2-phenyoxypyrimidin-4-yl)-1,2-dihydropyrazol-3-one;

1-(Piperidin-4-yl)-2-methyl-4-(4-fluorophenyl)-5-[2-(tetrahydropyran-4-yl)pyrimidin-4-yl]-1,2-dihydro-pyrazol-3-one.

Compounds listed and described herein above have been found in many instances to exhibit activities (IC$_{50}$ in the cell based assay described herein below or ones which are referenced herein) at a level below 1 micromolar (μM).

The compounds of the present invention are capable of effectively blocking the production of inflammatory cytokine production from cells, which thereby allows for the mitigation, alleviation, control, abatement, retardation, or prevention of one or more disease states or syndromes which are related to the extracellular release of one or more cytokines. Inflammatory disease states include those which are related to the following non-limiting examples:

i) Interleukin-1 (IL-1): implicated as the molecule responsible for a large number of disease states, inter alia, rheumatoid arthritis, osteoarthritis, as well as other disease states which relate to connective tissue degradation.

ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).

iii) Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBS), septic shock, cardiopulmonary dysfunction, acute respiratory disease, and cachexia.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Related to this aspect are the various precursor of "pro-drug" forms of the analogs of the present invention. It may be desirable to formulate the compounds of the present invention as a chemical species which itself is not active against the cytokine activity described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are converted in vivo to the active pharmaceutical.

FORMULATIONS

The present invention also relates to compositions or formulations which comprise the inflammatory cytokine release-inhibiting compounds according to the present invention. In general, the compositions of the present invention comprise:

a) an effective amount of 1,2-dihydropyrazol-3-ones according to the present invention which are effective for inhibiting release of inflammatory cytokines; and b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present invention also relates to compositions or formulations which comprise a precursor or "pro-drug" form of the inflammatory cytokine release-inhibiting compounds according to the present invention. In general, these precursor-comprising compositions of the present invention comprise:

a) an effective amount of one or more derivatives of bicyclic pyrazolones according to the present invention which act to release in vivo the corresponding analog which is effective for inhibiting release of inflammatory cytokines; and b) one or more pharmaceutically acceptable excipients.

METHOD OF USE

The present invention also relates to a method for controlling the level of one or more inflammation inducing cytokines, interalia, interleukin-1 (IL-1), Tumor Necrosis Factor-α (TNF-α), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

PROCEDURES

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:

i) UV-visible substrate enzyme assay as described by L. Al Reiter, *Int. J. Peptide Protein Res.*, 43, 87–96 (1994).

ii) Fluorescent substrate enzyme assay as described by Thornberry et al., *Nature*, 356, 768–774 (1992).

iii) PBMC Cell assay as described in U.S. Pat. No. 6,204,261 B1 Batchelor et al., issued Mar. 20, 2001.

Each of the above citations is included herein by reference.

In addition, Tumor Necrosis Factor, TNF-α, inhibition can be measured by utilizing lipopolysaccharide (LPS) stimulated human monocytic cells (THP-1) as described in:

i) K. M. Mohler et al., "Protection Against a Lethal Dose of Endotoxin by an Inhibitor of Tumour Necrosis Factor Processing", *Nature*, 370, pp 218–220 (1994).

ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-α in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP.1 cells ($2\times10^7$ cells/mL, final conc.; American Type Culture Company, Rockville, Md.) are added to 96 well polypropylene round bottomed culture plates (Costar 3790; sterile) containing 125 μL test compound (2-fold concentrated) or DMSO vehicle (controls, blanks). DMSO concentration should not exceed 0.2% final. Cell mixture is allowed to preincubate for 30 minutes at 37° C., 5% $CO_2$ prior to stimulation with lipopolysaccharide (LPS, 1 μg/mL final; Sigma L-2630, from *E. coli* serotype 0111.B4; stored as 1 mg/mL stock in endotoxin screened diluted $H_2O$ vehicle at −80° C.). Blanks (unstimulated) receive $H_2O$ vehicle; final incubation volume is 250 μL. Incubation (4 hours) proceeds as described above. Assay is to be terminated by centrifuging plates 5 minutes at room temperature, 1600 rpm (4033 g); supernatants are then transferred to clean 96 well plates and stored at −80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, or all enantiomeric and diasteriomeric forms or pharmaceutically acceptable salts thereof, said compound having the formula:

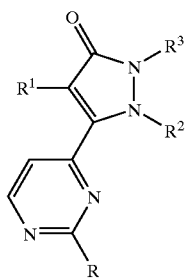

wherein R is:
a) —O[CH$_2$]$_n$R$^4$; or
b) —N R$^{5a}$R$^{5b}$;

R$^4$ is substituted or unsubstituted C$_1$–C$_{10}$ linear, branched, or cyclic alkyl; substituted or unsubstituted aryl; substituted or unsubstituted heterocyclic; or substituted or unsubstituted heteroaryl; the index n is from 0 to 5;

R$^{5a}$ and R$^{5b}$ are each independently:
a) hydrogen; or
b) —[C(R$^{6a}$R$^{6b}$)]$_m$R$^7$;

each R$^{6a}$ and R$^{6b}$ is independently:
i) hydrogen;
ii) —OR$^8$;
iii) —N(R$^8$)$_2$;
iv) —CO$_2$R$^8$;
v) —CON(R$^8$)$_2$;
vi) substituted or unsubstituted C$_1$–C$_4$ linear, branched, or cyclic alkyl;
vii) and mixtures thereof;

R$^7$ is
i) hydrogen;
ii) substituted or unsubstituted C$_1$–C$_6$ linear, branched, or cyclic alkyl;
iii) substituted or unsubstituted heterocyclic;
iv) substituted or unsubstituted aryl;
v) substituted or unsubstituted heteroaryl;
vi) —OR$^8$;
vii) —N(R$^8$)$_2$;
viii) —CO$_2$R$^8$; and
ix) —CON(R$^8$)$_2$;

R$^8$ is hydrogen, a water-soluble cation, C$_1$–C$_4$ alkyl, or substituted or unsubstituted aryl;

the index m is from 0 to 5;

R$^1$ is substituted phenyl;

each R$^2$ and R$^3$ unit is independently selected from the group consisting of:
a) hydrogen; and
b) substituted or unsubstituted C$_1$–C$_{10}$ hydrocarbyl selected from the group consisting of:
i) C$_1$–C$_{10}$ linear, branched or cyclic alkyl;
ii) C$_6$–C$_{10}$ aryl;
iii) C$_1$–C$_{10}$ heterocyclic;
iv) C$_1$–C$_{10}$ heteroaryl.

2. A compound according to claim 1 having the formula:

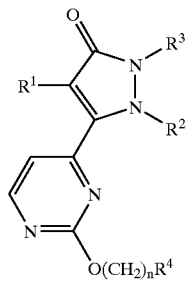

wherein R$^4$ is substituted or unsubstituted:
i) C$_1$–C$_4$ alkyl;
ii) C$_3$–C$_{10}$ carbocyclic;
iii) C$_1$–C$_{10}$ heterocyclic;
iv) C$_6$–C$_{10}$ aryl; or
v) C$_1$–C$_{10}$ heteroaryl;
the index n is from 0 to 5.

3. A compound according to claim 2 wherein R$^1$ is 4-fluorophenyl.

4. A compound according to claim 3 wherein R$^4$ is substituted or unsubstituted aryl and the index n is 0 or 1.

5. A compound according to claim 4 wherein R$^4$ is selected from the group consisting of phenyl, 2-fluorophenyl, 3-fluorophenyl, 4-fluorophenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetyl-aminophenyl, 2-methoxyphenyl, 4-methoxyphenyl, and 3-benzo[1,3]dioxol-5-yl.

6. A compound according to claim 3 wherein R$^2$ and R$^3$ are each independently substituted or unsubstituted C$_1$–C$_{10}$ hydrocarbyl selected from:
i) C$_1$–C$_{10}$ linear, branched or cyclic alkyl;
ii) C$_1$–C$_{10}$ aryl;
iii) C$_1$–C$_{10}$ heterocyclic;
iv) C$_1$–C$_{10}$ heteroaryl.

7. A compound according to claim 6 wherein R$^2$ is selected from the group consisting of methyl, ethyl, propyl, isopropyl, butyl, sec-butyl, isobutyl, tert-butyl, and cyclopropyl-methyl.

8. A compound according to claim 6 wherein R$^3$ is selected from the group consisting of substituted or unsubstituted piperidin-4-yl, N-methylpiperidin-4-yl, morpholin-4-yl, and N-methylmorpholin-4-yl.

9. A compound according to claim 6 wherein R$^4$ is selected from the group consisting of phenyl, 2-fluorophenyl, 3-fluorophenyl, 4-fluorophenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetyl-aminophenyl, 2-methoxyphenyl, 4-methoxyphenyl, and 3-benzo[1,3]dioxol-5-yl, R$^2$ is selected from the group consisting of methyl, ethyl, propyl, isopropyl, butyl, sec-butyl, isobutyl, tert-butyl, and cyclopropylmethyl, R$^3$ is selected from the group consisting of substituted or unsubstituted piperidin-4-yl, N-methylpiperidin-4-yl, morpholin-4-yl, and N-methylmorpholin-4-yl, and the index n is 0 or 1.

10. A compound according to claim 6 selected from the group consisting of:
4-(4-fluorophenyl)-2-methyl-5-(2-phenoxy-pyrimidin-4-yl)-1-piperidin-4-yl-1,2-dihydro-pyrazol-3-one
4-(4-fluorophenyl)-2-methyl-5-(2-phenoxy-pyrimidin-4-yl)-1-piperidin-4-yl-1,2-dihydro-pyrazol-3-one;

4-(4-fluorophenyl)-2-methyl-5-[2-(2-fluorophenoxy)
pyrimidin-4-yl]-1-piperidin-4-yl-1,2-dihydro-pyrazol-
3-one;

4-(4-fluorophenyl)-2-methyl-5-[2-(3-fluorophenoxy)
pyrimidin-4-yl]-1-piperidin-4-yl-1,2-dihydro-pyrazol-
3-one;

4-(4-fluorophenyl)-2-methyl-5-[2-(4-fluorophenoxy)
pyrimidin-4-yl]-1-piperidin-4-yl-1,2-dihydro-pyrazol-
3-one;

4-(4-fluorophenyl)-2-ethyl-5-(2-phenoxy-pyrimidin-4-
yl)-1-piperidin-4-yl-1,2-dihydro-pyrazol-3-one;

4-(4-fluorophenyl)-2-ethyl-5-[2-(2-fluorophenoxy)
pyrimidin-4-yl]-1-piperidin-4-yl-1,2-dihydro-pyrazol-
3one;

4-(4-fluorophenyl)-2-ethyl-5-[2-(3-fluorophenoxy)
pyrimidin-4-yl]-1-piperidin-4-yl-1,2-dihydro-pyrazol-
3-one;

4-(4-fluorophenyl)-2-ethyl-5-[2-(4-fluorophenoxy)
pyrimidin-4-yl]-1-piperidin-4-yl-1,2-dihydro-pyrazol-
3-one;

4-(4-fluorophenyl)-2-methyl-5-(2-phenoxy-pyrimidin-4-
yl)-1-morpholin-4-yl-1,2-dihydro-pyrazol-3-one;

4-(4-fluorophenyl)-2-methyl-5-[2-(2-fluorophenoxy)
pyrimidin-4-yl]-1-morpholin-4-yl-1,2-dihydro-
pyrazol-3-one;

4-(4-fluorophenyl)-2-methyl-5-[2-(3-fluorophenoxy)
pyrimidin-4-yl]-1-morpholin-4-yl-1,2-dihydro-
pyrazol-3-one;

4-(4-fluorophenyl)-2-methyl-5-[2-(4-fluorophenoxy)
pyrimidin-4-yl]-1-morpholin-4-yl-1,2-dihydro-
pyrazol-3-one;

4-(4-fluorophenyl)-2-ethyl-5-(2-phenoxy-pyrimidin-4-
yl)-1-morpholin-4-yl-1,2-dihydro-pyrazol-3-one;

4-(4-fluorophenyl)-2-ethyl-5-[2-(2-fluorophenoxy)
pyrimidin-4-yl]-1-morpholin-4-yl-1,2-dihydro-
pyrazol-3-one;

4-(4-fluorophenyl)-2-ethyl-5-[2-(3-fluorophenoxy)
pyrimidin-4-yl]-1-morpholin-4-yl-1,2-dihydro-
pyrazol-3-one;

4-(4-fluorophenyl)-2-ethyl-5-[2-(4-fluorophenoxy)
pyrimidin-4-yl]-1-morpholin-4-yl-1,2-dihydro-
pyrazol-3-one;

4-(4-fluorophenyl)-2-methyl-5-(2-phenoxy-pyrimidin-4-
yl)-1-N-methylpiperidin-4-yl-1,2-dihydro-pyrazol-3-
one;

4-(4-fluorophenyl)-2-methyl-5-[2-(2-fluorophenoxy)
pyrimidin-4-yl]-1-N-methylpiperidin-4-yl-1,2-
dihydro-pyrazol-3-one;

4-(4-fluorophenyl)-2-methyl-5-[2-(3-fluorophenoxy)
pyrimidin-4-yl]-1-N-methylpiperidin-4-yl-1,2-
dihydro-pyrazol-3-one;

4-(4-fluorophenyl)-2-methyl-5-[2-(4-fluorophenoxy)
pyrimidin-4-yl]-1-N-methylpiperidin-4-yl-1,2-
dihydro-pyrazol-3-one;

4-(4-fluorophenyl)-2-ethyl-5-(2-phenoxy-pyrimidin-4-
yl)-1-N-methylpiperidin-4-yl-1,2-dihydro-pyrazol-3-
one;

4-(4-fluorophenyl)-2-ethyl-5-[2-(2-fluorophenoxy)
pyrimidin-4-yl]-1-N-methylpiperidin-4-yl-1,2-
dihydro-pyrazol-3-one;

4-(4-fluorophenyl)-2-ethyl-5-[2-(3-fluorophenoxy)
pyrimidin-4-yl]-1-N-methylpiperidin-4-yl-1,2-
dihydro-pyrazol-3-one; and 4-(4-fluorophenyl)-2-ethyl-5-[2-(4-fluorophenoxy)
pyrimidin-4-yl]-1-N-methylpiperidin-4-yl-1,2-
dihydro-pyrazol-3-one.

11. A compound according to claim 6 wherein $R^2$ is selected from the group consisting of substituted or unsubstituted piperidin-4-yl, N-methylpiperidin-4-yl, morpholin-4-yl, and N-methylmorpholin-4-yl.

12. A compound according to claim 6 wherein $R^3$ is selected from the group consisting of methyl, ethyl, propyl, isopropyl, butyl, sec-butyl, isobutyl, tert-butyl, and cyclopropylmethyl.

13. A compound according to claim 6 wherein $R^4$ is selected from the group consisting of phenyl, 2-fluorophenyl, 3-fluorophenyl, 4-fluorophenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetyl-aminophenyl, 2-methoxyphenyl, 4-methoxyphenyl, and 3-benzo[1,3]dioxol-5-yl, $R^2$ is selected from the group consisting of substituted or unsubstituted piperidin-4-yl, N-methylpiperidin-4-yl, morpholin-4-yl, and N-methylmorpholin-4-yl, $R^3$ is selected from the group consisting of methyl, ethyl, propyl, isopropyl, butyl, sec-butyl, isobutyl, tert-butyl, and cyclopropylmethyl, and the index n is 0 or 1.

14. A compound according to claim 6 selected from the group consisting of:

4-(4-fluorophenyl)-1-methyl-5-(2-phenoxy-pyrimidin-4-
yl)-2-piperidin-4-yl-1,2-dihydro-pyrazol-3-one;

4-(4-fluorophenyl)-1-methyl-5-[2-(2-fluorophenoxy)
pyrimidin-4-yl]-2-piperidin-4-yl-1,2-dihydro-pyrazol-
3-one;

4-(4-fluorophenyl)-1-methyl-5-[2-(3-fluorophenoxy)
pyrimidin-4-yl]-2-piperidin-4-yl-1,2-dihydro-pyrazol-
3-one;

4-(4-fluorophenyl)-1-methyl-5-[2-(4-fluorophenoxy)
pyrimidin-4-yl]-2-piperidin-4-yl-1,2-dihydro-pyrazol-
3-one;

4-(4-fluorophenyl)-1-ethyl-5-(2-phenoxy-pyrimidin-4-
yl)-2-piperidin-4-yl-1,2-dihydro-pyrazol-3-one;

4-(4-fluorophenyl)-1-ethyl-5-[2-(2-fluorophenoxy)
pyrimidin-4-yl]-2-piperidin-4-yl-1,2-dihydro-pyrazol-
3-one;

4-(4-fluorophenyl)-1-ethyl-5-[2-(3-fluorophenoxy)
pyrimidin-4-yl]-2-piperidin-4-yl-1,2-dihydro-pyrazol-
3-one;

4-(4-fluorophenyl)-1-ethyl-5-[2-(4-fluorophenoxy)
pyrimidin-4-yl]-2-piperidin-4-yl-1,2-dihydro-pyrazol-
3-one;

4-(4-fluorophenyl)-1-methyl-5-(2-phenoxy-pyrimidin-4-
yl)-2-morpholin-4-yl-1,2-dihydro-pyrazol-3-one;

4-(4-fluorophenyl)-1-methyl-5-[2-(2-fluorophenoxy)
pyrimidin-4-yl]-2-morpholin-4-yl-1,2-dihydro-
pyrazol-3-one;

4-(4-fluorophenyl)-1-methyl-5-[2-(3-fluorophenoxy)
pyrimidin-4-yl]-2-morpholin-4-yl-1,2-dihydro-
pyrazol-3-one;

4-(4-fluorophenyl)-1-methyl-5-[2-(4-fluorophenoxy)
pyrimidin-4-yl]-2-morpholin-4-yl-1,2-dihydro-
pyrazol-3-one;

4-(4-fluorophenyl)-1-ethyl-5-(2-phenoxy-pyrimidin-4-
yl)-2-morpholin-4-yl-1,2-dihydro-pyrazol-3-one;

4-(4-fluorophenyl)-1-ethyl-5-[2-(2-fluorophenoxy)
pyrimidin-4-yl]-2-morpholin-4-yl-1,2-dihydro-
pyrazol-3-one;

4-(4-fluorophenyl)-1-ethyl-5-[2-(3-fluorophenoxy) pyrimidin-4-yl]-2-morpholin-4-yl-1,2-dihydro-pyrazol-3-one;

4-(4-fluorophenyl)-1-ethyl-5-[2-(4-fluorophenoxy) pyrimidin-4-yl]-2-morpholin-4-yl-1,2-dihydro-pyrazol-3-one;

4-(4-fluorophenyl)-1-methyl-5-(2-phenoxy-pyrimidin-4-yl)-2-N-methylpiperidin-4-yl-1,2-dihydro-pyrazol-3-one;

4-(4-fluorophenyl)-1-methyl-5-[2-(2-fluorophenoxy) pyrimidin-4-yl]-2-N-methylpiperidin-4-yl-1,2-dihydro-pyrazol-3-one;

4-(4-fluorophenyl)-1-methyl-5-[2-(3-fluorophenoxy) pyrimidin-4-yl]-2-N-methylpiperidin-4-yl -1,2-dihydro-pyrazol-3-one;

4-(4-fluorophenyl)-1-methyl-5-[2-(4-fluorophenoxy) pyrimidin-4-yl]-2-N-methylpiperidin-4-yl-1,2-dihydro-pyrazol-3-one;

4-(4-fluorophenyl)-1-ethyl-5-(2-phenoxy-pyrimidin-4-yl)-2-N-methylpiperidin-4-yl-1,2-dihydro-pyrazol-3-one;

4-(4-fluorophenyl)-1-ethyl-5-[2-(2-fluorophenoxy) pyrimidin-4-yl]-2-N-methylpiperidin-4-yl -1,2-dihydro-pyrazol-3-one;

4-(4-fluorophenyl)-1-ethyl-5-[2-(3-fluorophenoxy) pyrimidin-4-yl]-2-N-methylpiperidin-4-yl-1,2-dihydro-pyrazol-3-one; and 4-(4-fluorophenyl)-1-ethyl-5-[2-(4-fluorophenoxy) pyrimidin-4-yl]-2-N-methylpiperidin-4-yl-1,2-dihydro-pyrazol-3-one.

15. A compound according to claim 6 wherein $R^2$ and $R^3$ are both methyl or both ethyl, $R^4$ is selected from the group consisting of phenyl, 2-fluorophenyl, 3-fluorophenyl, 4-fluorophenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetyl-aminophenyl, 2-methoxyphenyl, 4-methoxyphenyl, and 3-benzo[1,3] dioxol-5-yl, and the index n is 0 or 1.

16. A compound according to claim 15 selected from the group consisting of:

1,2-dimethyl-4-(4-fluorophenyl)-5-(2-phenoxypyrimidin-4-yl)-1,2-dihydropyrazol-3-one;

1,2-diethyl-4-(4-fluorophenyl)-5-(2-phenoxypyrimidin-4-yl)-1,2-dihydropyrazol-3-one;

1,2-dimethyl-4-(4-fluorophenyl)-5-[2-(2-fluorophenoxy) pyrimidin-4-yl]-1,2-dihydropyrazol-3-one;

1,2-diethyl-4-(4-fluorophenyl)-5-[2-(2-fluorophenoxy) pyrimidin-y]-1,2-dihydropyrazol-3-one;

1,2-dimethyl-4-(4-fluorophenyl)-5-[2-(3-fluorophenoxy) pyrimidin-4-yl]-1,2-dihydropyrazol-3-one;

1,2-diethyl-4-(4-fluorophenyl)-5-[2-(3-fluorophenoxy) pyrimidin-4-yl]-1,2-dihydropyrazol-3-one;

1,2-dimethyl-4-(4-fluorophenyl)-5-[2-(4-fluorophenoxy) pyrimidin-4-yl]-1,2-dihydropyrazol-3-one; and 1,2-diethyl-4-(4-fluorophenyl)-5-[2-(4-fluorophenoxy) pyrimidin-4-yl]-1,2-dihydropyrazol-3-one.

17. A compound according to claim 1 having the formula:

wherein $R^2$ and $R^3$ are each independently substituted or unsubstituted $C_1$–$C_{10}$ hydrocarbyl selected from:
 i) $C_1$–$C_{10}$ linear, branched or cyclic alkyl;
 ii) $C_6$–$C_{10}$ aryl;
 iii) $C_1$–$C_{10}$ heterocyclic; and
 iv) $C_1$–$C_{10}$ heteroaryl;

$R^{6b}$ is hydrogen, $C_1$–$C_4$ alkyl, or —$CO_2R^8$; $R^8$ is hydrogen, methyl, or a salt forming cation;

$R^7$ is selected from the group consisting of:
 i) hydrogen;
 ii) substituted or unsubstituted $C_1$–$C_6$ linear, branched, or cyclic alkyl;
 iii) substituted or unsubstituted $C_6$–$C_{10}$ aryl;
 iv) substituted or unsubstituted $C_1$–$C_{10}$ heterocyclic; and
 v) substituted or unsubstituted $C_1$–$C_{10}$ heteroaryl.

18. A compound according to claim 15 wherein $R^{6b}$ is hydrogen.

19. A compound according to claim 18 wherein $R^7$ is substituted or unsubstituted $C_6$–$C_{10}$ aryl.

20. A compound according to claim 19 wherein $R^2$ is selected from the group consisting of methyl, ethyl, propyl, isopropyl, butyl, sec-butyl, isobutyl, tert-butyl, and cyclopropyl-methyl.

21. A compound according to claim 19 wherein $R^3$ is selected from the group consisting of substituted or unsubstituted piperidin-4-yl, N-methylpiperidin-4-yl, morpholin-4-yl, and N-methylmorpholin-4-yl.

22. A compound according to claim 18 wherein $R^2$ is selected from the group consisting of methyl, ethyl, propyl, isopropyl, butyl, sec-butyl, isobutyl, tert-butyl, and cyclopropyl-methyl, $R^3$ is selected from the group consisting of substituted or unsubstituted piperidin-4-yl, N-methylpiperidin-4-yl, morpholin-4-yl, and N-methylmorpholin-4-yl, and $R^7$ is substituted or unsubstituted $C_6$–$C_{10}$ aryl.

23. A compound according to claim 18 wherein $R^2$ is selected from the group consisting of substituted or unsubstituted piperidin-4-yl, N-methylpiperidin-4-yl, morpholin-4-yl, and N-methylmorpholin-4-yl.

24. A compound according to claim 18 wherein $R^3$ is selected from the group consisting of methyl, ethyl, propyl, isopropyl, butyl, sec-butyl, isobutyl, tert-butyl, and cyclopropyl-methyl.

25. A compound according to claim 18 wherein $R^2$ is selected from the group consisting of substituted or unsubstituted piperidin-4-yl, N-methylpiperidin-4-yl, morpholin-4-yl, and N-methylmorpholin-4-yl, $R^3$ is selected from the group consisting of methyl, ethyl, propyl, isopropyl, butyl, sec-butyl, isobutyl, tert-butyl, and cyclopropyl-methyl, and $R^7$ is substituted or unsubstituted $C_6$–$C_{10}$ aryl.

26. A compound according to claim 19 wherein $R^2$ and $R^3$ are both methyl or both ethyl.

27. A compound according to claim 17 selected from the group consisting of:

4-(4-fluorophenyl)-2-methyl-5-{2-[(phenyl)methylamino]-pyrimidin-4-yl}-1-piperidin-4-yl-1,2-dihydropyrazol-3-one;

4-(4-fluorophenyl)-2-methyl-5-{2-[(2-fluorophenyl)methylamino]-pyrimidin-4-yl}-1-piperidin-4-yl-1,2-dihydropyrazol-3-one;

4-(4-fluorophenyl)-2-methyl-5-{2-[(3-fluorophenyl)methylamino]-pyrimidin-4-yl}-1-piperidin-4-yl-1,2-dihydropyrazol-3-one;

4-(4-fluorophenyl)-2-methyl-5-{2-[(4-fluorophenyl)methylamino]-pyrimidin-4-yl}-1-piperidin-4-yl-1,2-dihydropyrazol-3-one;

4-(4-fluorophenyl)-2-methyl-5-{2-[(2-aminophenyl)methylamino]-pyrimidin-4-yl}-1-piperidin-4-yl-1,2-dihydropyrazol-3-one;

4-(4-fluorophenyl)-2-methyl-5-{2-[(3-aminophenyl)methylamino]-pyrimidin-4-yl}-1-piperidin-4-yl-1,2-dihydropyrazol-3-one;

4-(4-fluorophenyl)-2-methyl-5-{2-[(4-aminophenyl)methylamino]-pyrimidin-4-yl}-1-piperidin-4-yl-1,2-dihydropyrazol-3-one;

4-(4-fluorophenyl)-2-methyl-5-{2-[(phenyl)methylamino]-pyrimidin-4-yl}-1-morpholin-4-yl-1,2-dihydropyrazol-3-one;

4-(4-fluorophenyl)-2-methyl-5-{2-[(2-fluorophenyl)methylamino]-pyrimidin-4-yl}-1-morpholin-4-yl-1,2-dihydropyrazol-3-one;

4-(4-fluorophenyl)-2-methyl-5-{2-[(3-fluorophenyl)methylamino]-pyrimidin-4-yl}-1-morpholin-4-yl-1,2-dihydropyrazol-3-one;

4-(4-fluorophenyl)-2-methyl-5-{2-[(4-fluorophenyl)methylamino]-pyrimidin-4-yl}-1-morpholin-4-yl-1,2-dihydropyrazol-3-one;

4-(4-fluorophenyl)-2-methyl-5-{2-[(2-aminophenyl)methylamino]-pyrimidin-4-yl}-1-morpholin-4-yl-1,2-dihydropyrazol-3-one;

4-(4-fluorophenyl)-2-methyl-5-{2-[(3-aminophenyl)methylamino]-pyrimidin-4-yl}-1-morpholin-4-yl-1,2-dihydropyrazol-3-one;

4-(4-fluorophenyl)-2-methyl-5-{2-[(4-aminophenyl)methylamino]-pyrimidin-4-yl}-1-morpholin-4-yl-1,2-dihydropyrazol-3-one;

4-(4-fluorophenyl)-2-methyl-5-{2-[(phenyl)methylamino]-pyrimidin-4-yl}-1-(N-acetyl)-piperidin-4-yl-1,2-dihydropyrazol-3-one;

4-(4-fluorophenyl)-2-methyl-5-{2-[(2-fluorophenyl)methylamino]-pyrimidin-4-yl}-1-(N-acetyl)-piperidin-4-yl-1,2-dihydropyrazol-3-one;

4-(4-fluorophenyl)-2-methyl-5-{2-[(3-fluorophenyl)methylamino]-pyrimidin-4-yl}-1-(N-acetyl)-piperidin-4-yl-1,2-dihydropyrazol-3-one;

4-(4-fluorophenyl)-2-methyl-5-{2-[(4-fluorophenyl)methylamino]-pyrimidin-4-yl}-1-(N-acetyl)-piperidin-4-yl-1,2-dihydropyrazol-3-one;

4-(4-fluorophenyl)-2-methyl-5-{2-[(2-aminophenyl)methylamino]-pyrimidin-4-yl}-1-(N-acetyl)-piperidin-4-yl-1,2-dihydropyrazol-3-one;

4-(4-fluorophenyl)-2-methyl-5-{2-[(3-aminophenyl)methylamino]-pyrimidin-4-yl}-1-(N-acetyl)-piperidin-4-yl-1,2-dihydropyrazol-3-one; and 4-(4-fluorophenyl)-2-methyl-5-{2-[(4-aminophenyl)methylamino]-pyrimidin-4-yl}-1-(N-acetyl)-piperidin-4-yl-1,2-dihydropyrazol-3-one.

28. A compound according to claim 1 having the formula:

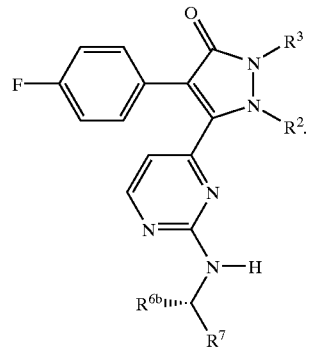

wherein $R^2$ and $R^3$ are each independently substituted or unsubstituted $C_1$–$C_{10}$ hydrocarbyl selected from:
  i) $C_1$–$C_{10}$ linear, branched or cyclic alkyl;
  ii) $C_1$–$C_{10}$ aryl;
  iii) $C_1$–$C_{10}$ heterocyclic; and
  iv) $C_1$–$C_{10}$ heteroaryl;
$R^{6b}$ is $C_1$–$C_4$ alkyl, or —$CO_2R^8$; $R^8$ is hydrogen, methyl, or a salt forming cation; $R^7$ is selected from the group consisting of:
  i) hydrogen;
  ii) substituted or unsubstituted aryl;
  iii) substituted or unsubstituted heteroaryl;
  iv) substituted or unsubstituted heterocyclic; and
  v) substituted or unsubstituted $C_1$–$C_6$ linear, branched, or cyclic alkyl.

29. A compound according to claim 28 wherein $R^{6b}$ is hydrogen.

30. A compound according to claim 29 wherein $R^7$ is substituted or unsubstituted $C_6$–$C_{10}$ aryl.

31. A compound according to claim 29 wherein $R^2$ is selected from the group consisting of methyl, ethyl, propyl, isopropyl, butyl, sec-butyl, isobutyl, tert-butyl, and cyclopropyl-methyl.

32. A compound according to claim 29 wherein $R^3$ is selected from the group consisting of substituted or unsubstituted piperidin-4-yl, N-methylpiperidin-4-yl, morpholin-4-yl, and N-methylmorpholin-4-yl.

33. A compound according to claim 29 wherein $R^2$ is selected from the group consisting of methyl, ethyl, propyl, isopropyl, butyl, sec-butyl, isobutyl, tert-butyl, and cyclopropyl-methyl, $R^3$ is selected from the group consisting of substituted or unsubstituted piperidin-4-yl, N-methylpiperidin-4-yl, morpholin-4-yl, and N-methylmorpholin-4-yl, and $R^7$ is substituted or unsubstituted $C_6$–$C_{10}$ aryl.

34. A compound according to claim 33 wherein $R^7$ is selected from the group consisting of phenyl, 4-fluorophenyl, 2-aminophenyl, 2-methylphenyl, 4-methylphenyl, 4-methoxy-phenyl, 4-(methanesulfonyl)phenyl, 4-(ethanesulfonyl)phenyl, 4-(propanesulfonyl)phenyl, 3-benzo[1,3]dioxol-5-yl, pyridin-2-yl, pyridin-3-yl, and pyridin-4-yl.

35. A compound according to claim 33 wherein $R^7$ is methyl, ethyl, cyclopropyl, cyclohexyl, hydroxymethyl, methoxymethyl, 1-methoxyethyl, 1-methoxy-1-methyl-ethyl, 1-hydroxy-1-methyl-ethyl, and 1-hydroxyethyl.

36. A compound according to claim 29 wherein $R^2$ is selected from the group consisting of substituted or unsubstituted piperidin-4-yl, N-methylpiperidin-4-yl, morpholin-4-yl, and N-methylmorpholin-4-yl.

37. A compound according to claim 29 wherein $R^3$ is selected from the group consisting of methyl, ethyl, propyl, isopropyl, butyl, sec-butyl, isobutyl, tert-butyl, and cyclopropyl-methyl.

38. A compound according to claim 29 wherein $R^2$ is selected from the group consisting of substituted or unsubstituted piperidin-4-yl, N-methylpiperidin-4-yl, morpholin-4-yl, and N-methylmorpholin-4-yl, $R^3$ is selected from the group consisting of methyl, ethyl, propyl, isopropyl, butyl, sec-butyl, isobutyl, tert-butyl, and cyclopropyl-methyl, and $R^7$ is substituted or unsubstituted $C_6$–$C_{10}$ aryl.

39. A compound according to claim 38 wherein $R^7$ is selected from the group consisting of phenyl, 4-fluorophenyl, 2-aminophenyl, 2-methylphenyl, 4-methylphenyl, 4-methoxy-phenyl, 4-(methanesulfonyl)phenyl, 4-(ethanesulfonyl)phenyl, 4-(propanesulfonyl)phenyl, 3-benzo[1,3]dioxol-5-yl, pyridin-2-yl, pyridin-3-yl, and pyridin-4-yl.

40. A compound according to claim 38 wherein $R^7$ is methyl, ethyl, cyclopropyl, cyclohexyl, hydroxymethyl, methoxymethyl, 1-methoxyethyl, 1-methoxy-1-methyl-ethyl, 1-hydroxy-1-methyl-ethyl, and 1-hydroxyethyl.

41. A compound according to claim 30 wherein $R^2$ and $R^3$ are both methyl or both ethyl.

42. A compound according to claim 41 wherein $R^7$ is selected from the group consisting of phenyl, 4-fluorophenyl, 2-aminophenyl, 2-methylphenyl, 4-methylphenyl, 4-methoxy-phenyl, 4-(methanesulfonyl)phenyl, 4-(ethanesulfonyl)phenyl, 4-(propanesulfonyl)phenyl, 3-benzo[1,3]dioxol-5-yl, pyridin-2-yl, pyridin-3-yl, and pyridin-4-yl.

43. A compound according to claim 41 wherein $R^7$ is methyl, ethyl, cyclopropyl, cyclohexyl, hydroxymethyl, methoxymethyl, 1-methoxyethyl, 1-methoxy-1-methyl-ethyl, 1-hydroxy-1-methyl-ethyl, and 1-hydroxyethyl.

44. A compound according to claim 28 selected from the group consisting of:
- 4-(4-fluorophenyl)-5-[2-(S)-(α-methylbenzylamino)pyrimidin-4-yl]-1-methyl-2-piperidin-4-yl-1,2-dihydropyrazol-3-one;
- 4-(4-fluorophenyl)-5-[2-(S)-(α-methylbenzylamino)pyrimidin-4-yl]-2-methyl-1-piperidin-4-yl-1,2-dihydropyrazol-3-one;
- (4-{4-(4-fluorophenyl)-2-methyl-5-oxo-3-[2-(S)-(α-methylbenzylamino)pyrimidin-4-yl]-2,5-dihydropyrazol-1-yl}piperidin-1-yl) acetic acid;
- 2-(4-{4-(4-Fluorophenyl)-2-methyl-5-oxo-3-[2-(S)-(α-methylbenzylamino)pyrimidin-4-yl]-2,5-dihydropyrazol-1-yl}piperidin-1-yl)-2-methyl propionic acid;
- (4-{4-(4-Fluorophenyl)-2-methyl-5-oxo-3-[2-(S)-(α-methylbenzylamino)pyrimidin-4-yl]-2,5-dihydropyrazol-1-yl}piperidin-1-yl) acetic acid ethyl ester;
- 2-(4-{4-(4-Fluorophenyl)-2-methyl-5-oxo-3-[2-(S)-(α-methylbenzylamino)pyrimidin-4-yl]-2,5-dihydropyrazol-1-yl}piperidin-1-yl)-2-methyl propionic acid ethyl ester;
- 4-(4-fluorophenyl)-5-[2-(S)-(α-methylbenzylamino)pyrimidin-4-yl]-1,2-dimethyl-1,2-dihydropyrazol-3-one;
- 4-(4-fluorophenyl)-5-[2-(2-hydroxy-1-(S)-methyl-2-methylpropylamino)-pyrimidin-4-yl]-1,2-dimethyl-1,2-dihydropyrazol-3-one;
- 4-(4-fluorophenyl)-5-[2-(2-methoxy-1-(S)-methylethylamino)-pyrimidin-4-yl]-1,2-dimethyl-1,2-dihydropyrazol-3-one;
- 4-(4-fluorophenyl)-5-[2-(S)-(α-methylbenzylamino)pyrimidin-4-yl]-1-methyl-2-(2-methoxyethyl)-1,2-dihydropyrazol-3-one;
- 4-(4-fluorophenyl)-5-[2-(S)-(α-methylbenzylamino)pyrimidin-4-yl]-2-methyl-1-(2-methoxyethyl)-1,2-dihydropyrazol-3-one;
- 4-(4-fluorophenyl)-5-[2-(2-hydroxy-1-(S)-methyl-2-methylpropylamino)-pyrimidin-4-yl]-1-methyl-2-(2-methoxyethyl)-1,2-dihydropyrazol-3-one;
- 4-(4-fluorophenyl)-5-[2-(2-hydroxy-1-(S)-methyl-2-methylpropylamino)-pyrimidin-4-yl]-2-methyl-1-(2-methoxyethyl)-1,2-dihydropyrazol-3-one;
- 4-(4-fluorophenyl)-5-[2-(2-methoxy-1-(S)-methylethylamino)-pyrimidin-4-yl]-2-methyl-1-piperidin-4-yl-1,2-dihydropyrazol-3-one; and
- 4-(4-fluorophenyl)-5-[2-(2-methoxy-1-(S)-methylethylamino)-pyrimidin-4-yl]-1-methyl-2-piperidin-4-yl -1,2-dihydropyrazol-3-one.

45. A compound, or all enantiomeric and diasteriomeric forms or pharmaceutically acceptable salts thereof, said compound having the formula:

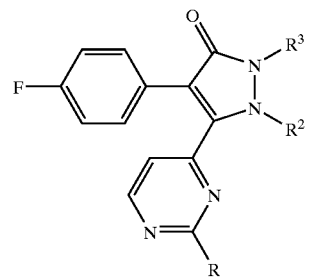

wherein R is —NH[C($R^{6a}R^{6b}$)]$R^7$ each $R^{6a}$ and $R^{6b}$ is independently methyl, ethyl, and mixtures thereof;

$R^7$ hydrogen; substituted or unsubstituted $C_1$–$C_6$ linear, branched, or cyclic alkyl;

substituted or unsubstituted aryl; and substituted or unsubstituted heteroaryl;

each $R^2$ and $R^3$ unit is independently substituted or unsubstituted $C_1$–$C_{10}$ linear, branched or cyclic alkyl; substituted or unsubstituted $C_1$–$C_{10}$ heterocyclic; and mixtures thereof.

46. A compound according to claim 45 wherein R has the formula:

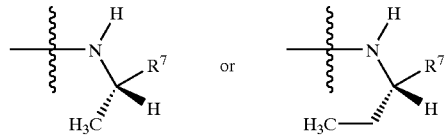

wherein $R^7$ is $C_1$–$C_3$ substituted or unsubstituted alkyl, or substituted or unsubstituted phenyl.

47. A compound according to claim 46 wherein R is selected from the group consisting of S)-(α)-methylbenzylamino, (S)-1-methyl-1-(4-fluorophenyl) methylamino, (S)-1-methyl-1-(2-aminophenyl) methylamino, (S)-1-methyl-1-(2-methylphenyl) methylamino, (S)-1-methyl-1-(4-methylphenyl) methylamino, (S)-1-methyl-1-(4-methoxyphenyl)- methylamino, (S)-(α)-ethylbenzylamino, (S)-1-(4-fluorophenyl)ethylamino, (S)-1-(2-aminophenyl)-ethylamino, (S)-1-ethyl-1-(2-methylphenyl)amino, (S)-1-(4-methylphenyl)-ethylamino, (S)-1-(4-methoxyphenyl) ethylamino, (S)-1-(4-fluorophenyl)-2-hydroxyethylamino.

48. A compound according to claim 47 wherein $R^2$ is selected from the group consisting of substituted or unsubstituted piperidin-4-yl, N-methylpiperidin-4-yl, morpholin-4-yl, and N-methylmorpholin-4-yl, and $R^3$ is selected from the group consisting of methyl, ethyl, propyl, isopropyl, butyl, sec-butyl, isobutyl, tert-butyl, and cyclopropylmethyl.

49. A compound according to claim 47 wherein $R^2$ is selected from the group consisting of methyl, ethyl, propyl, isopropyl, butyl, sec-butyl, isobutyl, tert-butyl, and cyclopropylmethyl; and $R^3$ is selected from the group consisting of substituted or unsubstituted piperidin-4-yl, N-methylpiperidin-4-yl, morpholin-4-yl, and N-methylmorpholin-4-yl.

50. A compound according to claim 46 wherein R is selected from the group consisting of (S)-1-methylpropylamino, (S)-1-methyl-1-methoxyethylamino, (S)-1-methyl-2-(S)-methoxypropylamino, (S)-1,2-methyl-2-methoxypropylamino, S)-1-ethylpropylamino, (S)-1-ethyl-1-methoxyethylamino, (S)-1-ethyl-2-(S)-methoxypropylamino, and (S)-1-ethyl-2-methyl-2-methoxypropylamino.

51. A compound according to claim 50 wherein $R^2$ is selected from the group consisting of substituted or unsubstituted piperidin-4-yl, N-methylpiperidin-4-yl, morpholin-4-yl, and N-methylmorpholin-4-yl, and $R^3$ is selected from the group consisting of methyl, ethyl, propyl, isopropyl, butyl, sec-butyl, iso-butyl, tert-butyl, and cyclopropylmethyl.

52. A compound according to claim 50 wherein $R^2$ is selected from the group consisting of methyl, ethyl, propyl, isopropyl, butyl, sec-butyl, isobutyl, tert-butyl, and cyclopropylmethyl; and $R^3$ is selected from the group consisting of substituted or unsubstituted piperidin-4-yl, N-methylpiperidin-4-yl, morpholin-4-yl, and N-methylmorpholin-4-yl.

53. A composition comprising:
A) an effective amount of on e or more 1,2-dihydropyrazol-3-ones, or enantiomeric and diastereomeric forms or pharmaceutically acceptable salts thereof, said compound having the formula:

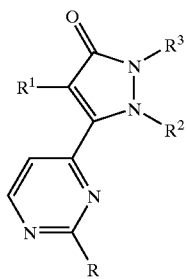

wherein R is:
a) —O[CH$_2$]$_n$R$^4$; or
b) —NR$^{5a}$R$^{5b}$;
   R$^4$ is substituted or unsubstituted C$_1$–C$_{10}$ linear, branched, or cyclic alkyl;
   substituted or unsubstituted aryl; substituted or unsubstituted heterocyclic; or
substituted or unsubstituted heteroaryl; the index n is from 0 to 5;
R$^{5a}$ and R$^{5b}$ are each independently:
a) hydrogen; or
b) —[C(R$^{6a}$R$^{6b}$)]$_m$R$^7$;
   each R$^{6a}$ and R$^{6b}$ is independently:
      i) hydrogen;
      ii) —OR$^8$;
      iii) —N(R$^8$)$_2$;
      iv) —CO$_2$R$^8$;
      vi) —CON(R$^8$)$_2$;
      vi) substituted or unsubstituted C$_1$–C$_4$ linear, branched, or cyclic alkyl;
      vii) and mixtures thereof;
   R$^7$ is
      i) hydrogen;
      ii) substituted or unsubstituted C$_1$–C$_6$ linear, branched, or cyclic alkyl;
      iii) substituted or unsubstituted heterocyclic;
      iv) substituted or unsubstituted aryl;
      v) substituted or unsubstituted heteroaryl;
      vi) —OR$^8$;
      vii) —N(R$^8$)$_2$;
      viii) —CO$_2$R$^8$; and
      ix) —CON(R$^8$)$_2$;
   R$^8$ is hydrogen, a water-soluble cation, C$_1$–C$_4$ alkyl, or substituted or unsubstituted aryl;
   the index m is from 0 to 5;
R$^1$ is substituted phenyl;
each R$^2$ and R$^3$ unit is independently selected from the group consisting of:
a) hydrogen; and
b) substituted or unsubstituted C$_1$–C$_{10}$ hydrocarbyl selected from the group consisting of:
   i) C$_1$–C$_{10}$ linear, branched or cyclic alkyl;
   ii) C$_6$–C$_{10}$ aryl;
   iii) C$_1$–C$_{10}$ heterocyclic;
   iv) C$_1$–C$_{10}$ heteroaryl; and
B) one or more pharmaceutically acceptable excipients.

54. A method for inhibiting the extracellular release of inflammatory cytokines, said method comprising the step of administering to a human or higher mammal an effective amount of a pharmaceutical composition comprising:
A) an effective amount of one or more 1,2-dihydropyrazol-3-ones, or enantiomeric and diastereomeric forms or pharmaceutically acceptable salts thereof, said compound having the formula:

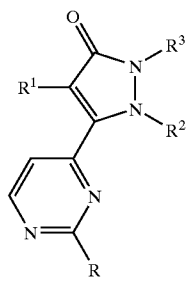

wherein R is:
a) —O[CH$_2$]$_n$R$^4$; or
b) —NR$^{5a}$R$^{5b}$;
   R$^4$ is substituted or unsubstituted C$_1$–C$_{10}$ linear, branched, or cyclic alkyl;

substituted or unsubstituted aryl; substituted or unsubstituted heterocyclic; or
substituted or unsubstituted heteroaryl; the index n is from 0 to 5;
$R^{5a}$ and $R^{5b}$ are each independently:
a) hydrogen; or
b) —[C($R^{6a}R^{6b}$)]$_m R^7$;
   each $R^{6a}$ and $R^{6b}$ is independently:
   i) hydrogen;
   ii) —$OR^8$;
   iii) —$N(R^8)_2$;
   iv) —$CO_2 R^8$;
   v) —$CON(R^8)_2$;
   vi) substituted or unsubstituted $C_1$–$C_4$ linear, branched, or cyclic alkyl;
   vii) and mixtures thereof;
$R^7$ is
   i) hydrogen;
   ii) substituted or unsubstituted $C_1$–$C_6$ linear, branched, or cyclic alkyl;
   iii) substituted or unsubstituted heterocyclic;
   iv) substituted or unsubstituted aryl;
   v) substituted or unsubstituted heteroaryl;
   vi) —$OR^8$;
   vii) —$N(R^3)_2$;
   viii) —$CO_2 R^8$; and
   ix) —$CON(R^8)_2$;
$R^8$ is hydrogen, a water-soluble cation, $C_1$–$C_4$ alkyl, or substituted or unsubstituted aryl;
the index m is from 0 to 5;
$R^1$ is substituted phenyl;
each $R^2$ and $R^3$ unit is independently selected from the group consisting of:
   a) hydrogen; and
   b) substituted or unsubstituted $C_1$–$C_{10}$ hydrocarbyl selected from the group consisting of:
      i) $C_1$–$C_{10}$ linear, branched or cyclic alkyl;
      ii) $C_6$–$C_{10}$ aryl;
      iii) $C_1$–$C_{10}$ heterocyclic;
      iv) $C_1$–$C_{10}$ heteroaryl; and
B) one or more pharmaceutically acceptable excipients.

55. A method for controlling the level of one or more inflammation inducing cytokines selected from the group consisting of interleukin-1 (IL-1), Tumor Necrosis Factor-α (TNF-α), interleukin-6 (IL-6), and interleukin-8 (IL-8) and thereby controlling, mediating, or abating disease states affected by the levels of these extracellular inflammatory cytokines, said method comprising the step of administering to a human or higher mammal an effective amount of a pharmaceutical composition comprising:
A) an effective amount of one or more 1,2-dihydropyrazol-3-ones, or enantiomeric and diasteriomeric forms or pharmaceutically acceptable salts thereof, said compound having the formula:

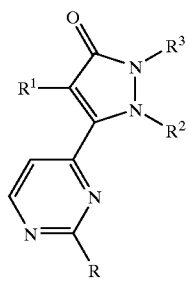

wherein R is:
a) —O[$CH_2$]$_n R^4$; or
b) —$N^{5a}R^{5b}$;
   $R^4$ is substituted or unsubstituted $C_1$–$C_{10}$ linear, branched, or cyclic alkyl;
   substituted or unsubstituted aryl; substituted or unsubstituted heterocyclic; or
   substituted or unsubstituted heteroaryl; the index n is from 0 to 5;
$R^{5a}$ and $R^{5b}$ are each independently:
a) hydrogen; or
b) —[C($R^{6a}R^{6b}$)]$_m R^7$;
   each $R^{6a}$ and $R^{6b}$ is independently:
   i) hydrogen;
   ii) —$OR^8$;
   iii) —$N(R^8)_2$;
   iv) —$CO_2 R^8$;
   v) —$CON(R^8)_2$;
   vi) substituted or unsubstituted $C_1$–$C_4$ linear, branched, or cyclic alkyl;
   vii) and mixtures thereof;
$R^7$ is
   i) hydrogen;
   ii) substituted or unsubstituted $C_1$–$C_6$ linear, branched, or cyclic alkyl;
   iii) substituted or unsubstituted heterocyclic;
   iv) substituted or unsubstituted aryl;
   v) substituted or unsubstituted heteroaryl;
   vi) —$OR^8$;
   vii) —$N(R^8)_2$;
   viii) —$CO_2 R^8$; and
   ix) —$CON(R^8)_2$;
$R^8$ is hydrogen, a water-soluble cation, $C_1$–$C_4$ alkyl, or substituted or unsubstituted aryl;
the index m is from 0 to 5;
$R^1$ is substituted phenyl;
each $R^2$ and $R^3$ unit is independently selected from the group consisting of:
   a) hydrogen; and
   b) substituted or unsubstituted $C_1$–$C_{10}$ hydrocarbyl selected from the group consisting of:
      i) $C_1$–$C_{10}$ linear, branched or cyclic alkyl;
      ii) $C_6$–$C_{10}$ aryl;
      iii) $C_1$–$C_{10}$ heterocyclic;
      iv) $C_1$–$C_{10}$ heteroaryl; and
B) one or more pharmaceutically acceptable excipients.

* * * * *

UNITED STATES PATENT AND TRADEMARK OFFICE
CERTIFICATE OF CORRECTION

PATENT NO. : 6,677,337 B2
APPLICATION NO. : 10382060
DATED : March 5, 2003
INVENTOR(S) : Matthew John Laufersweiler et al.

It is certified that error appears in the above-identified patent and that said Letters Patent is hereby corrected as shown below:

Column 14,
Lines 25-55, delete

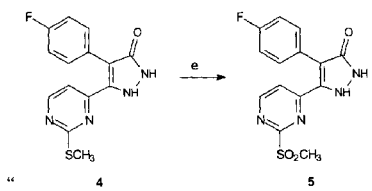

Reagents and conditions: (d) Oxone®, MeOH/THF/H$_2$O; rt, 1 hr.

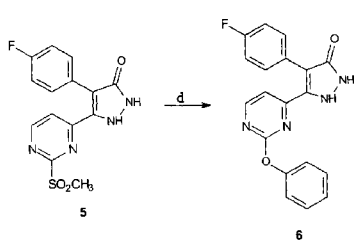

Reagents and conditions: (e) phenol, NaH, THF, 1.5 hr rt."

and insert --

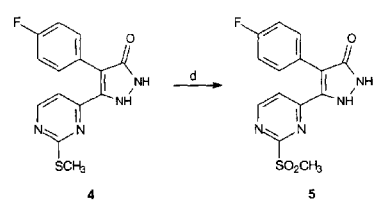

Reagents and conditions: (d) Oxone®, MeOH/THF/H$_2$O; rt, 1 hr.

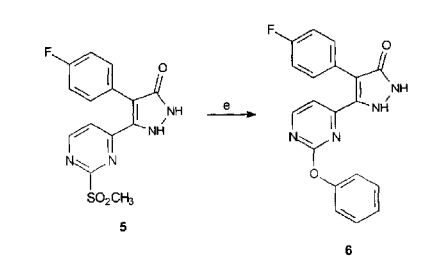

Reagents and conditions: (e) phenol, NaH, THF, 1.5 hr rt.--.

UNITED STATES PATENT AND TRADEMARK OFFICE
CERTIFICATE OF CORRECTION

PATENT NO.       : 6,677,337 B2
APPLICATION NO.  : 10382060
DATED            : March 5, 2003
INVENTOR(S)      : Matthew John Laufersweiler et al.

It is certified that error appears in the above-identified patent and that said Letters Patent is hereby corrected as shown below:

Column 27,
Insert missing structures 15, 16 and 17
--

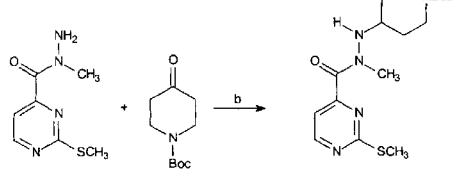

Reagents and conditions: (b) i) reflux 0.5 hr; ii) NaCNBH₃, HCl, EtOH; rt, 3 hr.

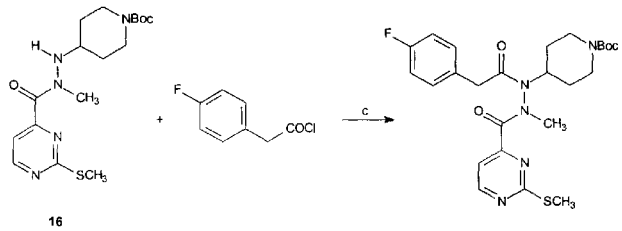

Reagents and conditions: (c) pyridine; rt, 2 hr.                  --.

Column 29,
Line 16, delete "(m, 2H)" and insert -- (m, 1H) --.

Column 44,
Line 17-34, delete "

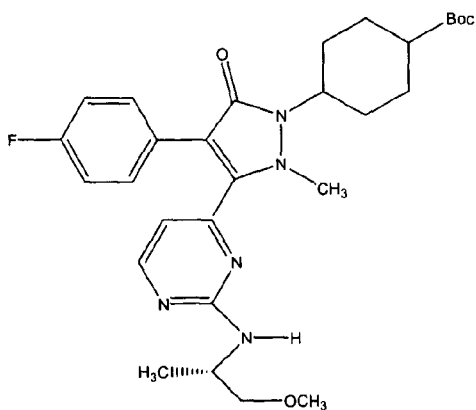

"

UNITED STATES PATENT AND TRADEMARK OFFICE
CERTIFICATE OF CORRECTION

PATENT NO. : 6,677,337 B2
APPLICATION NO. : 10382060
DATED : March 5, 2003
INVENTOR(S) : Matthew John Laufersweiler et al.

It is certified that error appears in the above-identified patent and that said Letters Patent is hereby corrected as shown below:

Column 44 (cont'd),
and insert --

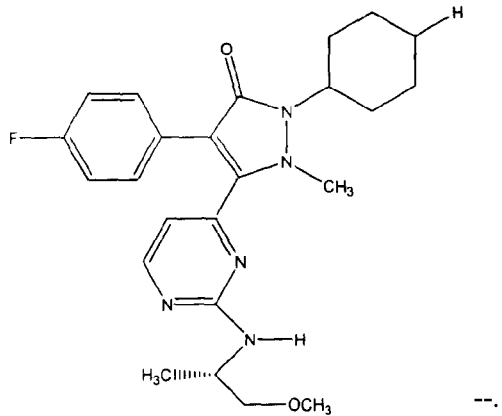

--.

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,677,337 B2  Page 1 of 3
APPLICATION NO. : 10/382060
DATED : January 13, 2004
INVENTOR(S) : Matthew John Laufersweiler et al.

It is certified that error appears in the above-identified patent and that said Letters Patent is hereby corrected as shown below:

Column 14,
Lines 25-55, delete

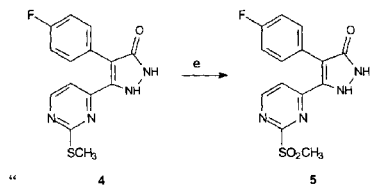

"          4                    5

Reagents and conditions: (d) Oxone®, MeOH/THF/H₂O; rt, 1 hr.

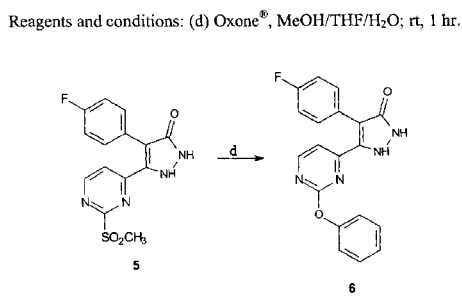

Reagents and conditions: (e) phenol, NaH, THF, 1.5 hr rt."

and insert --

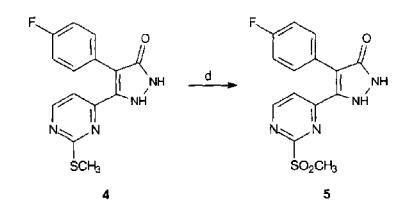

Reagents and conditions: (d) Oxone®, MeOH/THF/H₂O; rt, 1 hr.

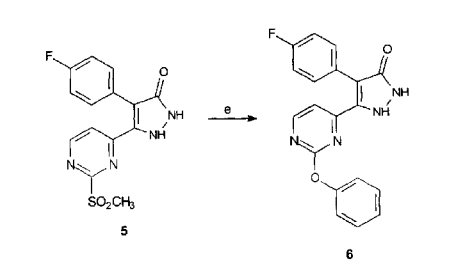

Reagents and conditions: (e) phenol, NaH, THF, 1.5 hr rt.--.

UNITED STATES PATENT AND TRADEMARK OFFICE
CERTIFICATE OF CORRECTION

PATENT NO.       : 6,677,337 B2                           Page 2 of 3
APPLICATION NO.  : 10/382060
DATED            : January 13, 2004
INVENTOR(S)      : Matthew John Laufersweiler et al.

It is certified that error appears in the above-identified patent and that said Letters Patent is hereby corrected as shown below:

Column 27,
Insert missing structures 15, 16 and 17
--

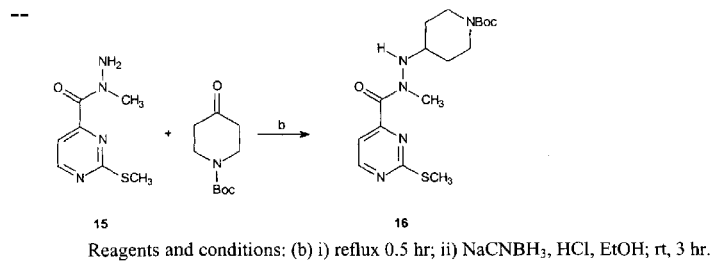

Reagents and conditions: (b) i) reflux 0.5 hr; ii) NaCNBH₃, HCl, EtOH; rt, 3 hr.

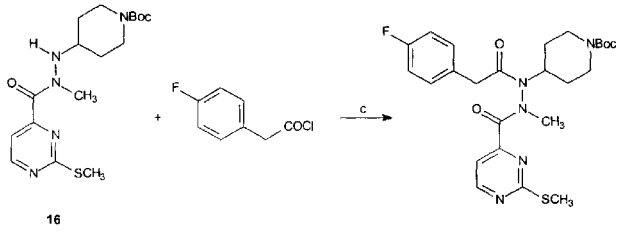

Reagents and conditions: (c) pyridine; rt, 2 hr.         --.

Column 29,
Line 16, delete "(m, 2H)" and insert -- (m, 1H) --.

Column 44,
Line 17-34, delete "

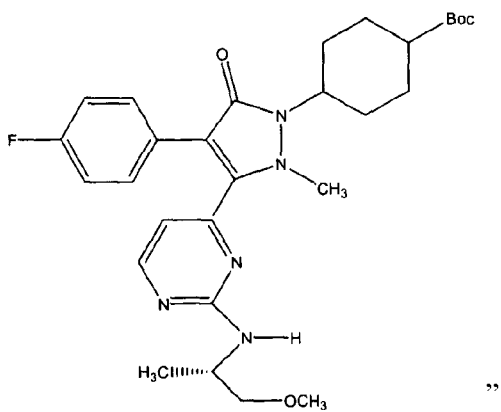

"

UNITED STATES PATENT AND TRADEMARK OFFICE
CERTIFICATE OF CORRECTION

PATENT NO. : 6,677,337 B2
APPLICATION NO. : 10/382060
DATED : January 13, 2004
INVENTOR(S) : Matthew John Laufersweiler et al.

It is certified that error appears in the above-identified patent and that said Letters Patent is hereby corrected as shown below:

Column 44 (cont'd),
and insert --

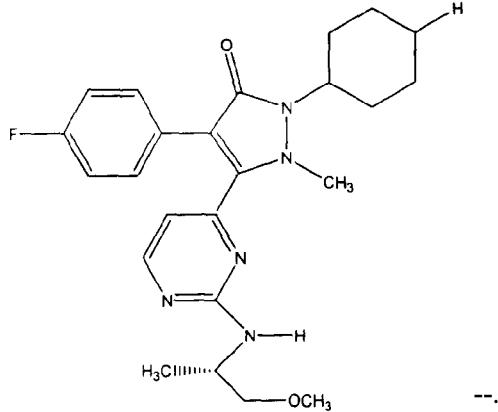

--.

This certificate supersedes Certificate of Correction issued August 22, 2006.

Signed and Sealed this

Tenth Day of October, 2006

JON W. DUDAS
*Director of the United States Patent and Trademark Office*